United States Patent
Dantus

(10) Patent No.: US 7,973,936 B2
(45) Date of Patent: Jul. 5, 2011

(54) CONTROL SYSTEM AND APPARATUS FOR USE WITH ULTRA-FAST LASER

(75) Inventor: Marcos Dantus, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1643 days.

(21) Appl. No.: 11/219,572

(22) Filed: Sep. 2, 2005

(65) Prior Publication Data

US 2006/0187974 A1    Aug. 24, 2006

Related U.S. Application Data

(63) Continuation-in-part of application No. 10/265,211, filed on Oct. 4, 2002, now Pat. No. 7,450,618, which is a continuation-in-part of application No. PCT/US02/02548, filed on Jan. 28, 2002, application No. 11/219,572, which is a continuation-in-part of application No. 10/628,874, filed on Jul. 28, 2003, now Pat. No. 7,105,811, which is a continuation of application No. PCT/US02/02548, application No. 11/219,572, which is a continuation-in-part of application No. 10/791,377, filed on Mar. 2, 2004, now Pat. No. 7,609,731, which is a continuation-in-part of application No. 10/265,211, which is a continuation-in-part of application No. PCT/US02/02548.

(60) Provisional application No. 60/265,133, filed on Jan. 30, 2001.

(51) Int. Cl.
*G01B 9/02* (2006.01)

(52) U.S. Cl. .................................................. 356/451
(58) Field of Classification Search .............. 359/239; 372/25, 38.1, 38.01, 38.02, 38.08; 356/451
See application file for complete search history.

(56) References Cited

U.S. PATENT DOCUMENTS

| | | | |
|---|---|---|---|
| 3,214,563 A | 10/1965 | Ford | |
| 3,611,182 A | 10/1971 | Treacy | |
| 3,919,881 A | 11/1975 | Metherell | |

(Continued)

FOREIGN PATENT DOCUMENTS

EP    0605110 A2    7/1994

(Continued)

OTHER PUBLICATIONS

Fowles, "Introduction to Modern Optics," 1989, Dover 2e, pp. 2-19 (esp. sections 1.3-1.5).*

(Continued)

*Primary Examiner* — Gregory J Toatley
*Assistant Examiner* — Scott M Richey
(74) *Attorney, Agent, or Firm* — Harness, Dickey & Pierce, P.L.C.

(57) ABSTRACT

A control system and apparatus for use with an ultra-fast laser is provided. In another aspect of the present invention, the apparatus includes a laser, pulse shaper, detection device and control system. A multiphoton intrapulse interference method is used to characterize the spectral phase of laser pulses and to compensate any distortions in an additional aspect of the present invention. In another aspect of the present invention, a system employs multiphoton intrapulse interference phase scan. Furthermore, another aspect of the present invention locates a pulse shaper and/or MIIPS unit between a laser oscillator and an output of a laser amplifier.

55 Claims, 25 Drawing Sheets

U.S. PATENT DOCUMENTS

| | | | |
|---|---|---|---|
| 3,988,704 A | 10/1976 | Rice et al. | |
| 4,167,662 A | 9/1979 | Steen | |
| 4,288,691 A | 9/1981 | Horton | |
| 4,394,780 A | 7/1983 | Mooradian | |
| 4,477,905 A | 10/1984 | Sweeney | |
| 4,512,660 A | 4/1985 | Goldberg | |
| 4,621,006 A | 11/1986 | Terry et al. | |
| 4,655,547 A | 4/1987 | Heritage et al. | |
| 4,746,193 A | 5/1988 | Heritage et al. | |
| 4,754,760 A * | 7/1988 | Fukukita et al. | 600/438 |
| 4,772,854 A | 9/1988 | Silberberg | |
| 4,812,776 A | 3/1989 | Sasaki | |
| 4,819,239 A | 4/1989 | Sharp et al. | |
| 4,834,474 A | 5/1989 | George et al. | |
| 4,853,065 A | 8/1989 | Terry et al. | |
| 4,856,860 A | 8/1989 | Silberberg et al. | |
| 4,866,699 A | 9/1989 | Brackett et al. | |
| 4,913,934 A | 4/1990 | Sharp et al. | |
| 4,928,316 A | 5/1990 | Heritage et al. | |
| 4,999,840 A | 3/1991 | Negus | |
| 5,021,282 A | 6/1991 | Terry et al. | |
| 5,034,613 A | 7/1991 | Denk | |
| 5,048,029 A | 9/1991 | Skupsky et al. | |
| 5,077,619 A | 12/1991 | Toms | |
| 5,095,487 A | 3/1992 | Meyerhofer et al. | |
| 5,130,994 A * | 7/1992 | Madey et al. | 372/2 |
| 5,132,512 A | 7/1992 | Sanders et al. | |
| 5,132,824 A | 7/1992 | Patel et al. | |
| 5,154,963 A | 10/1992 | Terry | |
| 5,166,818 A | 11/1992 | Chase et al. | |
| 5,239,607 A | 8/1993 | da Silva et al. | |
| 5,341,236 A | 8/1994 | Stappaerts | |
| 5,359,410 A | 10/1994 | Diels et al. | |
| 5,406,408 A | 4/1995 | Ellingson et al. | |
| 5,414,540 A | 5/1995 | Patel et al. | |
| 5,414,541 A | 5/1995 | Patel et al. | |
| 5,463,200 A | 10/1995 | James et al. | |
| 5,491,551 A * | 2/1996 | Mattson | 356/451 |
| 5,526,155 A | 6/1996 | Knox et al. | |
| 5,526,171 A | 6/1996 | Warren | |
| 5,530,544 A | 6/1996 | Trebino et al. | |
| 5,541,947 A | 7/1996 | Mourou et al. | |
| 5,585,913 A | 12/1996 | Hariharan et al. | |
| 5,589,955 A | 12/1996 | Amako et al. | |
| 5,615,673 A | 4/1997 | Berger et al. | |
| 5,631,758 A | 5/1997 | Knox et al. | |
| 5,637,966 A | 6/1997 | Umstadter et al. | |
| 5,682,262 A | 10/1997 | Wefers et al. | |
| 5,684,595 A | 11/1997 | Kato et al. | |
| 5,689,361 A | 11/1997 | Damen et al. | |
| 5,704,700 A | 1/1998 | Kappel et al. | |
| 5,719,650 A | 2/1998 | Wefers et al. | |
| 5,754,292 A | 5/1998 | Kane et al. | |
| 5,759,767 A | 6/1998 | Lakowicz | |
| 5,774,213 A | 6/1998 | Trebino et al. | |
| 5,793,091 A | 8/1998 | Devoe | |
| 5,798,867 A | 8/1998 | Uchida et al. | |
| 5,822,097 A | 10/1998 | Tournois | |
| 5,828,459 A | 10/1998 | Silberberg | |
| 5,832,013 A | 11/1998 | Yessik et al. | |
| 5,883,309 A | 3/1999 | Vossiek et al. | |
| 5,936,732 A | 8/1999 | Smirl et al. | |
| 5,956,173 A | 9/1999 | Svelto et al. | |
| 5,994,687 A | 11/1999 | Chanteloup et al. | |
| 6,002,480 A | 12/1999 | Izatt et al. | |
| 6,008,899 A | 12/1999 | Trebino et al. | |
| 6,042,603 A | 3/2000 | Fisher et al. | |
| 6,057,919 A | 5/2000 | Machida et al. | |
| 6,058,132 A | 5/2000 | Iso et al. | |
| 6,072,813 A | 6/2000 | Tournois | |
| 6,080,148 A | 6/2000 | Damasco et al. | |
| 6,081,543 A | 6/2000 | Liu et al. | |
| 6,111,251 A | 8/2000 | Hillenkamp | |
| 6,130,426 A | 10/2000 | Laukien et al. | |
| 6,156,527 A | 12/2000 | Schmidt et al. | |
| 6,160,626 A * | 12/2000 | Debeau et al. | 356/451 |
| 6,166,385 A | 12/2000 | Webb et al. | |
| 6,184,490 B1 | 2/2001 | Schweizer | |
| 6,191,386 B1 | 2/2001 | Albright et al. | |
| 6,219,142 B1 | 4/2001 | Kane | |
| 6,259,104 B1 | 7/2001 | Baer | |
| 6,272,156 B1 | 8/2001 | Reed et al. | |
| 6,288,782 B1 | 9/2001 | Worster | |
| 6,296,810 B1 | 10/2001 | Ulmer | |
| 6,316,153 B1 | 11/2001 | Goodman | |
| 6,327,068 B1 | 12/2001 | Silberberg et al. | |
| 6,337,606 B1 | 1/2002 | Brombaugh et al. | |
| 6,344,653 B1 | 2/2002 | Webb et al. | |
| 6,391,229 B1 | 5/2002 | Watanabe et al. | |
| 6,396,856 B1 | 5/2002 | Sucha et al. | |
| 6,402,898 B1 | 6/2002 | Brumer et al. | |
| 6,421,154 B1 | 7/2002 | Diels et al. | |
| 6,479,822 B1 | 11/2002 | Nelson et al. | |
| 6,480,656 B1 | 11/2002 | Islam et al. | |
| 6,498,801 B1 | 12/2002 | Dudelzak et al. | |
| 6,504,612 B2 | 1/2003 | Trebino | |
| 6,515,257 B1 | 2/2003 | Jain et al. | |
| 6,566,667 B1 | 5/2003 | Partlo et al. | |
| 6,573,493 B1 | 6/2003 | Futami et al. | |
| 6,577,782 B1 | 6/2003 | Leaird et al. | |
| 6,610,351 B2 | 8/2003 | Shchegolikhin et al. | |
| 6,610,977 B2 | 8/2003 | Megerle | |
| 6,621,613 B2 * | 9/2003 | Silberberg et al. | 359/239 |
| 6,625,181 B1 | 9/2003 | Oshemkov et al. | |
| 6,678,450 B1 | 1/2004 | Franson | |
| 6,697,196 B2 | 2/2004 | Suzuki | |
| 6,723,991 B1 | 4/2004 | Sucha et al. | |
| 6,757,463 B2 | 6/2004 | Hutchinson et al. | |
| 6,795,456 B2 | 9/2004 | Scaggs | |
| 6,795,777 B1 | 9/2004 | Scully et al. | |
| 6,801,318 B2 * | 10/2004 | Fu et al. | 356/450 |
| 6,801,551 B1 | 10/2004 | Delfyett et al. | |
| 6,804,000 B2 | 10/2004 | Roorda et al. | |
| 6,857,744 B2 | 2/2005 | Nakada et al. | |
| 6,879,426 B1 | 4/2005 | Weiner | |
| 6,885,325 B2 | 4/2005 | Omelyanchouk et al. | |
| 6,915,040 B2 | 7/2005 | Willner et al. | |
| 6,930,779 B2 * | 8/2005 | McGrew | 356/450 |
| 6,963,591 B2 | 11/2005 | Tulloch et al. | |
| 7,033,519 B2 | 4/2006 | Taylor et al. | |
| 7,049,543 B2 | 5/2006 | Roos et al. | |
| 7,096,125 B2 | 8/2006 | Padmanabhan et al. | |
| 7,105,811 B2 * | 9/2006 | Dantus et al. | 250/288 |
| 7,132,223 B2 | 11/2006 | Schroeder et al. | |
| 7,169,709 B2 | 1/2007 | Koide | |
| 7,170,030 B2 | 1/2007 | Haight et al. | |
| 7,170,598 B2 | 1/2007 | Walla et al. | |
| 7,177,027 B2 * | 2/2007 | Hirasawa et al. | 356/451 |
| 7,276,103 B2 | 10/2007 | Wöste et al. | |
| 7,289,203 B2 * | 10/2007 | Frankel | 356/301 |
| 7,342,223 B2 | 3/2008 | Ohkubo et al. | |
| 7,348,569 B2 | 3/2008 | Feurer et al. | |
| 7,352,469 B2 * | 4/2008 | McGrew | 356/451 |
| 7,411,166 B2 | 8/2008 | Wolleschensky et al. | |
| 7,439,497 B2 | 10/2008 | Dantus et al. | |
| 7,450,239 B2 * | 11/2008 | Uehara et al. | 356/451 |
| 7,450,618 B2 * | 11/2008 | Dantus et al. | 372/25 |
| 7,609,731 B2 * | 10/2009 | Dantus et al. | 372/30 |
| 7,826,051 B2 | 11/2010 | Silberberg et al. | |
| 2001/0015990 A1 | 8/2001 | Miyai | |
| 2001/0017727 A1 | 8/2001 | Sucha et al. | |
| 2002/0025490 A1 | 2/2002 | Shchegolikhin et al. | |
| 2002/0086245 A1 | 7/2002 | Zait et al. | |
| 2002/0097761 A1 | 7/2002 | Sucha et al. | |
| 2003/0063884 A1 | 4/2003 | Smith et al. | |
| 2003/0099264 A1 | 5/2003 | Dantus et al. | |
| 2003/0123051 A1 | 7/2003 | McGrew | |
| 2003/0194165 A1 | 10/2003 | Silberberg et al. | |
| 2003/0210400 A1 | 11/2003 | Joffre et al. | |
| 2004/0012837 A1 | 1/2004 | Kaplan et al. | |
| 2004/0021243 A1 | 2/2004 | Shih et al. | |
| 2004/0031906 A1 | 2/2004 | Glecker | |
| 2004/0058058 A1 | 3/2004 | Shchegolikhin et al. | |
| 2004/0089804 A1 | 5/2004 | Dantus et al. | |
| 2004/0128081 A1 | 7/2004 | Rabitz et al. | |
| 2004/0145735 A1 | 7/2004 | Silberberg et al. | |
| 2004/0155184 A1 | 8/2004 | Stockman et al. | |

| | | | |
|---|---|---|---|
| 2004/0233944 A1 | 11/2004 | Dantus et al. | |
| 2004/0240037 A1 | 12/2004 | Harter | |
| 2004/0263950 A1 | 12/2004 | Fermann et al. | |
| 2005/0021243 A1 | 1/2005 | Dantus et al. | |
| 2005/0036202 A1 | 2/2005 | Cohen et al. | |
| 2005/0103759 A1 | 5/2005 | Li et al. | |
| 2005/0155958 A1 | 7/2005 | Arai et al. | |
| 2005/0161669 A1 | 7/2005 | Jovanovich et al. | |
| 2005/0185188 A1 | 8/2005 | McGrew | |
| 2005/0226287 A1 | 10/2005 | Shah et al. | |
| 2005/0230365 A1 | 10/2005 | Lei et al. | |
| 2005/0232313 A1 | 10/2005 | Fermann et al. | |
| 2006/0000988 A1 | 1/2006 | Stuart et al. | |
| 2006/0006964 A1 | 1/2006 | Huang et al. | |
| 2006/0019171 A1 | 1/2006 | Hosono et al. | |
| 2006/0028655 A1 | 2/2006 | Cordingley et al. | |
| 2006/0032841 A1 | 2/2006 | Tan et al. | |
| 2006/0039419 A1 | 2/2006 | Deshi | |
| 2006/0051025 A1 | 3/2006 | Mizuuchi et al. | |
| 2006/0056468 A1 | 3/2006 | Dantus et al. | |
| 2006/0058683 A1 | 3/2006 | Chance | |
| 2006/0066848 A1 | 3/2006 | Frankel | |
| 2006/0071803 A1 | 4/2006 | Hamburger et al. | |
| 2006/0096426 A1 | 5/2006 | Park | |
| 2006/0096962 A1 | 5/2006 | Park | |
| 2006/0119743 A1 | 6/2006 | Lin | |
| 2006/0120412 A1 | 6/2006 | Liu | |
| 2006/0134004 A1 | 6/2006 | Gellermann et al. | |
| 2006/0169677 A1 | 8/2006 | Deshi | |
| 2006/0207975 A1 | 9/2006 | Ehrmann et al. | |
| 2006/0207976 A1 | 9/2006 | Bovatsek et al. | |
| 2006/0243712 A1 | 11/2006 | Haight et al. | |
| 2006/0274403 A1 | 12/2006 | Kaplan et al. | |
| 2006/0285071 A1 | 12/2006 | Erickson et al. | |
| 2007/0034615 A1 | 2/2007 | Kleine | |
| 2007/0093970 A1 | 4/2007 | Padmanabhan et al. | |
| 2008/0309931 A1 | 12/2008 | Silberberg et al. | |

FOREIGN PATENT DOCUMENTS

| | | |
|---|---|---|
| EP | 1742311 A1 | 1/2007 |
| JP | 2003 155256 A | 5/2003 |
| WO | WO 99/57318 | 11/1999 |
| WO | WO 00/70647 | 11/2000 |
| WO | WO-0070647 A1 | 11/2000 |
| WO | WO 01/54323 | 7/2001 |
| WO | WO 02/061799 | 8/2002 |
| WO | WO-2004023413 A2 | 3/2004 |
| WO | WO 2005/088783 | 9/2005 |
| WO | WO-2005111677 A2 | 11/2005 |
| WO | WO-2006079083 A2 | 7/2006 |
| WO | WO-2006138442 A2 | 12/2006 |
| WO | WO-2007001308 A2 | 1/2007 |
| WO | WO-2007145702 A2 | 12/2007 |

OTHER PUBLICATIONS

Weiner, "Programmable Shaping of Femtosecond Optical Pulses by Use of 128-Element Liquid Crystal Phase Modulator," Apr. 1992, IEEE J. of Quantum Electronics, vol. 28, No. 4, pp. 908-920.*

Zeek, Erik; "Pulse Shaping for High-Harmonic Generation;" Dissertation Submitted in Partial Fulfillment of the Requirements for the Degree of Doctor of Philosophy (Applied Physics) in the University of Michigan, 2000; 126 pages.

Feurer, T., et al.; "Coherent Control Over Collective Polariton Excitations: The Dawn of Polaritonics;" 2002 Thirteenth International Conference on Ultrafast Phenomena, Technical Digest (Tops vol. 72); Opt. Soc. America; XP008086358; pp. 541-545.

Sato, Masamichi, et al.; "Adaptive Pulse Shaping of Femtosecond Laser Pulses in Amplitude and Phase Through a Single-Mode Fiber by Referring to Frequency-Resolved Optical Gating Patterns;" Jpn. J. Appl. Phys., vol. 41 (2002); Part 1 No. 6A, Jun. 2002; XP-002436366; pp. 3704-3709.

Gee, S., et al.; "Ultrashort Pulse Generation by Intracavity Spectral Shaping and Phase Compensation of External-Cavity Modelocked Semiconductor Lasers;" IEEE Journal of Quantum Electronics, vol. 36, No. 9, Sep. 2000; XP-002462407; pp. 1035-1040.

Scaffidi, J., et al.; "Spatial and Temporal Dependence of Interspark Interactions in Femtosecond-Nanosecond Dual-Pulse Laser-Induced Breakdown Spectroscopy;" Applied Optics, vol. 43, No. 27, Sep. 20, 2004; XP-002462408; pp. 5243-5250.

Pfeiffer, W., et al.; "Ultrafast Spatio-Temporal Near-Field Control;" IEEE 2005 European Quantum Electronics Conference, 0-7803-8973-5/05; p. 169 (1 page).

"Shape Your Pulses. Control Your Experiment." advertisement, Laser Focus World, (Dec. 1997) p. 26, CRI, Inc.

Atabek, O. et al., Intense Laser Control of the Chemical Bond, Theochem Elsevier Netherlands, vol. 493, Dec. 15, 1999, pp. 89-101.

Barry, Liam P., et al., "A High-Speed Optical Star Network Using TDMA and All-Optical Demultiplexing Techniques", IEEE Journal on Selected Areas in Communications, vol. 14, No. 5, (Jun. 1996), pp. 1030-1038.

Brattke, S. et al.; "Generation of Photon Number States on Demand via Cavity Quantum Electrodynamics"; Phys. Rev. Lett.; vol. 86; Apr. 16, 2001; pp. 3534-3537.

Chen J. et al., Femtosecond Laser-Induced Dissociative Ionization and Coulomb Explosion of Ethanol, International Journal of Mass Spectrometry, Elsevier, Amsterdam, NL, vol. 241, No. 1, Feb. 15, 2005, pp. 25-29.

Cumpston, B.H. et al.; "New Photopolymers based on Two-Photon Absorbing Chromophores and Application to Three-Dimensional Microfabricaton and Optical Storage"; Mat. Res. Soc. Symp. Proc; vol. 488; 1998; pp. 217-225.

Cumpston,B.H. et al.; "Two-photon polymerization initiators for three-dimensional optical data storage and microfabrication"; Letters to Nature; vol. 398; Mar. 4, 1999; pp. 51-54.

Delfyett, Peter J., et al., "High-Power Ultrafast Laser Diodes", IEEE Journal of Quantum Electronics, vol. 28, No. 10, (Oct. 1992), pp. 2203-2219.

Dreischuh, A., Experimental Demonstraction of Pulse Shaping and Shortening by Spatial Filtering of an Induced-Phase-Modulated Probe Wave, IEEE Journal of Quantum Electronics, vol. 33, No. 3, (Mar. 1997), pp. 329-335.

Dugan, M.A., et al., "High-resolution acousto-optic shaping of unamplified and amplified femtosecond laser pulses", J. Opt. Soc. Am. B, vol. 14, No. 9, (Sep. 1997), pp. 2348-2358, Optical Society of America.

Efimov, A., et al., "Programmable shaping of ultrabroad-bandwidth pulses from a Ti:sapphire laser", Journal B/vol. 12, No. 10 (Oct. 1995) pp. 1968-1980, Optical Society of America.

Fermann, M.E., et al., "Additive-pulse-compression mode locking of a neodymium fiber laser", Optics Letters, vol. 16, No. 4, (Feb. 15, 1991), Optical Society of America.

Fetterman, et al., "Ultrafast pulse shaping: amplification and characterization", Optics Express, vol. 3, No. 10, (Nov. 9, 1998), pp. 366-375.

Fork, R.L., et al., "Compression of optical pulses to six femtoseconds by using cubic phase compensation", Optics Letters, (Jul. 1987), vol. 12, No. 7, Optical Society of America.

Gomes, A.S.L., et al., "Optical fibre-grating pulse compressors", Tutorial Review, Optical and Quantum Electronics 20, (1988), pp. 95-112.

Goswami, D.; "Ultrafast Pulse Shaping Approaches to Quantum Computing"; Indian Institute of Technology; Dec. 24, 2003 (8 pages).

Haner, M., et al., "Generation of programmable, picosecond-resolution shaped laser pulses by fiber-grating pulse compression", Optics Letters, vol. 12, No. 6, (Jun. 1987), pp. 398-400, Optical Society of America.

Heritage, J.P., "Picosecond pulse shaping by spectral phase and amplitude manipulation", Optics Letters, vol. 10, No. 12, (Dec. 1985), pp. 609-611, Optical Society of America.

Kapteyn, Henry C. et al.; "A Comparison of Multipass Vs. Regenerative Ti:Sapphire Laser Amplifiers;" Kapteyn-Murnane Laboratories Inc., Boulder, CO, USA, www.kmlabs.com; 2 pages.

Konorov, S.O., "Laser Breakdown with Millijoule Trains of Picosecond Pulses Transmitted through a Hollow-Core Photonic-Crystal Fiber", Laser Physics, vol. 13, No. 4, (2003) pp. 652-656.

Krausz, F., et al., "Generation of 33-fs optical pulses from a solid-state laser", Optics Letters, (Feb. 1, 1992), vol. 17, No. 3, Optical Society of America.

Lemoff, B.E., et al., "Quintic-phase-limited, spatially uniform expansion and recompression of ultrashort optical pulses", Optics Letters, vol. 18, No. 19, (Oct. 1, 1993), pp. 1651-1653, Optical Society of America.

Liu, Yongqian, et al., "Terahertz Waveform Synthesis via Optical Pulse Shaping", IEEE Journal of Selected Topics in Quantum Electronics, (Sep. 1996), vol. 2, No. 3, pp. 709-719.

Lu, Y.M. et al.; "Highly sensitive two-photon chromophores applied to three dimensional lithographic microfabrication: design, synthesis and characterization towards two-photon absorbtion cross section"; J. Mater Chem. 14(1); 2004; pp. 75-80.

Ma R., et al., Intense Femtosecond Laser Field-Induced Coulomb Fragmentation of C2H4, International Journal of Mass Spectrometry, Elsevier, Amsterdam, NL, vol. 242, No. 1, Mar. 15, 2005, pp. 43-48.

Meshulach, D., et al., "Adaptive Compression of Femtosecond Pulses", presented at the Ultrafast Optics 1997 Conference, Aug. 1997, Monterey California (3 pages).

Mitra et al.; "Nonlinear Limits to the Information Capacity of Optical Fibre Communications"; Nature; vol. 411; Jun. 28, 2001; pp. 1027-1030.

Motzkus, M., Open and Closed Loop Control of Complex Molecules with Shaped fs Pulses, 2003 International Conference Physics and Control. Proceedings (Cat. No. 03EX708), IEEE Piscataway, NJ, USA, vol. 3, 2003, p. 746, vol. 3.

Nisoli, M., et al., "Compression of high-energy laser pulses below 5fs", Optics Letters, (Apr. 15, 1997) vol. 22, No. 8, pp. 522-524, Optical Society of America.

Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.

Pelfang Tian et al., Femtosecond Phase-Coherent Two-Dimensional Spectroscopy, Science American Assoc. Adv. Sci. USA, vol. 300, No. 5625, Jun. 6, 2003, pp. 1553-1555.

Perry, Michael D., et al., "Terawatt to Petawatt Subpicosecond Lasers", Articles, (May 13, 1994), vol. 264, Science.

Postnikova, B.J. et al.; "Towards nanoscale three-dimensional fabrication using two-photon initiated polymerization and near-field excitation"; Microelectron. Eng. 69 (2-4); Sep. 2003; pp. 459-465.

Quiroga-Teixeiro, M.L., et al., "Compression of optical solitons by conversion of nonlinear modes", J. Opt. Soc. Am. B, vol. 12, No. 6, (Jun. 1995), pp. 1110-1116, Optical Society of America.

R. Wolleschensky et al.; "Characterization and Optimization of a Laser-Scanning Microscope in the Femtosecond Regime;" Applied Physics B 67, Lasers and Optics, 1998; pp. 87-94.

Reitze, D.H., et al., "Shaping of wide bandwidth 20 femtosecond optical pulses", Appl. Phys. Lett. 61 (11), (Sep. 14, 1992), pp. 1260-1262, American Institute of Physics.

Roth, M. et al., Acousto-Optic Femtosecond Pulse Shaping in the Ultraviolet, Lasers and Electro-Optics, 2005. (Cleo). Conference in Baltimore, Md., USA, May 22-27, 2005, Piscataway, NJ, USA. IEEE, May 22, 2005, pp. 2244-2246.

Roth, M. et al., Acousto-optical Shaping of Ultraviolet Femtosecond Pulses, Applied Physics B; Lasers and Optics, Springer-Verlag, BE, vol. 80, No. 4-5, Apr. 1, 2005, pp. 441-444.

S. Kovtoun et al.; "Mass-Correlated Pulsed Extraction : Theoretical Analysis and Implementation With a Linear Matrix-Assisted Laser Desorption/Ionization Time of Flight Mass Spectrometer;" Journal of the American Society for Mass Spectrometry, Elsevier Science Inc., vol. 11, 2000; pp. 841-853.

Spielmann, C., et al., "Ti: Sapphire Laser Produces Intense Sub-5-FS Pulses", Laser Focus World, May 97, vol. 33, Issue 5, p. 127.

Sun, H.B. et al.; "Two-photon laser precision microfabrication and its applications to micronano devices and systems"; J. Lightwave Technol. 21(3); Mar. 2003; pp. 624-633.

Szipöcs, Robert, et al., "Chirped multilayer coatings for broadband dispersion control in femtosecond lasers", Optics Letters, (Feb. 1, 1994), vol. 19, No. 3, Optical Society of America.

Thanopulos I. et al: Laser-Driven Coherent Manipulation of Molecular Chirality, Chemical Physics Letters Elsevier Netherlands, vol. 390, No. 1-3, May 21, 2004, pp. 228-235.

Tomizawa H. et al., Development of Automatically Optimizing System of Both Spatial and Temporal Beam Shaping for UV-Laser Pulse, Proceedings of the SPIE—The International Society for Optical Engineering SPIE—Int. Soc. Opt. Eng USA, vol. 5481, No. 1, 2004, pp. 47-55.

Trebino, Rick, et al., "Using phase retrieval to measure the intensity and phase of ultrashort pulses: frequency-resolved optical gating", J. Opt. Soc. Am. A, vol. 10, No. 5, (May 1993), pp. 1101-1111, Optical Society of America.

Umstadter, D., et al., "Nonlinear Plasma Waves Resonantly Driven by Optimized Laser Pulse Trains", Physical Review Letters, vol. 72, No. 8, (Feb. 21, 1994), pp. 1224-1227, The American Physical Society.

VandenBout, D.A. et al.; "Discrete intensity jumps and intramolecular electronic energy transfer in the spectroscopy of single conjugated polymer molecules"; Science 277; 1997; pp. 1074-1077.

Warren, W.S., et al., "Coherent Control of Quantum Dynamics: The Dream is Alive", Articles, Science, (Mar. 12, 1993), vol. 259.

Wefers, Marc M., "Programmable phase and amplitude femtosecond pulse shaping", Optics Letters (Dec. 1, 1993), vol. 18, No. 23, pp. 2032-2034.

Wefers, Marc, et al., "Generation of high-fidelity programmable ultrafast optical waveforms", Optics Letters, (May 1, 1995), vol. 20, No. 9, Optical Society of America.

Weiner, "Encoding and decoding of femtosecond pulses", Optics Letters, (Apr. 1988), vol. 13, No. 4, Optical Society of America.

Weiner, A.M., "Enhancement of coherent charge oscillations in coupled quantum wells by femtosecond pulse shaping", J. Opt. Soc. Am. B, vol. 11, No. 12, (Dec. 1994), pp. 2480-2491, Optical Society of America.

Weiner, A.M., "Femtosecond Optical Pulse Shaping and Processing", Prog. Quant. Electr. (1995) vol. 19, pp. 161; 230-233.

Weiner, A.M., "High-resolution femtosecond pulse shaping", J. Opt. Soc. Am. B., vol. 5, No. 8, (Aug. 1988), pp. 1563-1572, Optical Society of America.

Weiner, A.M., "Programmable femtosecond pulse shaping by use of a multielement liquid-crystal phase modulator", Optics Letters, (Mar. 15, 1990), vol. 15, No. 6, pp. 326-328, Optical Society of America.

Weiner, A.M., "Spectral holography of shaped femtosecond pulses", Optics Letters, vol. 17, No. 3 (Feb. 1, 1992), pp. 224-226, Optical Society of America.

Weiner, A.M., et al., "Femtosecond multiple-pulse impulsive stimulated Raman scattering spectroscopy", J. Opt. Soc. Am. B., vol. 8, No. 6, (Jun. 1991), pp. 1264-1275.

Weiner, Andrew M., Programmable Shaping of Femtosecond Optical Pulses by Use of 128-Element Liquid Crystal Phase Modulator, (1992) vol. 28, No. 4, pp. 908-919, IEEE Journal of Quantum Electronics.

Wu, C. et al., Mass and Photoelectron Spectrometer for Studying Field-Induced Ionization of Molecules, International Journal of Mass Spectrometry, Elsevier Science Publishers, Amsterdam, NL, vol. 216, No. 3, May 15, 2002, pp. 249-255.

Wu, Chengyin et al., Laser-Induced Dissociation and Explosion of Methane and Methanol, J. Phys. B. At. Mol. Opt. Phys; Journal of Physics B: Atomic, Molecular and Optical Physics, Jun. 14, 2002, vol. 35, No. 11, pp. 2575-2582.

Xu, C. et al.;"Two photon optical beam induced current imaging throughout backside of integrated circuits"; Appl. Phys. Lett. 71; 1997; pp. 2578-2580.

Xu, J.H., et al., "Study of Pulse Compression from 1.5 µm Distributed Feedback Lasers by a Gires-Tournois Interferometer", Fiber and Integrated Optics, vol. 13, (1994), pp. 365-372.

Yu, Huang, et al., Application of Adaptive Feedback Loop for Ultra-Violet Femtosecond Pulse Shaper Control, Optics Express Opt. Soc. America USA, vol. 14, No. 21, Oct. 2006.

Zhou, Jianping, et al., "Generation of 21-fs millijoule-energy pulses by use of Ti:sapphire", Optics Letters, vol. 19, No. 2, (Jan. 15, 1994), pp. 126-128, Optical Society of America.

Zipfel, W.R. et al; "Nonlinear magic: multiphoton microscopy in the biosciences"; Natire Biotechnology, 121 (11); Nov. 2003; pp. 1369-1377.

Baltuška, Andrius et al.; "Visible Pulse Compression to 4 fs by Optical Parametric Amplification and Programmable Dispersion Control;" Optics Letters, vol. 27, No. 5, Mar. 1, 2002; pp. 306-308.

Akozbek, N. et al.; "Continuum Generation of the Third-Harmonic Pulse Generated by an Intense Femtosecond IR Laser Pulse in Air;" Applied Physics B (Lasers and Optics), Springer-Verlag, Germany, vol. B77, No. 2-3, XP002476096; Sep. 2003, pp. 177-183.

Alexeev, I. et al., "Ultraviolet Light Generation by Intense Laser Filaments Propagating in Air," Conference on Lasers & Electro-Optics (CLEO), Baltimore, Maryland, USA, XP010876479; May 22-27, 2005, pp. 189-191.

Aviv Circular Dichroism Spectrometer, Model 400, Aviv Biomedical, Inc., http://www.avivbiomedical.com, Nov. 29, 2006; 2 pages.

Brixner, T., et al., "Adaptive Shaping of Femtosecond Polarization Profiles," J. Opt. Soc. Am. B. vol. 20, No. 5, May 2003; pp. 878-881.

Brixner, T., et al., "Femtosecond Polarlization Pulse Shaping," Optics Letters, vol. 26, No. 8, Apr. 15, 2001; pp. 557-559.

Brown, E. J. et al.; "Femtosecond Transient-Grating Techniques: Population and Coherence Dynamics Involving Ground and Excited States;" J. Chem. Phys., vol. 110, No. 12, Mar. 22, 1999; pp. 5772-5788.

Brown, E. J. et al.; "Population and Coherence Control by Three-Pulse Four-Wave Mixing;" J. Chem. Phys, vol. 111, No. 9, Sep. 1, 1999; pp. 3779-3782.

Brown, E. J. et. al. "Ultrafast Rotational Anisotropy Measurements: Unidirectional Detection;" J. Phys. Chem. A, vol. 103, No. 16, 1999 pp. 2912-2916.

Brown, E. J. et. al. "Ultrafast Rotational Anisotropy Measurements; Strong-Field Nonlinear Saturation Effects;" J. Phys. Chem. A, vol. 105, No. 34, 2001; pp. 8004-8010.

Choi, K-S et al.; "Charge Density Wave Caused by Reducing $ThSe_3$ by One Electron. Superstructure and Short-Range Order in $ATh_2Se_6$ (A=K, Rb) Studied by X-Ray Diffraction, Electron Diffraction, and Diffuse Scattering;" J. Am. Chem. Soc., vol. 120, No. 41, 1998; pp. 10706-10714.

Comstock, M. et al.; "Femtosecond Photon Echo Measurements of Electronic Coherence Relaxation Between the $X(^1E_g+)$ and $B(^3\Pi_{0u}+)$ states of $I_2$ in the Presence of He, Ar, $N_2$, $O_2$, $C_3H_8$;" J. Chem. Phys., vol. 119, No. 13, Oct. 1, 2003; pp. 6546-6553.

Comstock, M. et al.; "Rotational Wavepacket Revivals for Phase Modulation of Ultrafast Pulses;" Chemical Physics Letters, 372, 2003; pp. 739-744.

Comstock, M. et al.; "Ultrafast Laser Induced Molecular Alignment and Deformation: Experimental Evidence From Neutral Molecules and From Fragment Ions;" J. Phys. Chem. A, vol. 107, No. 40, 2003; pp. 8271-8281.

Comstock, M. et al.; "Ultrafast Transient-Grating Study of Molecules After High Intensity Excitation;" in Ultrafast Phenomena XII, 2000; 2 pages.

Dantus, Marcos et al., "Stereoisomer Recognition by MS with Shaped Laser Pulses," American Chemical Society. Abstracts of paper. At the national meeting, American Chemical Society, Washington, D.C., U.S. vol. 231 (Mar. 26, 2006) pp. 1-ANYL, XP009082814, ISSN: 0065-7727, the whole document.

Dantus, Marcos et al.; "Femtosecond Laser Observations of Molecular Vibration and Rotation;" Nature, vol. 343, Feb. 22, 1990; pp. 737-739.

Dantus, Marcos et al.; "Femtosecond Real-Time Probing of Reactions. II. The Dissociation Reaction of ICN;" J. Chem. Phys., vol. 89, No. 10, Nov. 15, 1988; pp. 6128-6140.

Dantus, Marcos et al.; "Femtosecond Real-Time Probing of Reactions. V. The reaction of IHgl;" J. Chem. Phys., vol. 91, No. 12, Dec. 15, 1989; pp. 7437-7450.

Dantus, Marcos et al.; "Real-Time Femtosecond Probing of "Transition States" in Chemical Reactions;" J. Chem. Phys., vol. 87, No. 4, Aug. 15, 1987; pp. 2395-2397.

Dantus, Marcos et al.; "Ultrafast Spectroscopy;" Encyclopedia of Applied Physics, vol. 22, 1998; pp. 431-456.

Dantus, Marcos, et al., "MIIPS characterizes and corrects femtosecond pulses," Ultrafast Optical Systems, Laser Focus World, (May 2007) XP001539450, 4 pages.

Dantus, Marcos. "Laser Control of Chemical Reactions." Chemical & Engineering News, vol. 79, 2001; p. 191.

Dantus, Marcos; "Ahmed Zewail, Nobel Laureate in Chemistry;" European Photochemistry Association (EPA) Newsletter, No. 69, Jul. 2000; 5 pages.

Dantus, Marcos; "Femtosecond Laser Pulses: Principles and Experiments;" (Book Review) J. Am. Chem. Soc., vol. 121, No. 37, 1999; pp. 8677-8678.

Dela Cruz, J. M. et al.; "Coherent Control Improves Biomedical Imaging With Ultrashort Shaped Pulses;" Journal of Photochemistry and Photobiology A: Chemistry 180, Mar. 2006; pp. 307-313.

Dela Cruz, Johanna M., et al., "Multidimensional analysis with shaped femtosecond pulses: identification of conformational and geometric isomers and mixtures using mass spectrometry," American Chemical Society. Abstracts of paper. At the national meeting, American Chemical Society, Washington, D.C., U.S., Vol. 230, (Aug. 28, 2005) p. U418, XP009082815, ISSN: 0065-7727, the whole document.

Dela Cruz, Johanna M., et al., "Quantitative mass spectrometric identification of isomers applying coherent laser control," Journal of Physical Chemistry A ACS USA, vol. 109, No. 38 (Sep. 29, 2005) pp. 8447-8450, XP002431289, ISSN: 1089-5639, figure 1.

Grimberg, B. I. et al.; "Ultrafast Nonlinear Spectroscopic Techniques in the Gas Phase and Their Density Matrix Representation;" J. Phys. Chem. A, vol. 106, No. 5, Feb. 7, 2002; pp. 697-718.

Gross, P. et al.; "Femtosecond Photoassociation: Coherence and Implications for Control in Bimolecular Reactions;" J. Chem. Phys., vol. 106, No. 19, May 15, 1997; pp. 8013-8021.

Gunaratne, T. et al.; "Influence of Bandwidth and Phase Shaping on Laser Induced Breakdown Spectroscopy With Ultrashort Laser Pulses;" Chemical Physics Letters 423, Apr. 3, 2006; pp. 197-201.

Gunn, J M et al: "Polarization and phase control of remote surface-plasmon-mediated two-photo-induced emission and waveguiding" Nano Letters American Chem. SOC. USA, vol. 6, No. 12, Aug. 2006.

Hanna, Sherif F. et al.; "Electronic-resonance-enhanced coherent anti-Stokes Raman spectroscopy of nitric oxide"; Applied Physics Letters; vol. 83, No. 9, Sep. 1, 2003; pp. 1887-1889.

Jasco Comparison Proven Spectroscopy & Chromatography Technology, J-815 Circular Dichroism Spectropolarimeter, Jasco UK, http://www.jasco.co.uk/j800.asp, Nov. 29, 2006; 2 pages.

Kosik, Ellen M., et al., "The effects of noise on ultrashort optical pulse measurement using SPIDER"; The Institute of Optics, University of Rochester, Rochester, NY; (2000) pp. 21-23.

Lim, Sang-Hyun et al.; "Single-Pulse Phase-Control Interferometric Coherent Anti-Stokes Raman Scattering Spectroscopy;" Physical Review A, 72, 2005; pp. 041803-1-041803-4.

Link, Stephan et al.; "Optical Properties and Ultrafast Dynamics of Metallic Nanocrystals;" Annu. Rev. Phys. Chem. 54, 2003; pp. 331-369.

Lozovoy, V. V. et al.: "Multiphoton Intrapulse Interference. IV. Ultrashort Laser Pulse Spectral Phase Characterization and Compensation;" Optics Letters, vol. 29, No. 7, Apr. 1, 2004; pp. 775-777.

Lozovoy, V. V. et al.; "Cascaded Free-Induction Decay Four-Wave Mixing;" Chemical Physics 266, 2001, pp. 205-212.

Lozovoy, V. V. et al.; "Femtosecond Spectrally Dispersed Three-Pulse Four-Wave Mixing: The Role of Sequence and Chirp in Controlling Intramolecular Dynamics;" J. Raman Spectroscopy 31, 2000; pp. 41-49.

Lozovoy, V. V. et al.; "Photon Echo Pulse Sequences With Femtosecond Shaped Laser Pulses As a Vehicle for Molecule-Based Quantum Computation;" J. Chemical Physics Letters 351, Jan. 10, 2002; pp. 213-221.

Lozovoy, V. V. et al.; "Spectral Phase Optimization of Femtosecond Laser Pulses for Narrow-Band, Low-Background Nonlinear Spectroscopy;" Optics Express, vol. 13, No. 26, Dec. 26, 2005; pp. 10882-10887.

Lozovoy, V. V. et al.; "Systematic Control of Nonlinear Optical Processes Using Optimally Shaped Femtosecond Pulses;" ChemPhysChem, Wiley-VCH Verlag GmbH & Co. KGaA, Weinheim, 6, 2005; pp. 1970-2000.

Lozovoy, V. V. et al.; "The Role of Microscopic and Macroscopic Coherence in Laser Control;" Chemical Physics 267, 2001; pp. 99-114.

Lozovoy, V. V. et al.; "The Role of Pulse Sequences in Controlling Ultrafast Intramolecular Dynamics With Four-Wave Mixing;" Int. Rev. In Physical Chemistry, vol. 19, No. 4, 2000; pp. 531-552.

Lozovoy, V. V., et al., "Laser Control of Physicochemical Processes; Experiments and Applications," The Royal Society of Chemistry 2006, Annu. Rep. Prog. Chem, Sect. C, 102. www.rsc.org/annrepc (2006) pp. 227-258.

Lozovoy, V.V. et al; "What Role Can Four-Wave Mixing Techniques Play in Coherent Control?;" Advances in Multiphoton Processes and Spectroscopy 14; and Quantum Control of Molecular Reaction Dynamics, edited by R.J. Gordon and Y. Fujimura, World Scientific, Singapore, 2000; pp. 62-79.

Marvet, Una et al.; "Femtosecond Concerted Elimination of Halogen Molecules From Halogenated Alkanes;" Phys. Chem. Chem. Phys., 2, 2000; pp. 885-891.

Marvet, Una et al.; "Femtosecond Dynamics of Photoinduced Molecular Detachment From Halogenated Alkanes. I. Transition State Dynamics and Product Channel Coherence;" J. Chem. Phys., vol. 109, No. 11, Sep. 15, 1998.

Marvet, Una et al.; "Femtosecond Dynamics of Unimolecular and Unrestricted Bimolecular Reactions;" J. Phys. Chem. A, vol. 102, No. 23, 1998; pp. 4111-4117.

Marvet, Una at al.; "Femtosecond Observation of a Concerted Chemical Reaction;" Chemical Physics Letters, 256, Jun. 21, 1996; pp. 57-62.

Marvet, Una et al.; "Femtosecond Photoassociation Spectroscopy: Coherent Bond Formation;" Chemical Physics Letters, 245, Nov. 3, 1995; pp. 393-399.

Pastirk, I. et al.; "2D (time-frequency) Femtosecond Four-Wave Mixing At $10^{14}$ W/cm$^2$: Molecular and Electronic Response;" Symposium on Optical Pulse and Beam Propagation III, Photonics West, 2001; 3 pages.

Pastirk, I. et al.; "Control and Characterization of Intramolecular Dynamics with Chirped Femtosecond Three-Pulse Four-Wave Mixing;" J. Phys. Chem. A, vol. 103, No. 49, Sep. 23, 1999; pp. 10226-10236.

Pastirk, I. et al.; "Femtosecond Ground State Dynamics of Gas Phase N2O4 and NO2," Chemical Physics letters, vol. 349, Nov. 23, 2001; pp. 71-78.

Pastirk, I. et al.; "Femtosecond Photo Echo and Virtual Echo Measurements of the Vibronic and Vibrational Coherence Relaxation Times of Iodine Vapor;" Chemical Physics Letters, vol. 333, Jan. 5, 2001; pp. 76-82.

Pastirk, I., et al., "Multidimensional Analytical Method Based on Binary Phase Shaping of Femtosecond Pulses," J. Phys. Chem. A, vol. 109, No. 11, Feb. 23, 2005; pp. 2413-2416.

Pastrik, I. et al., "Sequences for Controlling Laser Excitation with Femtosecond Three-Pulse Four-Wave Mixing;" The Royal Society of Chemistry, vol. 113, 1999; pp. 401-424.

Pastrik, I. et al; "Quantum Control of the Yield of a Chemical Reaction;" J. Chem. Phys., vol. 108, No. 11, Mar. 15, 1998; pp. 4375-4378.

Peng, L. W. et al.; "Stepwise Solvation of the Intramolecular-Charge-Transfer Molecule p-(Dimethylamino)benzonitrile;" J. Phys. Chem., 91, 1987, p. 6162.

PiStar Kinetic Circular Dichroism Spectrometer, http://www.phtophysics.com/pistar.php, Nov. 29, 2006; 3 pages.

QWPO-AS, Zero Order Waveplates—Air Spaced, Optical Components and Assemblies, www.cvilaser.com, published Nov. 21, 2005; pp. 8-9.

Rosker, M. J. et al.; "Femtosecond Clocking of the Chemical Bond;" Science, vol. 241, Sep. 2, 1988; pp. 1200-1202.

Rosker, M. J. et al.; "Femtosecond Real-Time Probing of Reactions. I. The Technique;" J. Chem. Phys., vol. 89, No. 10, Nov. 15, 1988; pp. 6113-6127.

Sanders, A. W. et al.: "Observation of Plasmon Propagation, Redirection, and Fan-Out in Silver Nanowires" Nano Letters, American Chemical Society, Washington, DC, US, vol. 6, No. 8, Jun. 28, 2006, pp. 1822-1826, XP007901978, ISSN: 1530-6984.

ScanMail 10K—Scanna; Internet publication from Safer America; 2003.

Stockman, Mark I. et al.; "Coherent Control of Femtosecond Energy Localization in Nanosystems;" Physical Review Letters, vol. 88, No. 6, Feb. 11, 2002; pp. 067402-1-067402-4.

Surharev, Maxim et al.; "Coherent Control Approaches to Light Guidance in the Nanoscale;" The Journal of Chemical Physics 124, 2006; XP008086379; pp. 144707-1-144707-8.

Suzuki, Takayuki et al.; "Nontrivial Polarization Shaping of Femtosecond Pulses by Reference to the Results of Dual-Channel Spectral Interferomtry;" Applied Optics, vol. 43, No. 32, Nov. 10, 2004; pp. 6047-6050.

Ting, A., et al.; "Remote Atmospheric Breakdown for Standoff Detection by Using an Intense Short Laser Pulse," Applied Optics. Opt. Soc. America, USA, vol. 44, No. 25, XP002476098, Sep. 1, 2005; pp. 5315-5320.

Waner, M. J. et al.; "Imaging the Molecular Dimensions and Oligomerization of Proteins At Liquid/Solid Interfaces;" J. Phys. Chem. B, vol. 102, No. 9, 1998; pp. 1649-1657.

Wollenhaupt, M. et al.; "Femtosecond Laser Photoelectron Spectroscopy on Atoms and Small Molecules: Prototype Studies in Quantum Control;" Annu. Rev. Phys. Chem., 56, 2005; pp. 25-56.

Xu, B et al.; "Quantitative Investigation of the Multiphoton Intrapuse Interference Phase Scan Method for Simultaneous Phase Measurement and Compensation of Femtosecond Laser Pulses;" J. Opt. Soc. Am. B, vol. 23, No. 4, Apr. 2006; pp. 750-759.

Zhang, Q. et al.; "Concerted Elimination Dynamics From Highly Excited States;" Faraday Discussions, 108, 1997; pp. 63-80.

Zhang, Q. et al.; "Femtosecond Dynamics of Photoinduced Molecular Detachment From Halogenated Alkanes. II. Asynchronous Concerted Elimination of $I_2$ From $CH_2I_2$;" J. Chem. Phys., vol. 109, No. 11, Sep. 15, 1998; pp. 4428-4442.

Delong, K.W., et al., "Frequency Resolved Optical Gating with the Use of 2nd-Harmonic Generation." Journal of Optical Society of America B-Optical Physics, 1994. 11 (11): pp. 2206-2215.

Gallmann, L., et al., "Characterization of sub-6-fs optical pulses with spectral phase interferometry for direct electric-field reconstruction," Optics Letters, vol. 24, No. 18 (Sep. 15, 1999) p. 13140-1316.

Jiang, et al. "Spectral line-by-line pulse shaping," Optics Letters, vol. 30, No. 12 (Jun. 15, 2005) Optical Society of America, pp. 1557-1559.

Midorikawa, Katsumi, et al., "Phase-Matched High-Order Harmonic Generation by Guided Intense Femtosecond Pulses," IEEE Journal of Selected Topics in Quantum Electronics, vol. 5, No. 6 (Nov./Dec. 1999) pp. 1475-1485.

Ohno, Kimihisa, et al., "Adaptive pulse shaping of phase and amplitude of an amplified femtosecond pulse laser by direct reference to frequency-resolved optical gating traces," J. Opt. Soc. Am. B vol. 19, No. 11 (Nov. 2002) pp. 2781-2790.

Posthumus, J.H., "The dynamics of small molecules in intense laser fields," Reports on Progress in Physics, 67 (2004) Institute of Physics Publishing, pp. 623-665.

Rodriguez, George, et al., "Coherent Ultrafast MI-FROG Spectroscopy of Optical Field Ionization in Molecular H2, N2, and 02," IEEE Journal on Selected Topics in Quantum Electronics, vol. 7, No. 4 (Jul./Aug. 2001) pp. 579-591.

Serbin, J., et al., "Femtosecond lasers as novel tool in dental surgery," applied surface science, 197-198 (2002) pp. 737-740.

Shimizu, Satoru, et al., "Spectral phase transfer for indirect phase control of sub-20-fs deep UV pulses," Optics Express, vol. 13, No. 17 (Aug. 22, 2005) pp. 6345-6353.

Siders, C.W., et al., "Blue-shifted third-harmonic generation and correlated self-guiding during ultrafast barrier suppression ionization of subatmospheric density noble gases," J. Opt. Soc. Am. B/vol. 13, No. 2 (Feb. 1996) pp. 330-335.

Tamaki, Y., "Phase-matched third-harmonic generation by nonlinear phase shift in a hollow fiber," Lasers and Optics Applied Physics B, vol. 67, (1998) pp. 59-63.

Verluise, Frédéric, et al., "Arbitrary dispersion control of ultrashort optical pulses with acoustic waves," J. Opt. Soc. Am. B vol. 17, No. 1 (Jan. 2000) pp. 138-145.

Weiner, A.M., "Femtosecond pulse shaping using spatial light modulators," Review Article, Review of Scientific Instruments, vol. 71, No. 5 (May 2000) pp. 1929-1960.

Dong Gun Lee et al.; "Coherent Control of High-Order Harmonics with Chirped Femtosecond Laser Pulses"; Physical Review Letters, vol. 87, No. 24, Dec. 10, 2001; pp. 243902-1-243902-4.

M. Armstrong et al.; "Versatile seven-femtosecond pulse compressor of parametrically amplified pulses using adaptive optics: studies of the primary events in protein dynamics"; Applied Physics B 74 (Suppl), 2002; pp. S127-S132.

D.S. Chemla et al; "Ultrafast phase dynamics of coherent emission from excitons in GaAs quantum wells"; Physical Review B, vol. 50, No. 12, Sep. 15, 1995; pp. 8439-8453.

Jerome Tignon et al.; "Spectral Interferometry of Semiconductor Nanostructures"; IEEE Journal of Quantum Electronics, vol. 35, No. 4; Apr. 1999; pp. 510-522.

Arthur L. Smirl et al.; "Heavy-Hole and Light-Hole Quantum Beats in the Polarization State of Coherent Emission from Quantum Wells"; IEEE Journal of Quantum Electronics, vol. 35, No. 4; Apr. 1999; pp. 523-531.

John D. Hybl et al; "Two-dimensional Fourier transform electronic spectroscopy"; Journal of Chemical Physics, vol. 115, No. 14; Oct. 8, 2001; pp. 6606-6622.

C. Iaconis et al.; "Direct measurement of the two-point field correlation function"; Optics Letters, vol. 21, No. 21; Nov. 1, 1996; pp. 1783-1785.

A.M. Weiner et al.; "Femtosecond Pulse Sequences Used for Optical Manipulation of Molecular Motion"; Reports; Mar. 16, 1990; pp. 1317-1319.

Ch. Warmuth et al.; "Studying vibrational wavepacket dynamics by measuring fluorescence interference fluctuations"; Journal of Chemical Physics, vol. 112, No. 11; Mar. 15, 2000; pp. 5060-5069.

Ch. Warmuth et al.; "Molecular quantum dynamics in a thermal system: fractional wave packet revivals probed by random-phase fluorescence interferometry"; Journal of Chemical Physics, vol. 114, No. 22; Jun. 8, 2001; pp. 9901-9910.

G.G. Paulus et al.; "Absolute-phase phenomena in photoionization with few-cycle laser pulses"; Nature, vol. 414; Nov. 8, 2001; pp. 182-184.

Yaron Silberberg; "Physics at the attosecond frontier"; Nature, vol. 414, Nov. 29, 2001; pp. 494-495.

M. Hentschel et al.; "Attosecond metrology"; Nature, vol. 414; Nov. 29, 2001; pp. 509-513.

L. Lepetit et al.; "Linear techniques of phase measurement by femtosecond spectral interferometry for applications in spectroscopy"; J. Opt. Soc. Am. B, vol. 12, No. 12; Dec. 1995; pp. 2467-2474.

L. Lepetit et al.; "Two-dimensional nonlinear optics using Fourier-transform spectral interferometry"; Optics Letters, vol. 21, No. 8; Apr. 15, 1996; pp. 564-566.

K.C. Chu et al.; "Temporal interferometric measurement of femtosecond spectral phase"; Optics Letters, vol. 21, No. 22; Nov. 15, 1996; pp. 1842-1844.

W.J. Walecki et al.; "Characterization of the polarization state of weak ultrashort coherent signals by dual-channel spectral interferometry"; Optics Letters, vol. 22, No. 2; Jan. 15, 1997; pp. 81-83.

J.P. Likforman et al.; "Measurement of photon echoes by use of femtosecond Fourier-transform Spectral Interferometry"; Optics Letters, vol. 22, No. 14; Jul. 15, 1997; pp. 1104-1106.

Michel F. Emde et al.; "Spectral interferometry as an alternative to time-domain heterodyning"; Optics Letters, vol. 22, No. 17; Sep. 1, 1997; pp. 1338-1340.

X. Chen et al.; "Temporally and spectrally resolved amplitude and phase of coherent fourwave-mixing emission from GaAs quantum wells"; Physical Review B, vol. 56, No. 15; Oct. 15, 1997; pp. 9738-9743.

Christophe Dorrer; "Influence of the calibration of the detector on spectral interferometry"; J. Opt. Soc. Am. B; vol. 16, No. 7; Jul. 1999; pp. 1160-1168.

Allison W. Albrecht et al.; "Experimental distinction between phase shifts and time delays: Implications for femtosecond spectroscopy and coherent control of chemical reactions"; Journal of Chemical Physics, vol. 111, No. 24; Dec. 22, 1999; pp. 10934-10955.

Christophe Dorrer et al.; "Spectral resolution and sampling issues in Fourier-transform spectral interferometry"; J. Opt. Soc. Am. B, vol. 17, No. 10; Oct. 2000; pp. 1795-1802.

G. Roberts; "Abstract-Interference effects in femtosecond spectroscopy"; Philosophical Transactions of the Royal Society of London Series A—Mathematical Physical and Engineering Sciences; 360 (1794): 987-1021; May 15, 2002 (1 page).

B. Chatel et al.; "Role of quadratic and cubic spectral phases in ladder climbing with ultrashort pulses"; Physical Review A 70; 2004; pp. 053414-1-053414-10.

Richard S. Judson et al.; "Teaching Lasers to Control Molecules"; Physical Review Letters, vol. 68, No. 10; Mar. 9, 1992; pp. 1500-1503.

Michael Messina et al.; "Quantum control of multidimensional systems: Implementation within the time-dependent Hartree approximation"; J. Chem Phys. 104; Jan. 1996; pp. 173-182.

D.H. Schirrmeister et al; "Femtosecond pulse dependence of dissipation in molecular systems"; Chemical Physics Letters Dec. 4, 1998; pp. 383-390.

Herschel Rabitz et al.; "Optimal Control of Molecular Motion: Design, Implementation and Inversion"; Acc. Chem. Res., vol. 33, No. 8; 2000; pp. 572-578.

R. deVivie-Riedle et al.; "Design and interpretation of laser pulses for the control of quantum systems"; Applied Physics B; 2000; pp. 285-292.

Moshe Shapiro et al.; On the Origin of Pulse Shaping Control of Molecular Dynamics; J. Phys. Chem. A, vol. 105, No. 105; 2001; pp. 2897-2902.

Y.J. Yan et al.; "Pulse shaping and coherent Raman spectroscopy in condensed phases"; J. Chem. Phys 94 (2); Jan. 15, 1991; pp. 997-1001.

Bern Kohler et al.; "Mode-Locking Matter with Light"; J. Phys. Chem 1993, 97; pp. 12602-12608.

Jeffrey L. Krause et al.; "Optical control of molecular dynamics: Molecular cannons, reflectrons and wave-packet focusers"; J. Chem. Phys. 99(9); Nov. 1, 1993; pp. 6562-6578.

V. Engel et al; "Two-photon wave-packet interferometry"; J. Chem Phys. 100 (8); Apr. 15, 1994; pp. 5448-5458.

Jeffrey L. Krause et al.; "Quantum Control of Molecular Dynamics: the Strong Response Regime"; J. Phys. Chem; 1995, 99; pp. 13736-13747.

Jianwei Che et al.; "Detection and Control of Molecular Quantum Dynamics"; J. Phys. Chem.; 1995; pp. 14949-14958.

M. Sterling et al.; "Interrogation and control of condensed phase chemical dynamics with linearly chirped pulses: 12 in solid Kr"; J. Chem. Phys. 104; May 1, 1996; pp. 6497-6506.

Jianwei Che et al.; "Semiclassical Dynamics and Quantum Control in Condensed Phases: Application to 12 in a Solid Argon Matrix"; J. Phys. Chem. 1996, 100; pp. 7873-7883.

Jianshu Cao et al.; "A simple physical picture for quantum control of wave packet localization"; J. Chem Phys., 107; Aug. 1, 1997; pp. 1441-1450.

Kenji Mishima et al.; "A theoretical study on laser control of a molecular nonadiabatic process by ultrashort chirped laser pulses"; Journal of Chemical Physics, vol. 109., No. 5; Aug. 1, 1998; pp. 1801-1809.

H.A. Kim et al.; "Expanded concept of the adiabatic population transfer using dressed states"; Physical Review A, vol. 59, No. 2; Feb. 1999; pp. 1404-1407.

Jianshu Cao et al.; "Molecular pie pulses: Population inversion with positively chirped short pulses"; Journal of Chemical Physics, vol. 113, No. 5; Aug. 1, 2000; pp. 1898-1909.

A.J. Wurzer et al.; "Highly localized vibronic wavepackets in large reactive molecules"; Applied Phys. B 71, 2000; pp. 405-409.

F. Legare et al.; "Laser pulse control of Raman processes by chirped non-adiabatic passage"; Journal of Raman Spectroscopy; 2000; pp. 15-23.

Moshe Shapiro et al.; "Coherently Controlled Asymmetric Synthesis with Achiral Light"; Physical Review Letters, vol. 84, No. 8; Feb. 21, 2000; pp. 1669-1672.

Gabriel Turinici et al.; "Quantum wavefunction controllability"; Chemical Physics 267; 2001; pp. 1-9.

M. Gruebele; "Fully quantum coherent control"; Chemical Physics 267; 2001; pp. 33-46.

V.S. Malinovsky et al.; "General theory of population transfer by adiabatic rapid passage with intense, chirped laser pulses"; The European Physical Journal D 14; 2001; pp. 147-155.

Z.W. Shen et al.; "Selective preparation of ground state wave-packets: a theoretical analysis of femtosecond pump-dump-probe experiments on the potassium dimmer"; The European Physical Journal D 14; 2001; pp. 167-172.

Sanislav S. Bychkov et al.; "Laser coherent control of molecular chiral states via entanglement of the rotational and torsional degrees of freedom"; Journal of Raman Spectroscopy; 2002; pp. 962-973.

S.E. Harris; "Control of Feshbach resonances by quantum interference"; Physical Review A66; 2002; pp. 010701-1-010701-4.

John M. Jean et al.; "Application of a multilevel Redfield theory to electron transfer in condensed phases"; J. Chem. Phys. 96; Apr. 15, 1992; pp. 5827-5842.

Bjarne Amstrup et al.; "Control of HOD photodissociation dynamics via bond-selective infrared multiphoton excitation and a femtosecond ultraviolet laser pulse"; J. Chem. Phys., vol. 97, No. 11; Dec. 1, 1992; pp. 8285-8295.

L.D. Ziegler et al.; "Nonlinear polarization description of phase-locked pulse-pair spectroscopy"; J. Chem. Phys., vol. 97, No. 7; Oct. 1, 1992; pp. 4704-4713.

S. Meyer et al.; "Photoelectron distributions from femtosecond pump/probe excitation with chirped probe pulses"; Journal of Chemical Physics, vol. 108, No. 18; pp. 7631-7636.

V.M. Akulin et al.; "Laser Control of Atomic Motion inside Diatomic Molecules"; J. Phys. Chem. A, vol. 102, No. 23; 1998; pp. 4310-4320.

Jianshu Cao et al.; "Molecular Pi Pulse for Total Inversion of Electronic State Population"; Physical Review Letters, vol. 80, No. 7; Feb. 16, 1998; pp. 1406-1409.

Moshe Shapiro et al.; "Nonadiabatic wave packet dynamics: Experiment and theory in IBr"; Journal of Chemical Physics, vol. 110, No. 5; Feb. 1, 1999; pp. 2465-2473.

Zhenwen Shen et al.; "Pump-dump control and the related transient absorption spectroscopies"; Journal of Chemical Physics, vol. 110, No. 15; Apr. 15, 1999; pp. 7192-7201.

Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756-7769.

H.S. Moon et al.; "Coherence control using the ratio of Rabi frequencies for complete coherent inversion in a four-level system"; J. Phys. B At. Mol. Phys. vol. 32; 1999; pp. 987-999.

Jeffrey A. Cina; "Nonlinear wavepacket interferometry for polyatomic molecules"; Journal of Chemical Physics, vol. 113, No. 21; Dec. 1, 2000; pp. 9488-9496.

F. Gelmukhanov et al.; "Dynamics of two-photon absorption by molecules and solutions"; J. Opt. Soc. Am. B, vol. 19, No. 5, May 2002; pp. 937-945.

Philip H. Bucksbaum; "Ultrafast control"; Nature magazine, vol. 421; Feb. 6, 2003; pp. 593-594. Kuhn & Weyn SR2 Sep. 4, 2001.

Christopher J. Bardeen et al.; "Effec of Pulse Shape on the Efficiency of Multiphoton Processes: Implications for Biological Microscopy"; Journal of Biomedical Optics, vol. 4, No. 3; Jul. 1999; pp. 362-367.

T. Hornung et al.; "Optimal control of one- and two-photon transitions with shaped femtosecond pulses and feedback"; Applied Physics B 71; 2000; pp. 277-284.

T. Brixner et al.; "Photoselective adaptive femtosecond quantum control in the liquid phase"; Nature magazine, vol. 414; Nov. 2001; pp. 57-60.

B.J. Pearson et al.; "Coherent control using adaptive learning algorithms"; Physical Review A, vol. 63; 2001; pp. 063412-1-063412-12.

Jennifer L. Herek et al.; "Quantum control of energy flow in light harvesting"; Nature magazine, vol. 417; May 30, 2002; pp. 533-535.

Nirit Dudovich et al.; "Single-pulse coherently controlled nonlinear Raman spectroscopy and microscopy"; Nature magazine, vol. 418; Aug. 1, 2002; pp. 512-514.

Dan Oron et al.; "Single-Pulse Phase-Contrast Nonlinear Raman Spectroscopy"; Physical Review Letters, vol. 89, No. 27; Dec. 30, 2002; pp. 27300-1-273001-4.

T. Brixner et al.; "Liquid-phase adaptive femtosecond quantum control: Removing intrinsic intensity dependencies"; Journal of Chemical Physics, vol. 118, No. 8; Feb. 22, 2003; pp. 3692-3701.

R. Netz et al.; "Observation of Selectivity of Coherent Population Transfer Induced by Optical Interference"; Physical Review Letters, vol. 90, No. 6; Feb. 14, 2003; pp. 063001-1-063001-4.

D.W. Schumacher et al.; "Phase Dependence of Intense Field Ionization"; Physical Review A, vol. 54, No. 5; Nov. 1996; pp. 4271-4278.

Christopher J. Bardeen et al.; "Feedback quantum control of molecular electronic population transfer"; Chemical Physics Letters 280; 1997; pp. 151-158.

Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023-13027.

Doron Meshulach et al.; "Coherent quantum control of two-photon transitions by a femtosecond laser pulse"; Nature magazine, vol. 396; Nov. 19, 1998; pp. 239-242.

A. Baltuska et al.; "Attosecond control of electronic processes by intense light fields"; Nature magazine, vol. 421; Feb. 6, 2003; pp. 611-615.

D.J. Maas et al.; "Population transfer via adiabatic passage in the rubidium quantum ladder system"; Physical Review A, vol. 59, No. 2; Feb. 1999; pp. 1374-1381.

Zohar Amitay et al.; "Phase-tailoring molecular wave packets to time shift their dynamics"; Chemical Physics 267; 2001; pp. 141-149.

T.C. Weinacht et al.; "Coherent learning control of vibrational motion in room temperature molecular gases"; Chemical Physics Letters 344; 2001; pp. 333-338.

R. van Leeuwen et al.; "Manipulation of differential electron yields via autoionizing wave-packet control"; Physical Review A, vol, 63; 2001; pp. 033403-1-033403-5.

Dan Oron et al.; "Quantum control of coherent anti-Stokes Raman processes"; Physical Review A, vol. 65; 2002; pp. 043408-1-043408-4.

Nirit Dudovich et al.; "Coherent Transient Enhancement of Optically Induced Resonant Transitions"; Physical Review Letters, vol. 88, No. 12; Mar. 25, 2002; pp. 123004-1123004-4.

Jerome Degert et al.; "Realization of a Time-Domain Fresnel Lens with Coherent Control"; Physical Review Letters, vol. 89, No. 20; Nov. 11, 2002; pp. 203003-1-203003-4.

M. Wollenhaupt et al.; "Interferences of Ultrashort Free Electron Wave Packets"; Physical Review Letters, vol. 89, No. 17; Oct. 21, 2002; pp. 173001-1-173001-4.

R. Teets et al.; "Coherent Two-Photon Excitation by Multiple Light Pulses"; Physical Review Letters, vol. 38, No. 14; Apr. 4, 1977; lags. 760-764.

R.R. Jones; "Multiphoton Ionization Enhancement Using Two Phase-Coherent Laser Pulses"; Physical Review Letters, vol. 75, No. 8; Aug. 21, 1995; pp. 1491-1494.

D.J. Maas et al.; "Vibrational ladder climbing in NO by ultrashort infrared laser pulses"; Chemical Physics Letters 270; May 16, 1997; pp. 45-49.

Christopher J. Bardeen et al.; "Quantum control of I2 in the gas phase and in condensed phase solid Kr matrix"; J. Chem. Phys., vol. 106, No. 20; May 22, 1997; pp. 8486-8503.

D.J. Maas et al.; Vibrational ladder climbing in NO by (sub)picosecond frequency-chirped infrared laser pulses; Chemical Physics Letters 290; 1998; pp. 75-80.

Vladislav V. Yakovlev et al.; "Chirped pulse enhancement of multiphoton absorption in molecular iodine"; Journal of Chemical Physics, vol. 108, No. 6, Feb. 8, 1998; pp. 2309-2313.

Radoslaw Uberna et al.; "Phase and amplitude control in the formation and detection of rotational wave packets in the E1 Eg state of Li2"; Journal of Chemical Physics, vol. 108, No. 22; pp. 9259-9274.

John M. Papanikolas et al.; "Erratum: Manipulation of rovibrational wave packet composition in the Li2 E(Eg) shelf state using intermediate state selection and shaped femtosecond laser pulses"; J. Chem Phys. 107, 4172; 1997; p. 10830.

T.C. Weinacht et al.; "Measurement of the Amplitude and Phase of a Sculpted Rydberg Wave Packet"; Physical Review Letters; vol. 80, No. 25; Jun. 22, 1998; pp. 5508-5511.

Radoslaw Uberna et al.; "Phase control of wavepacket dynamic using shape femtosecond pulses"; Faraday Discuss, vol. 113; 1999; pp. 385-400.

T.C. Weinacht et al.; "Toward Strong Field Mode-Selective Chemistry"; J. Phys. Chem. A, vol. 103, No. 49; 1999; pp. 10166-10168.

Mohamed Aziz Bouchene et al.; "Wavepacket interferometry with chirped pulses"; J. Phys. B At. Mol. Opt. Phys. 32; 1999; pp. 5167-5177.

D.J. Maas et al.; "Rotational interference in vibrational ladder climbing in NO by chirped infrared laser pulses"; Physical Review A, vol. 60, No. 2; Aug. 1999; pp. 1351-1362.

R. van Leeuwen et al.; "Coherent Control of the Energy and Angular Distribution of Autoionized Electrons"; Physical Review Letters, vol. 82, No. 14; Apr. 5, 1999; pp. 2852-2855.

Celine Nicole et al.; "Saturation of wave-packet interferences: Direct observation of spin precession in potassium atoms"; Physical Review A, vol. 60, No. 3; Sep. 1999; pp. R1755-R1758.

Mohamed Aziz Bouchene et al.; "Interplay between wave packet interferences and second harmonic generation"; Optics Communications 181; 2000; pp. 327-336.

Radoslaw Uberna et al.; "Ultrafast spectroscopy of wavelength-dependent coherent photoionization cross sections of Li2 wave packets in the E1 Eg state: The role of Rydberg states"; Journal of Chemical Physics, vol. 114, No. 23; Jun. 15, 2001; pp. 10311-10320.

Lorenzo Pesce et al.; "Quantum dynamics simulation of the ultrafast photoionization of Li2"; Journal of Chemical Physics, vol. 114, No. 3; Jan. 15, 2001; pp. 1259-1271.

M.F. DeCamp et al.; "Dynamics and coherent control of high-amplitude optical phonons in bismuth"; Physical Review B, vol. 64; 2001; pp. 092301-1-092301-3.

J. Ahn et al.; "Quantum Phase Retrieval of a Rydberg Wave Packet Using a Half-Cycle Pulse"; Physical Review Letters, vol. 86, No. 7; Feb. 12, 2001; pp. 1179-1182.

Sebastien Zamith et al.; "Observation of Coherent Transients in Ultrashort Chirped Excitation of an Undamped Two-Level System"; Physical Review Letters, vol. 87, No. 3; Jul. 16, 2001; pp. 033001-1-033001-4.

Hans U. Stauffer et al.; "Simultaneous phase control of Li2 wave packets in two electronic states"; Journal of Chemical Physics, vol. 116, No. 3; Jan. 15, 2002; pp. 946-954.

Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350-1360.

Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228-11238.

S.N. Pisharody et al.; "Phase-controlled stair-step decay of autoionizing radial wave packets"; Physical Review A, vol. 65; 2002; pp. 033418-1-033418-10.

R. Netz et al.; "Coherent population dynamics of a three-level atom in spacetime"; Physical Review A, vol. 65; pp. 043406-1-043406-12.

Joshua B. Ballard et al.; "Simultaneous control of time-dependent population transfer dynamics and wave-packet quantum interferences in Li2 by shaped ultrafast pulses"; Physical Review A 66; 2002; pp. 043402-1-043402-7.

Dan Oron et al.; "Narrow-Band Coherent Anti-Stokes Raman Signals from Broad-Band Pulses"; Physical Review Letters, vol. 88, No. 6; Feb. 11, 2002; pp. 063004-1-063004-4.

M.M. Salour et al.; "Observation of Ramsey's Interference Fringes in the Profile of Doppler-Free Two-Photon Resonances"; Physical Review Letters, vol. 38, No. 14; Apr. 4, 1977; pp. 757-760.

N.F. Scherer et al.; "Time resolved dynamics of isolated molecular systems studied with phase-locked femtosecond pulse pairs"; J. Chem Phys. vol. 93, No. 1; Jul. 1, 1990; pp. 856-857.

J.S. Melinger et al.; "Adiabatic population inversion in I2 vapor with picosecond laser pulses"; J. Chem Phys. vol. 95, No. 3; Aug. 1, 1991; pp. 2210-2213.

J.J. Gerdy et al.; "Femtosecond selective control of wave packet population"; Chemical Physics Letters, vol. 171, No. 1/2; Jul. 27, 1990; pp. 1-4.

Norbert F. Scherer et al.; "Fluorescence-detected wave packet interferometry: Time resolved molecular spectroscopy with sequences of femtosecond phase-locked pulses"; J. Chem. Phys., vol. 95, No. 3; Aug. 1, 1991; pp. 1487-1511.

N.F. Scherer et al.; "Fluorescence-detected wave packet interferometry. II. Role of rotations and determination of the susceptibility"; J. Chem. Phys., vol. 96, No. 6; Mar. 15, 1992; pp. 4180-4194.

L.D. Noordam et al.; "Redistribution of Rydberg States by Intense Picosecond Pulses"; Physical Review Letters, vol. 68, No. 10; Mar. 9, 1992; pp. 1496-1499.

J.S. Melinger et al.; "Generation of Narrowband Inversion with Broadband Laser Pulses"; vol. 68, No. 13; Mar. 30, 1992; pp. 2000-2003.

B. Broers et al.; "Efficient Population Transfer in a Three-Level Ladder System by Frequency-Swept Ultrashort Laser Pulses"; Physical Review Letters, vol. 69, No. 14; Oct. 5, 1992; pp. 2062-2065.

R.R. Jones et al.; "Ramsey Interference in Strongly Driven Rydberg Systems"; Physical Review Letters, vol. 71, No. 16; Oct. 18, 1993; pp. 2575-2578.

J.F. Christian et al.; "Rubidium electronic wavepackets probed by a phase-sensitive pump-probe technique"; Optics Communications, vol. 103, No. 1/2; Nov. 1, 1993; pp. 79-84.

J.S. Melinger et al.; "Adiabatic population transfer with frequency-swept laser pulses"; J. Chem. Phys. vol. 101, No. 8; Oct. 15, 1994; pp. 6439-6454.

P. Balling et al.; "Interference in climbing a quantum ladder system with frequency-chirped laser pulses"; Physical Review A, vol. 50, No. 5; Nov. 1994; pp. 4276-4285.

D.W. Schumacher et al.; "Phase Dependence of Intense Field Ionization: A Study Using Two Colors"; Physical Review Letters, vol. 73, No. 10; Sep. 5, 1994; pp. 1344-1347.

L. Marmet et al.; "Observation of Quasi-Landau Wave Packets"; Physical Review Letters, vol. 72, No. 24; Jun. 13, 1994; pp. 3779-3782.

Valerie Blanchet et al.; "One-color coherent control in Cs2 Observation of 2.7 fs beats in the ionization signal"; Chemical Physics Letters, vol. 233; Feb. 25, 1995; pp. 491-499.

R.R. Jones et al.; "Bound-state interferometry using incoherent light"; J. Phys. B 28 At. Mol. Opt. Phys.; 1995; pp. L405-L411.

D.W. Schumacher et al.; "Programmable cesium Rydberg wave packets"; Physical Review A, vol. 52, No. 6; Dec. 1995; pp. 4719-4726.

R.R. Jones; "Interference Effects in the Multiphoton Ionization of Sodium"; Physical Review Letters, vol. 74, No. 7; Feb. 13, 1995; pp. 1091-1094.

Bern Kohler et al.; "Quantum Control of Wave Packet Evolution with Tailored Femtosecond Pulses"; Physical Review Letters, vol. 74, No. 17; Apr. 24, 1995; pp. 3360-3363.

M. Ovchinnikov et al.; "Quantum interference in resonant Raman spectra of 12 in condensed media"; J. Chem. Phys., vol. 106, No. 13; Apr. 1, 1997; pp. 5775-5778.

Richard M. Williams et al.; "Compositional control of rovibrational wave packets in the E(1 Eg) "shelf" state of Li2 via quantum-state-resolved intermediate state selection"; J. Chem. Phys. vol. 106, No. 20; May 22, 1997; pp. 8310-8323.

John M. Papanikolas et al.; "Manipulation of rovibrational wave packet composition in the Li2 E(1Eg) shelf state using intermediate state selection and shaped femtosecond laser pulses"; J. Chem. Phys., vol. 107, No. 11; Sep. 15, 1997; pp. 4172-4178.

Valerie Blanchet et al.; "Temporal Coherent Control in Two-Photon Transitions: From Optical Interferences to Quantum Interferences"; Physical Review Letters, vol. 78, No. 14; Apr. 7, 1997; pp. 2716-2719.

R. Zadoyan et al.; "Wavepacket diagnosis with chirped probe pulses"; Chemical Physics, vol. 233; 1998; pp. 353-363.

M.A. Bouchene et al.; "Temporal coherent control induced by wave packet interferences in one and two photon atomic transitions"; The European Physical Journal D, vol. 2; 1998; pp. 131-141.

Valerie Blanchet et al.; "Temporal coherent control in the photoionization of Cs2: Theory and experiment"; Journal of Chemical Physics, vol. 108, No. 12; Mar. 22, 1998; pp. 4862-4876.

R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.

T. Brixner et al.; "Abstract-Femtosecond quantum control"; Advances in Atomic, Molecular, and Optical Physics, vol. 46; 46:1-54; 2001 (1 page).

T. Brixner et al.; "Abstract-Photoselective adaptive femtosecond quantum control in the liquid phase"; NATURE; 414 (6859): 57-60; Nov. 1, 2001 (1 page).

B. Dayan et al.; "Coherent control with broadband squeezed vacuum"; arXiv:quant-ph/0302038 v1; Feb. 5, 2003 (4 pages).

B. Dayan et al.; "Two Photon Absorption and Coherent Control with Broadband Down-Converted Light"; Physical Review Letters, vol. 93, No. 2; Jul. 9, 2004; pp. 023005-1-023005-4.

B. Dayan et al.; "Nonlinear Interactions with an Ultrahigh Flux of Broadband Entangled Photons"; Physical Review Letters, PRL 94; Feb. 4, 2005, 2004; pp. 043602-1-043602-4.

N. Dudovich et al.; "Single-pulse coherent anti-Stokes Raman spectroscopy in the fingerprint spectral region"; J. of Chem. Phys., vol. 118, No. 20; May 22, 2003; pp. 9208-9215.

D. Oron et al.,; "Femtosecond Phase-and-Polariation Control for Background-Free Coherent Anti-Stokes Raman Spectroscopy"; Physical Review Letters, vol. 90, No. 91; May 30, 2003; pp. 213902-1-213902-4.

N. Dudovich et al.; "Quantum Control of the Angular Momentum Distribution in Multiphoton Absorption Processes"; Physical Review Letters, vol. 93, No. 10; Mar. 12, 2004; pp. 103003-1-103003-4.

D. Oron et al.,; "All-optical processing in coherent nonlinear spectroscopy"; Physical Review A 70; 2004; pp. 023415-1-023415-4.

J.G. Underwood et al.,; "Switched Wave Packets: A Route to Nonperturbative Quantum Control"; Physical Review Letters, vol. 90, No. 22; Jun. 6, 2003; pp. 223001-1-223001-4.

M. Renard et al.; "Controlling ground-state rotational dynamics of molecules by shaped femtosecond laser pulses"; Physical Review A 69; 2004; 043401-1-043401-6.

A. Powe et al.; "Molecular Fluorescence, Phosphorescence, and Chemiluminescence Spectrometry"; Anal. Chem., vol. 76, No. 15; Aug. 15, 2004; pp. 4614-4634.

D. Abramavicius et al.; "Disentangling multidimensional femtosecond spectra of excitons by pulse shaping with coherent control"; J. of Chem. Phys., vol. 120, No. 18; May 8, 2004; pp. 8373-8378.

M.C. Chen et al.; "Coherent control multiphoton processes in semiconductor saturable Bragg reflector with freezing phase algorithm"; Appl. Phys. B 80; 2005; pp. 333-340.

W. Wohlleben et al.; "Coherent Control for Spectroscopy and Manipulation of Biological Dynamics"; Chem. Phys. Chem., 6; 2005; pp. 850-857.

T. Okada et al.; "Optical control of two-photon excitation efficiency of α-perylene crystal by pulse shaping"; Amer. Inst. of Phys., vol. 121, No. 13; Oct. 1, 2004; pp. 6386-6391.

V. Prokhorenko et al.; "Coherent control of the population transfer in complex sovated molecules at weak excitation. An experimental study"; The J. of Chem. Phys., 122; 2005; 184502-1-184502-11.

A. Prakelt et al.; "Phase control of two-photon transition with shaped femtosecond laser-pulse sequences"; Physical Review A 70; 2004; pp. 063407-1-06407-10.

B.J. Pearson et al.; "Control of Raman Lasing in the Nonimpulsive Regime"; Physical Review Letters, vol. 92, No. 24; Jun. 18, 2004; pp. 243003-1-243003-4.

Derryck T. Reid; "Algorithm for Complete and Rapid Retrieval of Ultrashort Pulse Amplitude and Phase from a Sonogram"; IEEE Journal of Quantum Electronics; vol. 35, No. 11, Nov. 1999; pp. 1584-1589.

I.G. Cormack et al.; "Rapid measurement of ultrashort-pulse amplitude and phase from a two-photon absorption sonogram trace"; J. Opt. Soc. Am. B; vol. 18, No. 9, Sep. 2001; pp. 1377-1382.

E. Tokunaga et al.; "Frequency-domain interferometer for femtosecond time-resolved phase spectroscopy"; Optics Letters, vol. 17, No. 16; Aug. 15, 1992, pp. 1131-1133.

Victor Wong et al.; "Analysis of ultrashort pulse-shape measurement using linear interferometers"; Optics Letters, vol. 19, No. 4; Feb. 15, 1994; pp. 287-289.

Victor Wong et al.; "Linear filter analysis of methods for ultrashort-pulse-shape measurements"; J. Opt.Soc. Am. B, vol. 12, No. 8; Aug. 1995; pp. 1491-1499.

David M. Jonas et al.; "Femtosecond Wavepacket Spectroscopy: Influence of Temperature, Wavelength and Pulse Duration"; J. Phys. Chem.; 1995; pp. 2594-2608.

J. Peatross et al.; "Temporal decorrelation of short laser pulses"; J. Opt. Soc. Am. B, vol. 15, No. 1; Jan. 1998; pp. 216-222.

McGraw-Hill Encyclopedia of Science & Technology, 6th Ed.; "Mass spectrometry"; 1987; pp. 492-502 (12 pages).

Ocean Optics Inc.; "HR4000 High-resolution Spectrometer" http://oceanoptics.com/products/hr4000.asp; Jun. 25, 2005 (p. 1 of 4-p. 4 of 4).

Ocean Optics Inc.; "USB2000 Miniature Fiber Optic Spectrometer" http://oceanoptics.com/products/usb2000.asp; Jun. 25, 2005 (p. 1 of 7-p. 6 of 7).

Ocean Optics Inc.; "S2000 Miniature Fiber Optic Spectrometer" http://oceanoptics.com/products/s2000.asp; Jun. 25, 2005 (p. 1 of 4-p. 4 of 4).

M. Schurenberg et al.; "Abstract-Laser desorption/ionization mass spectrometry of peptides and proteins with particle suspension matrixes"; Analytical Chemistry; 71 (1): 221-229; Jan. 1, 1999 (1 page).

F. Hillenkamp et al.;"Abstract-Matrix-assisted laser desorption/ionisation, an experience"; International Journal of Mass Spectrometry; 200 (1-3): 71-77; Dec. 25, 2000 (1 page).

M.O. Scully, et al.; "Fast Cars: Engineering a laser spectroscopic technique for rapid identification of bacterial spores"; PNAS; vol. 99, No. 17; Aug. 20, 2002; pp. 10994-11001.

K.D. Belfield et al.; "Multiphoton-absorbing organic materials for microfabrication, emerging optical applications and non-destructive three-dimensional imaging"; J. of Phys. Organic Chem., 13; 2000; pp. 837-849.

B. Natarajan et al.; "Abstract-Innovative pulse shaping for high-performance wireless TDMA"; IEEE Communications Letters; 5 (9): 372-374; Sep. 2001 (1 page).

A. Pe're et al.; Optical Code-Division Multiple Access Using Broad-Band Parametrically Generated Light; J. of Lightwave Tech.; vol. 22, No. 6; Jun. 2004; pp. 1463-1471.

J.J. Garcia-Ripoll et al.; "Speed Optimized Two-Qubit Gates with Laser Coherent Control Techniques for Ion Trap Quantum Computing"; Physical Review Letters, vol. 91, No. 15; Otober 10, 2003; pp. 157901-1-157901-4.

J. Ahn et al.; "Information Storage and Retrieval Through Quantum Phase"; Science Magazine, vol. 287; Jan. 21, 2000; pp. 463-465.

Greg Taft et al.; "Measurement of 10-fs Laser Pulses"; IEEE Journal of Selected Topics in Quantum Electronics, vol. 2, No. 3, Sep. 1996; pp. 575-585.

Daniel J. Kane et al.; "Simultaneous measurement of two ultrashort laser pulses from a single spectrogram in a single shot"; Optical Society of America; vol. 14, No. 4, Apr. 1997; pp. 935-943.

Peter J. Delfyett et al.; "Joint Time-Frequency Meaurements of Mode-Locked Semiconductor Diode Lasers and Dynamics Using Frequency-Resolved Optical Gating"; IEEE Journal of Quantum Electronics, vol. 35, No. 4, Apr. 1999; pp. 487-500.

David N. Fittinghoff et al.; "Frequency-Resolved Optical Gating Measurement of Ultrashort Pulses Passing Through a High Numerical Aperture Objective"; IEEE Journal of Quantum Electronics, vol. 35, No. 4, Apr. 1999; pp. 479-486.

Andrius Baltuska et al.; "Second-Harmonic Generation Frequency-Resolved Optical Gating in the Single-Cycle Regime"; IEEE Journal of Quantum Electronics, vol. 35, No. 4, Apr. 1999; pp. 459-478.

Hilary K. Eaton et al.; "Investigating Nonlinear Femtosecond Pulse Propagation with Frequency-Resolved Optical Gating"; IEEE Journal of Quantum Electronics, vol. 35, No. 4, Apr. 1999; pp. 451-458.

Craig W. Siders et al.; "Multipulse Interferometric Frequency-Resolved Optical Gating"; IEEE Journal of Quantum Electronics, vol. 35, No. 4, Apr. 1999; pp. 432-440.

Atsushi Yabushita et al.; "SHG FROG and XFROG methods for phase/intensity characterization of pulses propagated through an absorptive optical medium"; Optics Communications; Oct. 15, 2001; pp. 227-232.

Roger G.M.P. Koumans et al.; "Time-Resolved Optical Gating Based on Dispersive Propagation: A New Method to Characterize Optical Pulses"; IEEE Journal of Quantum Electronics, vol. 36, No. 2, Feb. 2000; pp. 137-144.

Daniel J. Kane et al.; "Convergence test for inversion of frequency-resolved optical gating spectrograms"; Optics Letters, vol. 25, No. 16, Aug. 15, 2000; pp. 1216-1218.

Julie A. Gruetzmacher et al.; "Time and Frequency-Gated FID: a New Approach to Study the Vibrational Dephasing of Water"; Ultrafast Phenomena XII, 66; pp. 530-532.

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228-1235.

David N. Fittinghoff et al.; "Noise sensitivity in frequency-resolved optical-gating measurements of ultrashort pulses"; J. Opt. Soc. Am. B, vol. 12, No. 10, Oct. 1995; pp. 1955-1967.

Noriaki Tsurumachi et al.; "Interferometric observation of femtosecond free induction decay"; Optics Letters, vol. 19, No. 22, Nov. 15, 1994; pp. 1867-1869.

C. Dorrer et al.; "Characterization of chirped-pulse amplification systems with spectral phase interferometry for direct electric-field reconstruction"; Applied Physics B 70 (Suppl.), 2000; pp. S77-S84.

C. Radzewicz et al.; "A poor man's FROG"; Optics Communications, Dec. 15, 2000; pp. 329-333.

C. Dorrer et al.; "Spatio-temporal characterization of the electric field of ultrashort optical pulses using two-dimensional shearing interferometry"; Applied Physics B74 (Suppl.), 2002; pp. S209-S217.

K.H. Hong et al.; "Time-frequency analysis of chirped femtosecond pulses using Wigner distribution function"; Applied Physics B74 (Suppl), 2002; pp. S231-S236.

Christophe Dorrer et al.; "Accuracy criterion for ultrashort pulse characterization techniques: application to spectral phase interferometry for direct electric field reconstruction"; Appl. Phys. B 74, vol. 19, No. 5, May 2002 ; pp. 1019-1029.

Kazunori Naganuma et al; "General Method for Ultrashort Light Pulse Chirp Measurement"; IEEE Journal of Quantum Electronics, vol. 25, No. 5; Jun. 1989; pp. 1225-1233.

Y. Ding et al.; "Time-Domain Image Processing Using Dynamic Holography"; IEEE Journal of Selected Topics in Quantum Electronics, vol. 4, No. 2; Mar./Apr. 1998; pp. 332-341.

Chris Iaconis et al; "Self-Referencing Spectral Interferometry for Measuring Ultrashort Optical Pulses"; IEEE Journal of Quantum Electronics, vol. 35, No. 4; Apr. 1999; pp. 501-509.

Jung-Ho Chung et al.; "Ambiguity of Ultrashort Pulse Shapes Retrieved From the Intensity Autocorrelation and the Power Spectrum"; IEEE Journal on Selected Topics of Quantum Electronics, vol. 7, No. 4; Jul./Aug. 2001; pp. 656-666.

V. Kabelka et al.; "Time-frequency imaging of a single ultrashort light pulse from anularly resolved autocorrelation"; Optics Letters, vol. 20, No. 1; Jun. 1, 1995; pp. 1301-1303.

Paul R. Bolton et al.; "Propagation of intense, ultrashort laser pulses through metal vapor: refraction-limited behavior for single pulses"; J. Opt. Soc. Am. B, vol. 13, No. 2; Feb. 1996; pp. 336-346.

June-Koo Rhee et al.; "Real-time dispersion analyzer of femtosecond laser pulses with use of a spectrally and temporally resolved upconversion technique"; J. Opt. Soc. Am. B, vol. 13, No. 8; Aug. 1996; pp. 1780-1785.

Marco A. Krumbugel et al.; "Direct ultrashort-pulse intensity and phase retrieval by frequency-resolved optical gating and a computational neural network"; Optics Letters, vol. 21, No. 2; Jan. 15, 1996; pp. 143-145.

David N. Fittinghoff et al.; "Measurement of the intensity and phase of ultraweak, ultrashort laser pulses"; Optics Letters, vol. 21, No. 12; Jun. 15, 1996; pp. 884-886.

T. Feurer et al.; "Measuring the temporal intensity of ultrashort laser pulses by triple correlation"; Appl. Phys. B; 1998; pp. 163-168.

Alfred Kwok et al.; "Frequency-Resolved Optical Gating Using Cascaded Second-Order Nonlinearities"; Journal of Selected Topics in Quantum Electronics, vol. 4, No. 2; Mar./Apr. 1998; pp. 271-277.

Daniel J. Kane; "Real-Time Measurement of Ultrashort Laser Pulse Using Principal Component Generalized Projection"; IEEE Journal of Selected Topics in Quantum Electronics; vol. 4, No. 2; Mar./Apr. 1998; pp. 278-284.

Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306-316.

Michael J. Stimson et al.; "Noisy-light correlation functions by frequency resolved optical gating"; J. Opt. Soc. Am. B, vol. 15, No. 2; Feb. 1998; pp. 505-514.

J. W. Nicholson et al.; "Full-field characterization of femtosecond pulses by spectrum and cross-correlation measurements"; Optics Letters, vol. 24, No. 23; Dec. 1, 1999; pp. 1774-1776.

F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674-1676.

Tzu-Ming Liu et al.; "Triple-optical autocorrelation for direct optical pulse-shape measurement"; Applied Physics Letters, vol. 81, No. 8; Aug. 19, 2002; pp. 1402-1404.

Yoshihiro Takagi et al.; "Multiple- and single-shot autocorrelator based on two-photon conductivity in semiconductors"; Optics Letters, vol. 17, No. 9; May 1, 1992; pp. 658-660.

Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388-3391.

A.N. Naumov et al.; "Frequency-time and time-space mappings for single-shot coherent four-wave mixing with chirped pulses and broad beams"; Journal of Raman Spectroscopy, 2001; pp. 960-970.

E.T.J. Nibbering et al.; "Spectral determination of the amplitude and the phase of intense ultrashort optical pulses"; J. Opt. Soc. Am. B, vol. 13, No. 2; Feb. 1996; pp. 317-329.

Victor Wong et al.; "Ultrashort-pulse characterization from dynamic spectrograms by iterative phase retrieval"; J. Opt. Soc. Am. B, vol. 14, No. 4; Apr. 1997; pp. 944-949.

Sarah M. Gallagher et al.; "Heterodyne detection of the complete electric field of femtosecond four-wave mixing signals"; J. Opt. Soc. Am. B, vol. 15, No. 8; Aug. 1998; pp. 2338-2345.

C. Dorrer et al.; "Single-shot real-time characterization of chirped-pulse amplification systems by spectral phase interferometry for direct electric-field reconstruction"; Optics Letters, vol. 24, No. 22; Nov. 15, 1999; pp. 1644-1646.

C. Dorrer; "Implementation of spectral phase interferometry for direct electric-field reconstruction with a simultaneously recorded reference interferogram"; Optics Letters, vol. 24, No. 21; Nov. 1, 1999; pp. 1532-1534.

C.Y. Chien et al.; "Single-shot chirped-pulse spectral interferometry used to measure the femtosecond ionization dynamics of air"; Optics Letters, vol. 25, No. 8; Apr. 15, 2000; pp. 578-580.

J.W. Nicholson et al.; "Unbalanced third-order correlations for full characterization of femtosecond pulses"; Optics Letters, vol. 25, No. 24; Dec. 15, 2000; pp. 1801-1803.

Sergey Yeremenko et al.; "Frequency-resolved pump-probe characterization of femtosecond infrared pulses"; Optics Letters, vol. 27, No. 13; Jul. 1, 2002; pp. 1171-1173.

J. M. Dudley, et al.; "Direct measurement of pusle distortion near the zero-disperson wavelength in an optical fiber by frequency-resolved optical gating"; Optics Letters, vol. 22, No. 7; Apr. 1, 1997; 457-459.

M.C. Chen et al.; "Freezing phase scheme for fast adaptive control and its application to characterization of femtosecond coherent optical pulses reflected from semiconductor saturable absorber mirrors"; J. Opt. Soc. Am. B, vol. 22, No. 5; May 2005; pp. 1134-1142.

I. Amat-Roldan et al.; "Measurement of electric field by interferometric spectral trace observation"; Optics Letters, vol. 30, No. 9; May 1, 2005; pp. 1063-1065.

I. Amat-Roldan et al.; "Starch-based second-harmonic-generated colinear frequency-resolved optical gating pulse characterization at the focal plane of a high-numerical-aperture lens"; Optics Letters, vol. 29, No. 19; Oct. 1, 2004; pp. 2282-2284.

Gregory D. Goodno et al.; "Ultrafast heterodyne-detected transient-grating spectroscopy using diffractive optics"; Optical Society of America, vol. 15, No. 6, Jun. 1998; pp. 1791-1794.

L. Misoguti et al.; "Generation of Broadband VUV Light Using Third-Order Cascaded Processes"; Physical Review Letters, vol. 87, No. 1, Jul. 2, 2001; pp. 013601-1-013601-4.

D. Zeidler et al.; "Amplification of tailored white-light continuum"; Applied Physics, B74 (Suppl), 2002; pp. S51-S56.

T. Brixner et al.; "Generation and characterization of polarization-shaped femtosecond laser pulses"; Applied Physics B74 (Suppl), 2002; pp. S133-S144.

Jeffrey L. Krause et al.; "Creating and Detecting Shaped Rydberg Wave Packets"; Physical Review Letters, vol. 79, No. 25; Dec. 22, 1997; pp. 4978-4981.

S. Backus et al.; "16-fs, 1-µ J ultraviolet pulses generated by third-harmonic conversion in air"; Optics Letters, vol. 21, No. 9; May 1, 1996; pp. 665-667.

Julie A. Gruetzmacher et al.; "Few-cycle mid-infrared pulse generation, characterization and coherent propagation in optically dense media"; Review of Scientific Instruments, vol. 73, No. 6; Jun. 2002; pp. 2227-2236.

T. Kobayashi et al.; "Tunable visible and near-infrared pulse generator in a 5 fs regime"; Appl. Phys. B 70 (Suppl); 2000; pp. S239-S246.

A. Poppe et al; "Few-cycle optical waveform synthesis"; Applied Physics B 72; 2001; pp. 373-376.

Peifang Tian et al.; "Ultrafast measurement of two-photon absorption by loss modulation"; Optics Letters, vol. 27, No. 18; Sep. 15, 2002; pp. 1634-1636.

M. Hentschel et al.; "Generation of 0.1-TW optical pulses with a single-stage Ti:sapphire amplifier at a 1-kHz repetition rate"; Appl. Phys. B 70 [Suppl.]; 2000; pp. S161-S164.

Photogen Technologies, Inc., "Photogen-Technology"; www.photogen.com/body/tech_body.html; Dec. 20, 2001 (19 pages).

W.M. Sharman et al.; "Photodynamic therapeutics: basic principles and clinical applications"; DDT, vol. 4, No. 11; Nov. 1991; pp. 507-517.

Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649-4656.

J.P. Ogilvie et al.; "Fourier transform measurement of two-photon excitation spectra: applications to microscopy and optimal control"; Optics Letters, vol. 30, No. 8; Apr. 15, 2005; pp. 911-913.

D. Lalovic et al.; "Quantum mechanics in terms of non-negative smoothed Wigner functions"; Physical Review A, vol. 46, No. 3; Aug. 1, 1992; pp. 1206-1212.

Christopher J. Bardeen et al.; "Using time-dependent rate equations to describe chirped pulse excitation in condensed phases"; Chemical Physics Letters 302; 1999; pp. 405-410.

Yu-Chen Shen et al.; "What can short-pulse pump-probe spectroscopy tell us about Franck-Condon dynamics?"; Journal of Chemical Physics, vol. 110. No. 20; May 22, 1999; pp. 9793-9806.

M. Ovchinnikov et al.; "Semiclassical molecular dynamics computation of spontaneous light emission in the condensed phase: Resonance Raman spectra"; Journal of Chemical Physics, vol. 114, No. 16; Apr. 22, 2001; pp. 7130-7143.

S. Yeremenko et al.; "The criterion of pulse reconstruction quality based on Wigner representation"; Applied Physics B 70 (Suppl); 2000; pp. S109-S117.

David C. Clary; "Quantum Theory of Chemical Reaction Dynamics"; Science, vol. 279, Mar. 20 1998; p. 1879.

B.D. Fainberg; "Diagram Technique for Nonlinear Optical Spectroscopy in the Fast Electronic Dephasing Limit "; Journal of the Chinese Chemical Society, 47; 2000; pp. 579-582.

Chantal Daniel et al.; "Deciphering the Reaction Dynamics Underlying Optimal Control Laser Fields"; Science Magazine, vol. 299; Jan. 24, 2003; pp. 536-539.

T. Witte et al.; "Controlling molecular ground-state dissociation by optimizing vibrational ladder climbing"; Journal of Chemical Physics, vol. 118, No. 5; Feb. 1, 2003; p. 2021-2024.

R.J. Levis et al.; "Closing the Loop on Bond Selective Chemistry Using Tailored Strong Field Laser Pulses"; the Journal of Physical Chemistry, vol. 106, No. 27; Jul. 11, 2002; pp. 6427-6444.

Mustafa Demirplak et al.; "Optical control of molecular dynamics in a liquid"; Journal of Chemical Physics, vol. 116, No. 18; May 8, 2002; pp. 8028-8035.

M. Bergt et al.; "Time-resolved organometallic photochemistry Femtosecond fragmentation and adaptive control of CpFe(CO)2X (X=C1,Br,1)"; Journal of Organometallic Chemistry 661; 2002; pp. 199-209.

Ben R. Torralva et al; "Mechanisms for laser control of chemical reactions"; Journal of Modern Optics, vol. 49, No. 3/4; 2002; pp. 593-625.

N.H. Damrauer et al.; "Control of bond-selective photochemistry in CH2BrCI using adaptive femtosecond pulse shaping"; The European Physical Journal D, 20, 2002; pp. 71-76.

L. Windhorn et al.; "Molecular dissociation by mid-IR femtosecond pulses"; Chemical Physics Letters 357, May 3, 2002; pp. 85-90.

Robert J. Levis et al.; "Selective Bond Dissociation and Rearrangement with Optimally Tailored, Strong-Field Laser Pulses"; Science Magazine, vol. 292; Apr. 27, 2001; pp. 709-713.

T. Brixner et al.; "Problem complexity in femtosecond quantum control"; Chemical Physics 267; 2001; pp. 241-246.

O.M. Sarkisov et al.; "Control of elementary chemical reactions by femtosecond light pulses"; Quantum Electronics, vol. 31, No. 6; 2001; pp. 483-488.

Julie A. Mueller et al.; "Competing isomeric product channels in the 193 nm photodissociation of 2-chioropropene and in the unimolecular dissociation of the 2-propenyl radical"; Journal of Chemical Physics, vol. 114, No. 10; Mar. 8, 2001; pp. 4505-4521.

Chantal Daniel et al.; "Analysis and control of laser induced fragmentation processes in CpMn(CO)3"; Chemical Physics 267; 2001; pp. 247-260.

A. Glass et al.; "Control of the photodissociation of CsCI"; Applied Physics B 71; 2000; pp. 267-276.

T. Frohnmeyer et al.; "Femtosecond pump-probe photoelectron spectroscopy on Na2: a tool to study basic coherent control schemes"; Applied Physics B 71; 2000; pp. 259-266.

M. Bergt et al.; "Controlling the Femtochemistry of Fe(CO)5"; J. Phys. Chem. A, vol. 103, No. 49; 1999; pp. 10381-10387.

A. Assion et al.; "Coherent control by a single phase shaped femtosecond laser pulse"; Chemical Physics Letters 259; Sep. 13, 1996; pp. 488-494.

Langchi Zhu et al.; "Coherent Laser Control of the Product Distribution Obtained in the Photoexcitation of HI"; Science Magazine, vol. 270; Oct. 6, 1995; pp. 77-80.

Yu-hui Chiu et al.; "Vibrational mode effects, scattering dynamics and energy disposal in reaction of C2H2 with methane"; J. Chem. Phys., vol. 102, No. 3; Jan. 15, 1995; pp. 1199-1216.

J.S. Keller et al.; "Selective bond fission in methyl mercaptan at 193 nm via radial derivative coupling between the 21A" and 11A" adiabatic electronic states"; J. Chem. Phys. vol. 96, No. 6; Mar. 15, 1992; pp. 4324-4329.

I. Bar et al.; "Mode-selective bond fission: Comparison between the photodissociation of HOD (0,0,1) and HOD (1,0,0)"; J. Chem. Phys. vol. 95, No. 5; Sep. 1, 1991; pp. 3341-3346.

Michael J. Bronikowski et al.; "Bond-specific chemistry: OD:OH product ratios for the reactions H+HOD(100) and H+HOD(001)"; J. Chem. Phys., vol. 95, No. 11; Dec. 1, 1991; pp. 8647-8648.

I. Bar et al.; "Direct observation of preferential bond fission by excitation of a vibrational fundamental: Photodissociation of HOD (0,0,1)"; J. Chem. Phys., vol. 93, No. 3; Aug. 1, 1990; pp. 2146-2148.

R.L. VanderWal et al.; "Selectively breaking the O-H bond in HOD"; J. Chem. Phys., vol. 92, No. 1; Jan. 1, 1990; pp. 803-805.

Neil Shafer et al.; "Isotope effect in the photodissociation of HDO at 157.5 nm"; J. Chem. Phys., vol. 90, No. 11; Jun. 1, 1989; pp. 6807-6808.

L.J. Butler et al.; "The electronic state-selective photodissociation of CH2BrI at 248, 210 and 193 nm"; J. Chem. Phys. vol. 86, No. 4; Feb. 15, 1997; pp. 2051-2074.

L.J. Butler et al.; "Bond selective photochemistry in CH2BrI through electronic excitation at 210 nm"; J. Chem. Phys., vol. 84, No. 7; Apr. 1, 1986; pp. 4104-4106.

David J. Tannor et al.; "Control of selectivity of chemical reaction via control of wave packet evolution"; J. Chem. Phys., vol. 83, No. 10; Nov. 15, 1985; pp. 5013-5018.

Christopher J. Bardeen et al.; "Quantum Control of NaI Photodissociation Reaction Product States by Ultrafast Tailored Light Pulses"; J. Phys. Chem. A, vol. 101, No. 20; 1997; pp. 3815-3822.

V.A. Apkarian; 'Comment on "Time-resolved laser induced harpoon reactions"'; J. Chem. Phys. vol. 106, No. 12; Mar. 22, 1997; pp. 5298-5299.

R.B. Vrijen et al.; "Limitations on quantum ladder climbing in complex systems"; Physical Review A, vol. 56, No. 3; Sep. 1997; pp. 2205-2212.

Lutfur R. Khundkar et al.; "Ultrafast Molecular Reaction Dynamics in Real-Time: Progress Over a Decade"; Annu. Rev. Phys. Chem., 1990; pp. 15-60.

Stuart A. Rice; "Optical control of reactions"; Nature magazine, vol. 403; Feb. 3, 2000; pp. 496-497.

Richard N. Zare; "Laser Control of Chemical Reactions"; Science magazine, vol. 279; Mar. 20, 1998; pp. 1875-1879.

Stuart A. Rice; "Active Control of Molecular Dynamics: Coherence versus Chaos"; Journal of Statistical Physics, vol. 101, Nos. 1/2; 2000; pp. 187-212.

Herschel Rabitz et al.; "Whither the Future of Controlling Quantum Phenomena?"; Science magazine, vol. 288; May 5, 2000; pp. 824-828.

Yuri T. Mazurenko; "Spectral Holography and Spectral Nonlinear Optics of Ultrashort Pulses"; Journal of the Chinese Chemical Society, vol. 47, No. 4A; 2000; pp. 679-683.

Marcos Dantus; "Coherent Nonlinear Spectroscopy: From Femtosecond Dynamics to Control"; Annu. Rev. Phys. Chem. 2001; pp. 639-679, C1-C7.

Stuart A. Rice; "Interfering for the good of a chemical reaction"; Nature magazine; vol. 409; Jan. 18, 2001; pp. 422-426.

Wolfgang Kiefer et al.; "Femtosecond time-resolved spectroscopy of elementary molecular dynamics"; Naturwissenschaften; 2002; pp. 250-258.

Alois Renn et al.; "Multidimensional Holography by Persistent Spectral Hole Burning"; The Journal of Physical Chemistry A, vol. 106, No. 13; Apr. 4, 2002; pp. 3045-3060.

T.C. Weinacht et al.; "Using feedback for coherent control of quantum systems"; Journal of Optics B: Quantum and Semiclassical Optics; 2002; pp. R35-R52.

Niels E. Henriksen; "Laser control of chemical reactions"; Chem. Soc. Rev. 3137 42; 2002; pp. 37-42.

Stuart A. Rice et al.; "Active control of product selection in a chemical reaction: a view of the current scene"; Phys. Chem. Chem. Phys.; 2002; pp. 1683-1700.

Allen J. Bard et al.; "Holy Grails in Chemistry"; American Chemical Society, vol. 28, No. 3; Mar. 1995.

Marcos Dantus; "Ultrafast Probing and Control of Molecular Dynamics: Beyond the Pump-Probe Method"; pgs. 169-188. Kuhn & Weyh SRZ Sep. 4, 2001.

Bern Kohler et al.; "Controlling the Future of Matter"; Acc. Chem. Res., vol. 28, No. 3; 1995; pp. 133-140.

M.R. Fetterman et al.; "Propagation of Complex Laser Pulses in Optically Dense Media"; The American Physical Society, Physical Review Letters, vol. 82, No. 20, May 17, 1999; pp. 3984-3987.

D. Yelin et al.; "Adaptive femtosecond pulse compression"; Optics Letters, vol. 22, No. 23, Dec. 1, 1997; pp. 1793-1795.

A.V. Sokolov; "Subfemtosecond compression of periodic laser pulses"; Optics Letters, vol. 24, No. 17, Sep. 1, 1999; pp. 1248-1250.

H.S. Eisenberg et al.; "Phase Defects in Self-Focusing of Ultrashort Pulses"; Physical Review Letters, vol. 83, No. 3, Jul. 19, 1999; pp. 540-543.

D.M. Villeneuve et al.; "Using frequency-domain manipulation of stretched femtosecond laser pulses to create fast rise and fall times on picosecond pulses"; Applied Physics B74 (Suppl), 2002; pp. S157-S161.

Dai-Sik Kim et al.; "Femtosecond-pulse distortion in quantum wells"; Appl. Phys B 74, vol. 48. No. 24; Dec. 15, 1993; pp. 17902-17905.

Anthony P. Peirce et al.; "Optimal control of quantum-mechanical systems: Existence, numerical approximation and applications"; Physical Review A, vol. 37, No. 12; Jun. 15, 1988; pp. 4950-4964.

J.M. Geremia et al.; "Incorporating physical implementation concerns into closed loop quantum control experiments"; Journal of Chemical Physics, vol. 113, No. 24; Dec. 22, 2000; pp. 10841-10848.

Thomas Hornung et al.; "Teaching optimal control theory to distill robust pulses even under experimental constraints"; Physical Review A, vol. 65; 2002; pp. 021403-1-021403-4.

Jianshu Cao et al.; "Intrapulse Dynamical Effects in Multiphoton Processes: Theoretical Analysis"; J. Phys. Chem. A; vol. 102, 1998; pp. 4284-4290.

Amichay Vardi et al.; "Laser catalysis with pulses"; Physical Review A, vol. 58, No. 2; Aug. 1998; pp. 1352-1360.

Kazuya Takasago et al.; "Evaluation of Femtosecond Pulse Shaping with Low-Loss Phase-Only Masks"; IEEE Journal of Selected Topics in Quantum Electronics, vol. 4, No. 2; Mar./Apr. 1998; pp. 346-352.

M.E. Fermann et al.; "Shaping of ultrashort optical pulses by using an integrated acousto-optic tunable filter"; Optics Letters, vol. 18, No. 18; Sep. 15, 1993; pp. 1505-1507.

V.L. da Silva et al.; "Nonlinear pulse shaping and causality"; Optics Letters, vol. 18, No. 8; Apr. 15, 1993; pp. 580-582.

E. Zeek et al.; "Adaptive pulse compression for transform-limited 15-fs high-energy pulse generation"; Optics Letters, vol. 25, No. 8; Apr. 15, 2000; pp. 587-589.

A. Apolonski et al.; "Controlling the Phase Evolution of Few-Cycle Light Pulses"; Physical Review Letters, vol. 85, No. 4; Jul. 24, 2000; pp. 740-743.

Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342-345.

David J. Jones et al.; "Carrier-Envelope Phase Control of Femtosecond Mode-Locked Lasers and Direct Optical Frequency Synthesis"; Science magazine, vol. 288; Apr. 28, 2000; pp. 635-639.

Vladimir Kalosha et al.; "Generation of Single Dispersion Precompensated 1-fs Pulses by Shaped-Pulse Optimized High-Order Stimulated Raman Scattering"; Physical Review Letters, vol. 88, No. 10; Mar. 11, 2002; pp. 103901-1-13901-4.

Donna Strickland et al.; "Compression of Amplified Chirped Optical Pulses"; Optics Communications; vol. 55, No. 6; Oct. 15 1985; pp. 447-449.

H. Wang et al.; "Abstract-20-fs pulse shaping with a 512-element phase-only liquid crystal modulator"; IEEE Journal of Selected Topics in Quantum Electronics; 7 (4): 718-727; Jul./Aug. 2001 (1 page).

L. Xu et al.; "Abstract-Programmable chirp compensation for 6-fs pulse generation with a prism-pair-formed pulse shaper"; IEEE Journal of Quantum Electronics; 36 (8): 893-899; Aug. 2000 (1 page).

CVI Laser Corporation; "TNM-2 Negative Group Velocity Dispersion Mirrors"; www.cvilaser.com/ultra-fast; Jan. 13, 2002 (2 pages).

H. Takada et al.; "Large-ratio stretch and recompression of sub-10-fs pulses utilizing dispersion managed devices and a spatial light modulator"; Appl. Phys. B 74 [Suppl.]; 2002; pp. S253-S257.

N. Karasawa et al.; "Optical pulse compression to 5.0 fs by by use only a spatial light modulator for phase compensation"; J. Opt. Soc. Am. B, vol. 18, No. 11; Nov. 2001; pp. 1742-1746.

C.P.J. Barty et al.; "Generation of 18-fs, multiiterawatt pulses by regenerative pulse shaping and chirped-pulse amplification"; Optics Letters, vol. 21, No. 9; May 1, 1996; pp. 668-670.

Marcos Dantus; GeneticAlgorithm-v4.nb to simulate an adaptive genetic algorithm;Oct. 2001; pp. 1-7.

M. Hacker et al.; "Iterative Fourier transform algorithm for phase-only pulse shaping"; Optics Express, vol. 9, No. 4, Aug. 13, 2001; pp. 191-199.

T. Brixner et al.; "Feedback-controlled optimization of amplified femtosecond laser pulses"; Applied Physics B 68; 1999; pp. 281-284.

A. Efimov et al.; "Minimization of dispersion in an ultrafast chirped pulse amplifier using adaptive learning"; Appl. Phys. B 70 (Suppl); 2000; pp. S133-S141.

D. Zeidler et al.; "Evolutionary algorithms and their application to optimal control studies"; Physical Review A, vol, 64; 2001; pp. 023420-1-023420-13.

C. Rangan et al.; "Optimally shaped terahertz pulses for phase retrieval in a Rydberg-atom data register"; Physical Review A, vol. 64; 2001; pp. 033417-1-033417-5.

T. Tanabe et al.; "Compensation for a Transfer Function of a Regenerative Amplifier to Generate Accurately Shaped Ultrashort Pulses in Both the Amplitude and Phase"; IEE J. of Selected Topics in QUantum Elecronics, vol. 10, No. 1; Jan./Feb. 2004; pp. 221-228.

Hosseini, S. Abbas et al.; "Coherent control of multiphoton transitions with femtosecond pulse shaping"; Physical Review A; pp. 033410-1-033410-7.

Yan, Y.J. et al.; "Electronic dephasing, vibrational relaxation, and solvent friction in molecular nonlinear optical line shapes"; J. Chems. Phys.; Oct. 15, 1988; pp. 5160-5176.

Meshulach, M. et al.; "Coherent quantum control of multiphoton transitions by shaped ultrashort optical pulses" Phys. Rev. A 60; 1999; pp. 1287-1292.

Weinacht, T.C. et al.; "Controlling the shape of a quantum wavefunction"; Nature, vol. 397; Jan. 1999; pp. 233-235.

Buist, A.H. et al.; "Probing microscopic chemical environments with high-intensity chirped pulses"; Optics Letters 24; 1999; pp. 244-246.

Broers, B. et al.; "Large interference effects of small chirp observed in two-photon absorbtion"; Opt. Commun. 91; 1992; p. 57-61.

Broers, B. et al.; "Diffraction and focusing of spectral energy in multiphoton processes"; Phys Rev. A 46; 1992; p. 2749-2756.

Walowicz, K.A. et al.; "Multiphoton Intrapulse Interference 1: Control of Multiphoton Processes in Condensed Phases"; J. Phys. Chem A 106 (41); Oct. 17, 2002; pp. 9369-9373.

Zheng, Z. et al.; "Coherent control of second harmonic generation using spectrally phase coded femtosecond waveforms"; Chem. Phys. 267; 2001; pp. 161-171.

Clara et al.; "Femtoscond laser mass spectroscopy of ferrocenes: Photochemical stabilization by bridged cyclopentadienyl rings?"; International Journal of Mass Spectrometry, Elsevier Science Publishers, vol. 203, No. 1-3; Dec. 26, 2000; pp. 71-81.

Bucksbaum, Philip; "An atomic dimmer switch"; Nature; Nov. 19, 1998; vol. 396; pp. 217-219.

Dela Cruz, J.M. et al.; "Multiphoton Intrapulse Interference 3: Probing Microscopic Chemical Environments"; J. Phys. Chem. A 2004, 108; pp. 53-58.

Goswami, D.; "Optical pulse shaping approaches to coherent control"; Physics Reports 374; 2004; pp. 385-481.

Leibfried, D. et al.; "Quantum information with trapped ions at NIST"; Journal of Modern Optics; vol. 50, No. 6/7; Apr.-May 2003; pp. 1115-1129.

Lozovoy, V.V.; "Multiphoton intrapulse interference. II. Control of two- and three-photon laser induced fluorescence with shaped pulses"; J. Chem. Phys. 118 (7); Feb. 15, 2005; pp. 3187-3196.

Roy, I. et al; "Ceramic-based nanoparticles entrapping water-soluble photosensitizing drugs: A novel drug carrier system for photodynamic therapy"; J. Am. Chem. Soc. 125; 2003; pp. 7860-7865.

VandenBout, D.A. et al.; "Discrete intensity jumps and intramolecular electronic energy transfer in the spectroscopy of single conjugated polymer molecules"; Science 277; 1997; pp. 1074-1077.

Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.

Kovtoun et al.; "Mass-Correlated Pulsed Extraction: Theoretical Analysis and Implementation With a Linear matrix-Assisted laser Desorption/Ionization Time of Flight Mass Spectrometer"; Journal of the American Society for Mass Spectrometry, Elsevier Science Inc; vol. 11, No. 10; Oct. 2000; pp. 841-853.

Cumpston, B.H. et al.; "New Photopolymers based on Two-Photon Absorbing Chromophores and Application to Three-Dimensional Microfabricaton and Optical Storage"; Mat. Res. Soc. Symp. Proc; vol. 488; 1998; pp. 217-225.

Cumpston,B.H. et al.; "Two-photon polymerization initiators for three-dimensional optical data storage and microfabrication"; Letters to Nature; vol. 398; Mar. 4, 1999; pp. 51-54.

Lu, Y.M. et al.; "Highly sensitive two-photon chromophores applied to three dimensional lithographic microfabrication: design, synthesis and characterization towards two-photon absorbtion cross section"; J. Mater Chem. 14(1); 2004; pp. 75-80.

Postnikova, B.J. et al.; "Towards nanoscale three-dimensional fabrication using two-photon initiated polymerization and near-field excitation"; Microelectron. Eng. 69 (2-4); Sep. 2003; pp. 459-465.

Sun, H.B. et al.; "Two-photon laser precision microfabrication and its applications to micronano devices and systems"; J. Lightwave Technol. 21(3); Mar. 2003; pp. 624-633.

Mitra et al.; "Nonlinear Limits to the Information Capacity of Optical Fibre Communications"; Nature; vol. 411; Jun. 28, 2001; pp. 1027-1030.

Brattke, S. et al.; "Generation of Photon Number States on Demand via Cavity Quantum Electrodynamics"; Phys. Rev. Lett.; vol. 86; Apr. 16, 2001; pp. 3534-3537.

Goswami, D.; "Ultrafast Pulse Shaping Approaches to Quantum Computing"; Indian Institute of Technology; Dec. 24, 2003 (8 pages).

Xu, C. et al.;"Two photon optical beam induced current imaging throughout backside of integrated circuits"; Appl. Phys. Lett. 71; 1997; pp. 2578-2580.

Yang, W. et al.; "High-ratio Electro-optical Data Compression for Massive Accessing Networks Using AOM-based Ultrafast Pulse Shaping"; Journal of Optical Communications; vol. 22, No. 1; 2001; pp. 694-697.

Kane, Daniel J. et al.; "Single-shot measurement of the intensity and phase of an arbitrary ultrashort pulse by using frequency-resolved optical gating"; Optics Letters, vol. 18, No. 10; May 15, 1993; pp. 823-825.

Kane, Daniel J. et al.; "Single-shot measurement of the intensity and phase of a femtosecond UV laser pulse with frequency-resolved optical gating"; Optics Letters, vol. 19, No. 14; Jul. 15, 1994; pp. 1061-1063.

Clement, Tracy Sharp et al.; "Single-Shot measurement of the amplitude and phase of ultrashort laser pulses in the violet"; Optics Letters, vol. 20, No. 1; Jan. 1, 1995; pp. 70-72.

Kohler, Bern et al.; "Phase and intensity characterization of femtosecond pulses from a chirped-pulse amplifier by frequency-resolved optical gating"; Optics Letters, vol. 20, No. 5; Mar. 1, 1995; pp. 483-485.

Sweetser, John N. et al.; "Transient-grating frequency-resolved optical gating"; Optics Letters, vol. 22, No. 8; Apr. 15, 1997; pp. 519-521.

Trebino, Rick et al.; "Measuring ultrashort laser pulses in the time-frequency domain using frequency-resolved optical gating"; Rev. Sci. Instrum. 68 (9); Sep. 1997; pp. 3277-3295.

Dudley, John M. et al.; "Complete Characterization of Ultrashort Pulse Sources at 1550 nm"; IEEE Journal of Quantum Electronics, vol. 35, No. 4; Apr. 1999; pp. 441-450.

Trebino, Rick et al.; "The Dilemma of Ultrashort-Laser-Pulse Intensity and Phase Measurement and Applications"; IEEE Journal of Quantum Electronics, vol. 35, No. 4; Apr. 1999; pp. 418-420.

Cormack, I.G. et al.; "Practical measurement of femtosecond optical pulses using time-resolved optical gating"; Optics Communications 194; Jul. 15, 2001; pp. 415-424.

Chu, K.C. et al.; "Direct measurement of the spectral phase of femtosecond pulses"; Optics Letters, vol. 20, No. 8; Apr. 15, 1995; pp. 904-906.

Sullivan, A. et al.; "Quantitative investigation of optical phase-measuring techniques for ultrashort pulse lasers "; J. Opt. Soc. Am. B, vol. 13, No. 9; Sep. 1996; pp. 1965-1978.

Baltuska, Andrius et al.; "Amplitude and phase characterization of 4.5-fs pulses by frequency-resolved optical gating"; Optics Letters, vol. 23, No. 18; Sep. 15, 1998; pp. 1474-1476.

Gallmann, L. et al.; "Techniques for the characterization of sub-10-fs optical pulses: a comparision"; Appl. Phys. B 70 (Suppl): 2000; pp. S67-S75.

Anderson, M.E. et al.; "The effects of noise on ultrashort-optical-pulse measurement using SPIDER"; Appl. Phys. B 70 (Suppl); 2000; pp. S85-S93.

Nicholson, J.W. et al; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330-339.

Dorrer, Christophe et al.; "Precision and consistency criteria in spectral phase interferometry for direct electric-field reconstruction"; J. Opt. Soc. Am. B, vol. 19, No. 5; May 2002; pp. 1030-1038.

Walmsley, Ian A. et al.; "Characterization of the electric field of ultrashort optical pulses"; J. Opt. Soc. Am. B., vol. 13, No. 11; Nov. 1996; pp. 2453-2463.

Lange, H. Rudiger et al.; "Reconstruction of the Time Profile of Femtosecond Laser Pulses through Cross-Phase Modulation"; IEEE Journal of Selected Topics in Quantum Electronics, vol. 4, No. 2; Mar./Apr. 1998; pp. 295-300.

Iaconis, C. et al.; "Direct Interferometric Techniques for Characterizing Ultrashort Optical Pulses"; IEEE Journal of Selected Topics in Quantum Electronics, vol. 4, No. 2; Mar./Apr. 1998; pp. 285-294.

Iaconis, C. et al.; "Spectral phase interferometry for direct electric-field reconstruction of ultrashort optical pulses"; Optics Letters, vol. 23, No. 10, May 15, 1998; pp. 792-794.

Dietrich, P. et al.; "Determining the absolute carrier phase of a few-cycle laser pulse"; Optics Letters, vol. 25, No. 1, Jan. 1, 2000; pp. 16-18.

Reid, D.T. et al.; "Amplitude and phase measurement of mid-infrared femtosecond pulses by using cross-correlation frequency-resolved optical gating"; Optics Letters, vol. 25, No. 19, Oct. 1, 2000; pp. 1478-1480.

Michelmann, K. et al.; "Measurement of the Page function of an ultrashort laser pulse"; Optics Communications; Oct. 15, 2001, pp. 163-170.

Gallmann, L. et al.; "Spatially resolved amplitude and phase characterization of femtosecond optical pulses"; Optics Letters, vol. 26, No. 2; Jan. 15, 2001; pp. 96-98.

Kakehata, Masayuki et al.; "Single-shot measurement of carrier-envelope phase changes by spectral interferometry"; Optics Letters, vol. 26, No. 18; Sep. 15, 2001; pp. 1436-1438.

Geindre, J.P. et al.; "Single-shot spectral interferometry with chirped pulses"; Optics Letters, vol. 26, No. 20; Oct. 15, 2001; pp. 1612-1614.

Dorrer, C. et al.; "Direct space-time characterization of the electric fields of ultrashort optical pulses"; Optics Letters, vol. 27, No. 7; Apr. 1, 2002; pp. 548-550.

Trebino, R. et al; "Measuring Ultrashort Laser Pulses Just Got a Lot Easier!"; Optics & Photonics News; Jun. 2001; pp. 22-25.

Zheng, Z. et al. "Spectral phase correlation of coded femtosecond pulses by second-harmonic generation in thick nonlinear crystals"; Opt. Lett. 25; 2000; pp. 984-986.

Spielmann, C. et al.; "Ultrabroadband Femtosecond Lasers"; IEEE Journal of Quantum Electronics; vol. 30, No. 4; Apr. 1994; pp. 1100-1114.

Yelin, D. et al.; "Laser scanning third-harmonic-generation microscopy in biology"; Optics Express; vol. 5, No. 8; Oct. 11, 1999; pp. 169-175.

Zipfel, W.R. et al; "Nonlinear magic: multiphoton microscopy in the biosciences"; Natire Biotechnology, 121 (11); Nov. 2003; pp. 1369-1377.

Larson, D.R. et al.; "Water soluble quantum dots for multiphoton imaging in vivo"; Science 300: May 30, 2003; pp. 1434-1436.

Osborn, D.L. et al.; "Spectral and intensity dependence of spatially resolved two-photon conductivity defects on a GaAsP photodiode"; J. Appl. Phys 89; 2001; pp. 626-633.

Pastirk, I. et al; "Selective two-photon microscopy with shaped femtosecond pulses"; Opt. Express 11; 2003; pp. 1695-1701.

Drexler W. et al.; "In vivo ultrahigh-resolution optical coherence tomography"; Optics Letters; vol. 24, No. 17; Sep. 1, 1999; pp. 1221-1223.

Hasan, T. et al.; "Photodynamic Therapy of Cancer"; Chapter 40 in Holland Frei Cancer Medicine; BC Dekker Inc.; 2003; (55 pages).

Sharman, W.M. et al.: "Targeted photodynamic therapy via receptor mediated delivery systems"; Adv. Drug Delivery Rev. 56(1); Jan. 2004; pp. 53-76.

Assion, A. et al; "Control of Chemical Reactions by Feedback-Optimized Phase-Shaped Femtosecond Laser Pulses"; Science Magazine, vol. 282; Oct. 30, 1998; pp. 919-922.

Warren, W.S.; "Chemistry with photons"; Science, vol. 262; Nov. 12, 1993; pp. 1008-1009.

Chilla, Juan L.A. et al.; "Direct determination of the amplitude and the phase of femtosecond light pulses"; Optics Letters; vol. 16, No. 1; Jan. 1, 1991; pp. 39-41.

Kim, D.S. et al; "Femtosecond pulse distortion in GaAs quantum wells and its effect on pump-probe or four-wave-mixing experiments"; Physical Review B; vol. 50, No. 24; Dec. 15, 1994; pp. 18240-18249.

Kaindl, Robert A. et al.; "Generation, shaping, and characterization of intense femtosecond pulses tunable from 3 to 20 µm"; J. Opt. Soc. Am. B; vol. 17, No. 12; Dec. 2000; pp. 2085-2094.

Panasenko, Dmitriy et al.; "Single-shot sonogram generation for femtosecond laser pulse diagnostics by use of two-photon absorbtion in a silicon CCD camera"; Optics Letters; vol. 27, No. 16; Aug. 15, 2002; pp. 1475-1477.

Baltuska, Andrius et al.; "Visible pulse compression to 4 fs by optical parametric amplification and programmable dispersion control"; Optics Letters; vol. 27, No. 5; Mar. 1, 2002; pp. 306-308.

Meshulach D. et al.; "Adaptive ultrashort pulse compression and shaping"; Optics Communications 138; 1997; pp. 345-348.

Brixner, T. et al.; "Feedback-controlled femtosecond pulse shaping"; Appl. Phys. B 70 (Suppl); 2000; pp. S119-S124.

Stobrawa, G. et al.; "A new high-resolution femtosecond pulse shaper"; Appl. Phys. B 72; 2001; pp. 627-630.

Hacker, M. et al.; "Frequency doubling of phase-modulated, ultrashort laser pulses"; Appl. Phys. B 73; 2001; pp. 273-277.

Weiner, Andrew M. et al.; "Femtosecond Pulse Shaping for Synthesis, Processing and Time-to-Space Conversion of Ultrafast Optical Waveforms"; IEEE Journal of Selected Topics in Quantum Electronics; vol. 4, No. 2; Mar./Apr. 1998; pp. 317-331.

Dudovich, N. et al; "Transform-limited pulses are not optimal for resonant multiphoton transitions"; Phys. Rev. Lett. 86; 2001; pp. 47-50.

Hillegas, C.W. et al.; "Femtosecond laser pulse shaping by use of microsecond radio-frequency pulses"; Optics Letters; vol. 19, No. 10; May 15, 1994; pp. 737-739.

Weiner, A.M. et al.; "Programmable Shaping of Femtosecond Optical Pulses by Use of 128-Element Liquid Crystal Phase Modulator"; IEEE Journal of Quantum Electronics; vol. 28, No. 4; Apr. 1992; pp. 908-920.

Matuschek. N.; "Back-side-coated chirped mirrors with ultra-smooth broadband dispersion characteristics"; Applied Physics B 71; Sep. 6, 2000; pp. 509-522.

Ding. Y.; "Femtosecond pulse shaping by dynamic holograms in photorefractive multiple quantum wells"; Optics Letters; vol. 22, No. 10; May 15, 1997; pp. 718-720.

Imeshev, G. et al. "Engineerable femtosecond pulse shaping by second-harmonic generation with Fourier synthetic quasi-phase-matching gratings"; Optics Letters; vol. 23, No. 11; Jun. 1, 1998; pp. 864-866.

Tull, J.X. et al.; "High-Resolution, Ultrafast Laser Pulse Shaping and Its Applications"; Advances in Magnetic and Optical Resonance; vol. 20; 1997; pp. 1-65.

Weiner, A.M.; "Femtosecond pulse shaping using spatial light modulators"; Rev. Sci. Instrum. vol. 71(5); 2000; pp. 1929-1960.

Schreier, F. et al.; "Femtosecond pulse shaping with a stratified diffractive structure"; Optics Communications 185; 2000; pp. 227-231.

Bhattacharya, N. et al.; "Implementation of Quantum Search Algorithm using Classical Fourier Optics"; Phys. Rev. Lett.; vol. 88. No. 13; Apr. 1, 2002; p. 137901-1-137901-4.

Baumert, T. et al. "Femtosecond pulse shaping by an evolutionary algorithm with feedback"; Appl. Phys. B 65; 1997; pp. 779-782.

Hornung, Thomas et al.; "Adapting optimum control theory and using learning loops to provide experimentally feasible shaping mask patterns"; Journal of Chemical Physics; vol. 115, No. 7; Aug. 15, 2001; pp. 3105-3111.

Meshulach, D. et al.; "Adaptive real-time femtosecond pulse shaping"; J. Opt. Soc. Am. B; vol. 15, No. 5; May 1998; pp. 1615-1619.

Zeidler, D. et al.; "Adaptive compression of tunable pulses from a non-colinear-type OPA to below 16 fs by feedback-controlled pulse shaping"; Appl. Phys. B 70 (Suppl); 2000; pp. S125-S131.

Comstock et al.; "Multiphoton intrapulse interference 6; binary phase shaping"; Optics Express Opt. Soc. America USA, vol. 12, No. 6, Mar. 22, 2004; pp. 1061-1066.

Hu et al.; "A New Nonlinear Optical Crystal-BaAlBO3F2(BABF)"; Japanese Journal of Applied Physics, vol. 41, No. 10B, Part 2, Oct. 15, 2002; pp. L1131-L1133.

Weiner et al.; "Shaping of femtosecond pulses using phase-only filters designed by simulated annealing"; Journal of the Optical Society of America A (Optics and Image Science) USA, vol. 10, No. 5, May 1993; pp. 1112-1120.

M. Dantus et al., "Experimental Coherent Laser Control of Physicochemical Processes", Chem. Rev. 2004, 104, pp. 1813-1859.

H. Zou, C. Zhou, Femtosecond Pulse Shaping with Space-to-Time Conversion Based on Planar Optics, Optik Optics, ScienceDirect, 2006/2007, pp. 5-8.

S. Zhang, X. Zhang, J. Huang, L. Deng, Z. Sun, W. Zhang, Z. Wang, Z. Xu, R.Li, Coherent Enhancement of Broadband Frequency Up-Conversion in BBO Crystal by Shaping Femtosecond Laser Pulses, Optics Communications, ScienceDirect, 2006/2007, pp. 559-563.

Y. Oishi, A. Suda, F. Kannari, K. Midorikawa, Intense Femtosecond Pulse Shaping Using a Fused-Silica Spatial Light Modulator, Optics Communications, ScienceDirect, 2006/2007, pp. 305-309.

B. Xu, Y. Coello, V.Lozovoy, D. Harris; M. Dantus, Pulse Shaping of Octave Spanning Femtosecond Laser Pulses, Optics Express, vol. 14, No. 22, Oct. 30, 2006, six pages.

F.M. Reinert, M. Ninck, W. Lüthy, T. Feurer, Shaping a Femtosecond Pulse with a Programmable Thermo-Optically Driven Phase Modulator, Optics Express, vol. 15, No. 7, Apr. 2, 2007, six pages.

H. Miao, A. Weiner, C. Langrock, R. Roussev, M. Fejer, Sensing and Compensation of Femtosecond Waveform Distortion Induced by All-Order Polarization Mode Dispersion at Selected Polarization States, Optics Letters, vol. 32, No. 4, Feb. 15, 2007, pp. 424-426.

S. Nath, D. Urbanek, S. Kern, M. Berg, High-Resolution Raman Spectra with Femtosecond Pulses: An Example of Combined Time- and Frequency-Domain Spectroscopy, Physical Review Letters, 2006, pp. 267401-1 to 267401-4.

Dela Cruz, J. et al., "Use of coherent control methods through scattering biological tissue to achieve functional imaging," PNAS, vol. 101, No. 49, Dec. 7, 2004, pp. 16996-17001.

Weiner, A.M. et al. "Generation of terahertz-rate trains of femtosecond pulses by phase-only filtering," Optics Letters, vol. 15, No. 1, Jan. 1, 1990, pp. 51-53.

Kroner, D. et al., Asymmetric Laser Excitation in Chiral Molecules: Quantum Simulations for a Proposed Experiment, Chemical Physics Letters Elsevier Netherland, vol. 372, No. 1-2, Apr. 22, 2003, pp. 242-248.

Hoki, K. et al., Locally Designed Pulse Shaping for Selective Preparation of Enantiomers from their Racemate, Journal of Chemical Physics, New York, NY, US, vol. 114, No. 4, Jan. 22, 2001, pp. 1575-1581.

Bychkov S. S. et al., Laser Synthesis of Chiral Molecules in Isotropic Racemic Media, Journal of Experimental and Theoretical Physics, Nauka/Interperiodica, MO, vol. 93, No. 1, Jul. 1, 2001, pp. 24-32.

Hoki, K. et al., Selective Preparation of Enantiomers from a Racemate by Laser Pulses: Model Simulation for Oriented Atropisomers with Coupled Rotations and Torsions, Chemical Physics Elsevier Netherlands, vol. 267, No. 1-3, Jun. 1, 2001, pp. 59-79.

Brixner T., et al., Quantum Control by Ultrafast Polarization Shaping, Phys Rev Lett, vol. 92, No. 20, May 21, 2004, pp. 208301-1.

Brixner, T., A. Oehrlein, M. Strehle, and G. Gerber "Feedback-controlled femtosecond pulse shaping" Applied Physics B 70 [Suppl.], S119-S124 (2000).

O'Shea, Patrick, Mark Kimmel, Xun Gu, and Rick Trebino "Highly simplified device for ultrashort-pulse measurement" Optics Letter/ vol. 26, No. 12 / Jun. 15, 2001.

Zheng, Z. and A.M. Wolfe "Coherent control of second harmonic generation using spectrally phase coded femtosecond waveforms" Chemical Physics 267 (2001) 161-171 (Received Aug. 31, 2000).

Chung, Jung-Ho, "Ambiguity of Ultrashort Pulse Shapes Retrieved From the Intensity Autocorrelation and the Power Spectrum," IEEE Journal on Selected topics in Quantum Electronics, vol. 7, No. 4 (Jul./Aug. 2001) pp. 656-666.

Kubo, Atsushi, et al., "Femtosecond Imaging of Surface Plasmon Dynamics in a Nanostructured Silver Film," Nano Letters, vol. 5, No. 6 (2005) American Chemical Society, pp. 1123-1127.

Lim, Sang-Hyun et al., "Chemical Imaging by Single Pulse Interferometric Coherent Anti-Stokes Raman Scattering Microscopy," (2006) pp. 5196-5204. vol. 110, No. 11. J. Phys. Chem. B.

Nisoli, M., et al., "Generation of high energy 10 fs pulses by a new pulse compression technique," Appl. Phys. Lett., vol. 68, No. 20 (May 13, 1996) pp. 2793-2795.

Oron, Dan, et al., "Scanningless depth-resolved microscopy," Optics Express, vol. 13, No. 5 (Mar. 7, 2005).

Takasago, Kazuya, et al., "Design of Frequency-Domain Filters for Femtosecond Pulse Shaping," Part 1, No. 2A (Feb. 1996)pp. 624-629. Jpn. J. Appl. Phys.

Zang, Hegui, et al., "Study on Frequency-doubling Effect of the Dually Doped KTP Crystals," Journal of Synthetic Crystals vol. 29, No. 2 (May 2000).

M. Hacker et al., "Iterative Fourier Transform Algorithm for Phase-Only Pulse Shaping", Optics Express, vol. 9, No. 4, Aug. 13, 2001, pp. 191-199.

R. Bartels et al., "Shaped-Pulse Optimization of Coherent Emission of High-Harmonic Soft X-Rays", 2000 Macmillan Magazines Ltd., Nature, vol. 406. Jul. 13, 2000, pp. 164-166.

Ogawa et al, Dependence of the Laser Two-Photon Ionization Process in Solution on the Laser Pulse Width, Analytical Chemistry, vol. 73, Mar. 20, 2001, pp. 2066-2069.

Zeek, E. et al., "Pulse Compression by Use of Deformable Mirrors," Optics Letters, OSA, Optical Society of America, vol. 24, No. 7, Apr. 1, 1999, pp. 493-495.

Sardesai, H et al. "A Femtosecond Code-Division Multiple-Access Communication System Test Bed," Journal of Lightwave Technology, IEEE Service Center, vol. 16, No. 11, Nov. 1, 1998, p. 1953-1964.

* cited by examiner

CONTROL SYSTEM AND APPARATUS FOR USE WITH ULTRA-FAST LASER

CROSS-REFERENCE TO RELATED APPLICATIONS

This application is a continuation-in-part of U.S. Ser. No. 10/265,211, filed Oct. 4, 2002 now U.S. Pat. No. 7,450,618, which is a Continuation-in-Part of PCT/US02/02548, filed Jan. 28, 2002, which claims priority to U.S. Provisional Application Ser. No. 60/265,133, filed Jan. 30, 2001; all of which are incorporated by reference herein.

This application is a continuation-in-part of U.S. Ser. No. 10/628,874, filed Jul. 28, 2003 now U.S. Pat. No. 7,105,811, which is a Continuation of PCT/US02/02548, filed Jan. 28, 2002 which claims priority to U.S. Provisional Application Ser. No. 60/265,133, filed Jan. 30, 2001; all of which are incorporated by reference herein.

This application is a continuation-in-part of U.S. Ser. No. 10/791,377, filed Mar. 2, 2004 now U.S. Pat. No. 7,609,731, which is a continuation-in-part of U.S. Ser. No. 10/265,211, filed Oct. 4, 2002 now U.S. Pat. No. 7,450,618, which is a Continuation-in-Part of PCT/US02/02548, filed Jan. 28, 2002 which claims priority to U.S. Provisional Application Ser. No. 60/265,133, filed Jan. 30, 2001; all of which are incorporated by reference herein.

BACKGROUND AND SUMMARY OF THE INVENTION

The present invention generally relates to a laser, and more particularly, to a control system and apparatus for use with an ultra-fast laser.

Conventionally, laser desorption mass spectrometry has been used with a fixed laser beam pulse shape and computers for simple chemical analysis processes on purified molecules with or without a matrix. The laser beam pulse shape was not considered an important parameter and was not modified; whatever fixed shape was set by the manufacturer for the ultraviolet laser was used in the tests. The general concept of typically laser selective ion formation from molecules in a molecular beam is disclosed in the following publication: Assion et al., "Control of Chemical Reactions by Feedback-Optimized Phase-Shaped Femtosecond Laser Pulses," *Science*, Vol. 282, page 919 (Oct. 30, 1998). The pulse shaping process with a learning algorithm is disclosed in Judson et al., "Teaching Lasers to Control Molecules," *Physical Review Letters*, Vol. 68, No. 10, page 1500 (Mar. 9, 1992). It is noteworthy, however, that the Assion article discloses use of an 80 femtosecond laser pulse and requires molecules to be isolated in a molecular beam, while the Judson article discloses use of a one nanosecond laser pulse and is purely conceptual as it does not include experimental results. Similarly, the findings by Assion et al. had great scientific interest, but the results were not sufficiently reproducible to be considered useful for analytical purposes.

It is also known to employ nanosecond lasers for matrix-assisted laser desorption ionization (hereinafter "MALDI"). Examples of this are disclosed in U.S. Pat. No. 6,130,426 entitled "Kinetic Energy Focusing for Pulsed Ion Desorption Mass Spectrometry" which issued to Laukien et al. on Oct. 10, 2000, and U.S. Pat. No. 6,111,251 entitled "Method and Apparatus for MALDI Analysis" which issued to Hillenkamp on Aug. 29, 2000; both of these patents are incorporated by reference herein. Furthermore, the traditional role of the laser in a mass spectrometer with MALDI is to provide energy to the matrix molecules, wherein this energy dissipates and causes evaporation and ionization of the protein analyte dissolved in it. The laser, therefore, plays an indirect role that depends on energy transfer processes that may take from picoseconds to microseconds. Because excitation is indirect, pulse wavelength has not been found to cause significant differences in the outcome. Direct laser excitation of the proteins with nanosecond lasers typically causes the proteins to char.

Laser induced, selective chemical bond cleavage has also been explored but with fairly limited success. It is believed that very simple molecules, such a HOD (partially deuterated water), have had only the OH and OD bonds cleaved with a nanosecond narrow line laser to vibrationally excite the specimen and then an ultraviolet laser pulse was employed to perform the cleaving. The desired laser frequency for vibrational excitation could be determined a priori in the gas-phase sample. More importantly, the HOD molecule is unique because the energy can be deposited in one of the bonds and it remains there for very long times, which are longer than nanoseconds. For the HOD experiments using selective bond excitation, no appreciable pulse shaping was used. This method was not known to have been employed for a protein or MALDI process, and was not known to have been successfully used for any other atomic bonds in other molecules, especially not in a condensed phase. It is also noteworthy that MALDI, with a matrix, has been used in an attempt to perform limited bond cleavage, as is discussed in U.S. Pat. No. 6,156,527 entitled "Characterizing Polypeptides" which issued to Schmidt et al. on Dec. 5, 2000, and is incorporated by reference herein. However, the approach of Schmidt et al. does not modify and optimize the laser pulse shape or other laser properties to achieve limited bond cleavage.

In accordance with the present invention, a control system and apparatus for use with an ultra-fast laser is provided. In another aspect of the present invention, the apparatus includes a laser, pulse shaper, detection device and control system. A further aspect of the present invention employs a femtosecond laser and a spectrometer. In another aspect of the present invention, a femtosecond laser and binary pulse shaping are employed. A multiphoton intrapulse interference method is used to characterize the spectral phase of laser pulses and to compensate any distortions in an additional aspect of the present invention. In another aspect of the present invention, a system employs multiphoton intrapulse interference phase scan to improve the laser pulse performance. Furthermore, another aspect of the present invention locates a pulse shaper and/or MIIPS unit between a laser oscillator and a laser amplifier. In yet another aspect of the present invention, the control system and apparatus are used in a MALDI process. Still another aspect of the present invention employs the control system and apparatus to cleave chemical bonds in a specimen and/or to determine the amino acid sequence of a protein specimen. Photodynamic therapy and fiber optic communication systems use the laser excitation apparatus with additional aspects of the present invention. A method of ionizing and determining a characteristic of a specimen is also provided.

The present invention is advantageous over conventional constructions since the MIIPS aspect of the present invention employs a single beam which is capable of retrieving the magnitude and sign of second and third order phase modulation directly, without iteration or inversion procedures. Thus, the MIIPS system is much easier to set up and use, thereby creating a much less expensive system which is more accurate than conventional systems and methods. Furthermore, the MIIPS system of the present invention avoids the inaccuracies of the prior FROG, SPIDER and DOSPM methods due to environmental effects such as wind, vibrations and the like. The present invention MIIPS system utilizes the full bandwidth which works best with shorter laser beam pulses, such as femtosecond pulses; this is in contrast to the mere single frequency optimization of some convention devices. The present invention MIIPS system overcomes the traditional need for slower picosecond pulses for space-time correlation corrections due to inherent time delays created with prior synchronous use of multiple matched pulses, a first pump or fundamental pulse and another reference second harmonic pulse, caused by the pulse passage through a pulse shaping crystal. Additionally, the present invention advantageously uses one or more pre-stored comparison values for pulse signal decoding at a communications receiver such that the second reference pulse (and corresponding time delay correlation) are not necessary. The present invention also improves the encoding-decoding functionality of pulses by adding considerably more information to each pulse by obtaining the entire phase function directly from a phase scan. Intrapulse interferences of the present invention causes self separation (for example, inherent communication signal routing address differentiation) thereby allowing use of inexpensive receivers in an asynchronous manner, in other words, without the need for synchronous detection such as by traditional autocorrelation or interferometers.

The control system and apparatus of the present invention are further advantageous over conventional constructions since the present invention allows for analysis and identification of constituents of complex and unknown molecules, such as those used in a MALDI process or proteins, in a relatively quick and automated manner. The present invention advantageously determines optimum laser conditions for maximizing the sensitivity of MALDI based protein sequencing, and to examine ion formation efficiencies for various matrices using tailored laser pulses. The present invention is also advantageously used to control the degree and type of fragmentation for automated protein sequencing. Furthermore, the adaptive laser source permits the optimal desorption from an insoluble protein source and allows for ionization analysis of a protein with or without a matrix. Additional advantages and features of the present invention will become apparent from the following description and appended claims, taken in conjunction with the accompanying drawings.

DETAILED DESCRIPTION OF THE PREFERRED EMBODIMENTS

Pulse Shaping System

Figure 1:
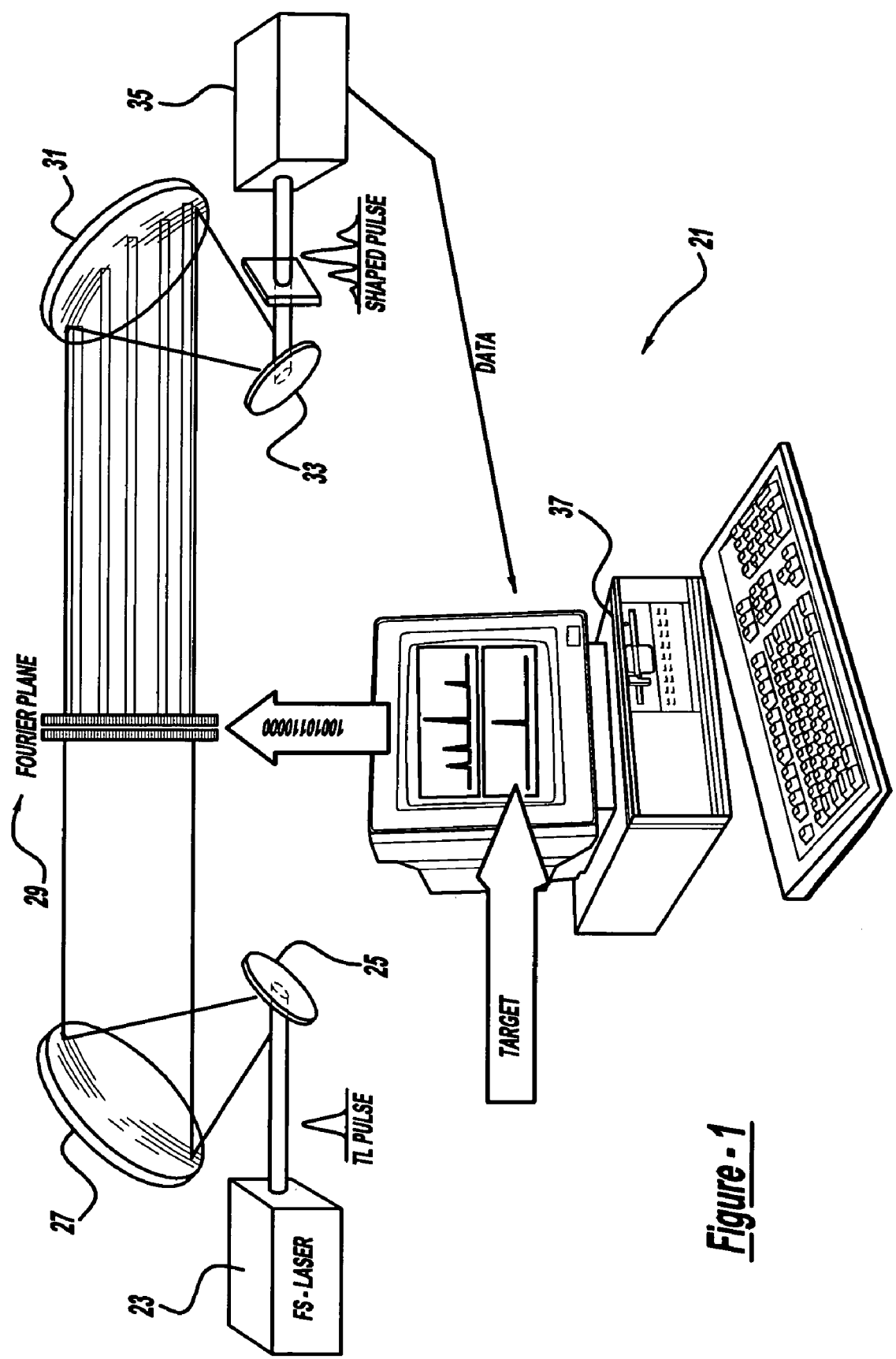
FIG. 1 is a diagrammatic view showing a first preferred embodiment of a control system and apparatus of the present invention.

The first preferred embodiment of a laser system 21 using ultrashort laser pulses of the present invention is generally shown in FIG. 1. System 21 includes a femtosecond laser 23, an upstream grating 25, an upstream concave mirror 27, a spatial light modulator 29, a downstream concave mirror 31, a downstream grating 33, a detection device 35, and a personal computer 37. Personal computer 37 has a microprocessor based electrical control system, memory, an output screen, a data storage device, an input keyboard, and a removable disk. More specifically, the detection device is a spectrometer 39. Bursts or pulses of a laser beam 43 are emitted from laser 23, through the optics 25, 27, 31 and 33, as well as through the spatial light modulator 29 for detection and sensing by spectrometer 39 for further evaluation, analysis, comparison and subsequent control by personal computer 37.

The laser is preferably an ultra-short femtosecond laser that can deliver high peak intensity (with a typical peak greater than $10^{10}$ watts/cm$^2$) which preferably emits laser beam pulses of less than 100 femtosecond duration, and more preferably at or less than 50 femtoseconds, and for certain applications even more preferably at or less than 10 femtosecond duration, for each pulse burst or shot. The intense optical pulses that are required to modify material are formed in a Kerr-Lens mode locked titanium sapphire oscillator. Such lasers are capable of producing hundreds of nanometers of coherent bandwidth, although only about 50 nm are typically used. The output may be amplified in a 1 kHz regenerative chirped pulsed amplifier. The output pulse is typically 100 fs long with a central wavelength of 800 nm and total pulse energy of 0.1 to 1 mJ. Preferred lasers include: the Kapteyn and Murnane femtosecond laser oscillator, which can produce less than 15 fs pulses at 100 MHz; the Hurricane model from Spectra Physics Inc., which is diode pumped and gives 0.8 mJ per pulse with sub-50 fs pulses at 1 kHz; and the CPA-2001+ model from Clark-MXR Inc., which gives 1.3 mJ per pulse with sub-150 fs pulses at 1 kHz, pumping a Clark-MXR Inc. non-collinear parametric amplifier (hereinafter "NOPA") which produces 0.2 mJ per pulse, and is capable of generating sub-20 fs pulses. This NOPA system can even produce pulses between 10 fs and 4.5 fs.

A Fourier plane pulse shaper is preferably used with the present invention for the transmissive construction illustrated with this embodiment. Ultra-fast laser pulses contain from one to fifty optical cycles, and last only a few femtoseconds. This is much faster than most current electronics and therefore shaping with fast time gates is very difficult. On the other hand, because of the uncertainty principle, the optical spectrum spans tens to hundreds of nanometers. Such a large bandwidth is relatively easy to measure and to filter, and there are several techniques to shape the spectrum in the frequency domain, and thereby shape the temporal pulse upon recompression.

In order to access the frequency domain and the individual frequency components that comprise the pulse, a geometric arrangement is employed, using two back-to-back spectrometers. The spectrometers are especially designed to introduce no net temporal dispersion: that is, all colors pass through the spectrometers within the same amount of time. The first spectrometer (including grating 25 and mirror 27) spreads the unshaped pulse spectrum along a line according to its dispersion function $y(\alpha)$. The light intercepts spatial amplitude and phase mask pulse shaper 29 at this point. The mask output then forms the entrance to a second spectrometer (including grating 33 and mirror 31) which recombines the colors into a single shaped pulse.

The heart of pulse shaper 29 is the programmable 256 pixel liquid-crystal mask (consisting of two overlapping 128 pixel liquid crystal arrays) that is placed at the Fourier plane. For the applications envisioned herein, the mask must be capable of shifting the phase of individual frequencies. For alternate embodiment pulse shapers, a different electronically programmable mask that is capable of controlling phase has been demonstrated: a liquid crystal display (hereinafter "LCD"), an acousto-optic modulator (hereinafter "AOM"), a deformable mirror, and a permanently deformed mirror. A LCD spatial light modulator can be obtained from CRI Co. and has a modulator electronic driver.

The AOM consists of an anti-reflection coated Tellurium Dioxide (TeO$_2$) crystal with a piezo electric transducer glued onto one end. The central frequency of the acoustic wave is $\alpha c/2\pi$=200 MHz. The acoustic velocity vs in the crystal is 4.2 km/s and the light pulse spends less than 10 ps in the crystal, so the acoustic wave moves less than 0.002 $\lambda$ acoustic during the transit of the light field through the crystal. Since the acoustic wave is essentially frozen as the optical pulse travels through the crystal, the complex amplitude of the acoustic wave traveling through the crystal in the y direction, $A(t)\cos \alpha ct = A(y/v_s)\cos \alpha ct$, is mapped onto the optical field $E(\alpha)$ as it passes through the AOM. If some of the dispersed optical field encounters a weak acoustic wave, that frequency is attenuated; if the acoustic wave carrier is shifted by phase angle ø, that phase shift is imposed on the optical field. This pulse shaper has a total efficiency of about 20% including the diffraction efficiency of the AOM and the diffraction efficiency of the gratings. The diffracted light is used and the undiffracted "zero order" beam is blocked, to allow full modulation of both amplitude and phase in the shaped beam. The shaped beam than has the form $$E_{shaped}(\omega) = E_{input}(\omega)\, x\alpha(\omega)\, xe^{i\phi(\omega)t} \qquad [1]$$

where $a(\omega)e^{i\phi(\omega)} = A[\gamma(\omega)/v_s]$; $\alpha$ is the frequency, and e is a constant. Fixed pulse shaping optics, such as chirped mirrors, can also be employed.

The transform-limited pulses (hereinafter "TL"), having all their frequencies in phase, are fed into the pulse shaper where curved mirror 27 focuses the spectrum onto Fourier plane 29. Changes in the phase ø and amplitude A of the spectral components indicated by the computer are used to tailor the laser pulse before reconstruction with second curved mirror 31 and grating 33. Once compressed, the shaped pulse is directed to spectrometer 39 for evaluation. The Fourier transform relationship between the time and the frequency domain allows us to calculate the necessary mask to create a certain shaped pulse. These calculations are based on $$f(v) = \frac{1}{2\pi} \int_{\infty}^{0} f(t)\, e^{i2\pi v c t}\, dt \qquad [2]$$

and $$f(t) = \int_{\infty}^{0} f(v)\, e^{-i2\pi v c t}\, dv \qquad [3]$$

where v is the frequency in wave numbers, t is the time, and c is the speed of light.

In this embodiment, the phase and amplitude masks of the pulse shaper are controlled by the computer wherein the laser pulse shape takes a dynamic role. The microprocessor within personal computer 37 will then control laser 23, receive an essentially real time feedback input signal from spectrometer 39, and then perform calculations, comparisons and evaluations, and possibly automatic variation of subsequent pulse shapes. These automated steps can be substituted with manual user calculations and decisions if desired based on personal computer outputs.

As applied to all of the applications herein, selective control of one and multiphoton processes in large molecules, including proteins, is possible using a simple pulse shaping method that is based on taking maximum advantage of the multiphoton intrapulse interference caused in short pulses with large bandwidths. The results show an extraordinary level of control that is robust and sample independent, with contrast ratios near two orders of magnitude (clearly visible with the naked eye). Such large contrast ratios allow for more precise cancellation control of undesired photons and other laser beam characteristics, such that nonlinear transitions induced by each pulse are controlled. Because simple phase functions can be incorporated into a passive optical component such as a mirror, these applications do not require the complexity and expense of computer controlled pulse shapers after initial set up, although systems can still be employed.

Binary Phase Shaping

In the low intensity regime, laser control is dominated by interference of different nonlinear optical pathways connecting the initial and final states. The challenge is finding the proper phase for each frequency within the pulse to achieve constructive interference at the desired pathway and destructive interference elsewhere. Consider two-photon excitation of fluorescent probes, as used in two-photon microscopy, as the target for optimization and envision two chromophores with different two-photon absorption spectra. The goal is to achieve selective excitation by "focusing" the energy available at a specific region of the two-photon spectrum, while minimizing the energy outside of the desired spectral window.

The objective is to introduce phase modulation to cause the two-photon spectrum to be intense only inside the window defined by frequency $2\omega_c$ and width W, and to minimize the background B outside the window. The contrast ratio C is defined as the intensity inside the window divided by the intensity of light outside the window.

The phase between photons of different frequencies takes only two values preferably 0 or preferably $\pi$ to maximize or minimize a given pathway. Any two values whose difference is $\pi$ work equivalently well. The method is defined as binary phase shaping (hereinafter "BPS"). In a preferred embodiment, BPS is used to solve the problem of selective multiphoton excitation with ultrashort laser pulses.

In order to control two-photon excitation, one needs to control the non-linear power spectrum of the laser $E^{(2)}(\omega)$, which can be measured by obtaining the second harmonic spectrum generated using a thin second harmonic generation (hereinafter "SHG") crystal. Selective two-photon excitation is possible when one is able to tune the narrowed non-linear power spectrum to optimize excitation of one chromophore versus another. The effect of spectral phase modulation on SHG can be divided into broad and narrow phase matching bandwidth. Sinusoidal phase modulation, a common function used for laser control, cannot produce contrast ratios greater than 0.5, and as the window is tuned away from the central frequency the contrast drops below 0.1.

Consider two phases, 0 and $\pi$, then the symmetry becomes clear. To maximize the SHG intensity at a frequency $2\omega_C$, the spectral phase needs to be symmetric or antisymmetric about $\omega_C$, such that the frequencies interfere constructively. To minimize the background intensity at all other frequencies, the spectral phase must be asymmetric with respect to all other frequencies away from $\omega_C$, so that destructive interference is maximized. In another preferred embodiment, prime numbers are used to generate the quasi-random phase changes required. The mask that is used to modulate the pulses is designed for a 128-pixel modulator. A proposed phase mask is based on the symmetry requirements of the problem, using the quasi-randomness of prime numbers. This mask is reflected about pixel 64 to obtain the values of pixels 65-128, and is designed to obtain a narrow second harmonic signal at the center of the spectrum, for example. Other preferred embodiments employ a 128-pixel SLM and still other embodiments employ a SLM with greater than 256 pixels.

A titanium-sapphire oscillator, which can be obtained from K&M Labs, is capable of generating pulses as short as 10 fs after a double pass prism compressor is preferably employed. The spectral phase of the pulse is tailored using a computer-controlled pulse shaper. The pulses are centered near 800 nm. The spectral phase of each pulse is corrected using the MII phase-scan (MIIPS) method, which compensates phase distortions to obtain transform-limited (TL) pulses. The binary phase is introduced as an addition to the compensation phase. The shaped laser pulses, with energy ~0.5 nJ per pulse and 87 MHz repetition rate, are focused mildly, to a spot size of ~100 microns in diameter, on a 20 micron thin beta barium borate ($\beta$BBO) type I SHG crystal. The frequency-doubled light is collected with an optical fiber and dispersed on a compact spectrometer, preferably obtainable from Ocean Optics.

Before introducing phase modulation, spectral amplitude restriction is considered and the spectrum of the laser is narrowed using a slit at the Fourier plane. The phase mask is programmed on the SLM and it dramatically narrows the SHG spectrum. The contrast ratio for this mask is 2.5 when the SHG peak is centered. By shifting the position of the mask on the SLM, hence tuning the center of symmetry, it tunes the SHG spectrum.

The absolute value of the spectral amplitude $|E(\omega)|$ of the electric field is calculated from the experimental power spectrum of the fundamental pulse $I(\omega)$ using $|E(\omega)|=I(\omega)^{0.5}$. To simulate the experimental results, a double Fourier Transform method is used. The electric field in the time domain $E(t)$ is calculated as the Fourier image of the complex spectral amplitude in the spectral domain, with the formula $$E(t)=\int |E(\omega)| \exp[i\phi(\omega)]\exp(-i\omega t)d\omega, \qquad [4]$$

where the spectral phase $\phi(\omega)$ is the function that is introduced by the SLM. The power spectrum of the SHG is calculated using $$I_{SHG}(\omega)=|\int E(t)^2 \exp(i\omega t)dt|^2. \qquad [5]$$

The SHG amplitude is normalized using the maximum of the SHG intensity calculated for TL pulses, $\phi(\omega)\equiv 0$.

A simple evolutionary learning computer program (hereinafter "ELC") is programmed and it assumed a Gaussian electric field $|E(\omega)|$ corresponding to a 10 fs pulse centered at 800 nm. Eight points are used to represent each pixel in order to simulate more closely the experimental resolution of our setup. The second harmonic intensity is calculated according to $$I_{SHG}(2\omega_c)=|\int E(\omega_c-\omega)E(\omega_c+\omega)d\omega|^2 \qquad [6]$$

normalized to the maximum SHG amplitude for TL pulses.

Binary phase shaping (here in after BPS) simplifies the calculations, especially if it is assumed the amplitude of the electric field to be a constant, that is, the spectral power is set equal to 1 in the allowed spectral region. Each spectral component of the electric field, linearly dispersed in the frequency domain, can be represented as a binary value ($\pm 1$) determined by $b_k=\exp(i\phi_k)$, for $\phi_k=0$ or $\pi$ respectively. The intensity of the SHG signal measured at frequency $2\omega_k$ can be calculated with the formula $$S_k = \frac{\left|\sum_{j=0}^{N} b_{k-j} b_{k+j}\right|^2}{N^2} \quad [7]$$

where the integral in Equation 6 is now replaced by a discrete sum, N is a parameter that depends on details of the model such as number of pixels. The problem of spectral selectivity can now be formulated as finding a vector $b_k$ such that $S_k=1$ for $\omega_k=\omega_C$ and $S_k$ is minimized at all other frequencies.

In principle, the solutions found are members of the set of solutions that could be obtained by arbitrary phase and amplitude pulse shaping. For a pulse shaper with N pixels, one can generate $(P*A)^N$ shaped pulses, where P and A are the number of different phases and amplitudes a pixel can take. If it is assumed 100 pixels, each taking 10 different amplitude values and 100 different phase values, the number of different pulses is of order of magnitude $10^{300}$. This number is extremely large, therefore, while in principle, the field exists to achieve the desired photonic transformation or excitation, finding it is a great challenge.

The periodic nature of electromagnetic waves results in a great deal of redundancy in pulse shaping because nonlinear optical processes do not depend on the absolute phase or a linear variation of the spectral phase. This equivalence is expressed by $\phi\Leftrightarrow\phi(\omega)\pm a+b\omega$, where a and b are constants. This redundancy is filtered out by programming an ELC that works on the second derivative of the phase. The actual phase that is used in the SLM is obtained by integration setting a=b=0. An ELC was used to optimize smooth phase functions for spectral narrowing, but could not obtain a contrast ratio greater than unity.

The advantage of BPS is that computational redundancies are greatly reduced. For BPS and 128 active pixels the search space is reduced to $2^{128}$. If there is two-fold symmetry, for example two-photon excitation, then the number is reduced to $2^{64}$. The final search space is of size $10^{19}$, a number that is at least 281 orders of magnitude smaller than would be considered for arbitrary phase and amplitude pulse shaping as discussed above. The resulting space is small enough that all possible outcomes could be computed, and a large portion evaluated experimentally. A simple ELC, such as the one used here can quickly converge towards significantly improved solutions.

BPS has significant technological advantages. A retardation equivalent to $\pi$ is easy and fast to obtain and calibrate. Permanently etched masks can be made in advance and used for specific applications such as selective two-photon microscopy. Scanning the mask can yield two-photon excitation spectra. Laser control, especially with two-photon transitions, can be addressed with binary phase shaping. BPS makes it simple to analyze the problem and to propose rational solutions, as demonstrated here with a phase mask fabricated by the quasi-random gaps between prime numbers. Thus, a simple ELC is used to improve on the proposed solution efficiently because of the greatly reduced search space.

Multiphoton Intrapulse Interference

A multiphoton intrapulse interference phase scan (hereinafter "MIIPS") system and method of the present invention characterize the spectral phase of femtosecond laser pulses. The phase across the spectrum of an ultrafast pulse can affect the multiphoton process in a number of ways. Phase can increase the pulse length and hence reduce the peak intensity of the pulse, thereby preventing saturation, a common result under high intensity excitation. Phase can also be used to synchronize changes in the electric field with intramolecular wave packet dynamics. Finally, phase can be used to cause interference in the way multiple frequencies combine to achieve multiphoton excitation.

The technique of Multiphoton Intrapulse Interference (hereinafter "MII") and its application to control multiphoton processes is based on rationally designing an electric field required to achieve an articular target with a minimum number of parameters. The method is further based on calculating the amplitude of the nth-order electric field and comparing it to the absorption spectrum of the molecules being controlled. This provides a strong physical understanding of the control process, which can be very useful in the interpretation of experiments where the field is optimized by computer programs based on evolutionary learning or similar methods.

Two-photon transitions can focus the energy from an ultrafast pulse into a narrow frequency distribution; just like Fresnel diffraction can be used to construct a focusing lens. Conceptually, MII takes advantage of the interference term that is associated with the phase of each frequency vi within the pulse that contributes to the multiphoton process and can enhance or what may be as valuable, suppress a multiphoton transition. The effective electric field that drives the two-photon process through the induced (nonlinear) polarization is proportional to $E^2(t)$ (in the absence of intermediate resonance at the one-photon level). Its Fourier transform $E^{(2)}(v)$ determines the frequency response at the two-photon level.

Multiphoton Intrapulse Interference Phase Scan is capable of both pulse characterization and compensation of subsequent pulses. Within minutes, the pulses are characterized and compensated to yield transform-limited (TL) or user-specified shaped pulses at the sample. This capability is extremely practical and can be incorporated in any laser setup.

MIIPS is a single-beam method that does not require an interferometer. To make a precise and accurate measurement of the spectral phase using MIIPS, a known phase delay is imposed on the frequencies that make up the pulse using a calibrated pulse shaper. The pulse shaper essentially behaves as two back-to-back spectrometers. In one embodiment, the pulse is dispersed with a prism and collimated with a 200-mm concave mirror. At the Fourier plane, where all the frequencies are isolated, their phases are manipulated by a computer-controlled LCD spatial light modulator (SLM). The SLM applies the reference phase function to the input pulse, and the resulting pulse is then reconstituted to the time domain by a second concave mirror and prism. The SLM can be updated every pulse (presently limited to 1 kHz). The LCD has a 250-ms response time, so in principle it can be updated at 4 kHz. The output beam is analyzed by placing a 0.01-mm-thick beta barium borate SHG crystal in its path, usually at the place where optimum pulses are required. In a sense, the pulse autocorrelates itself at the SHG crystal. For each reference phase function that is introduced by the computer-controlled SLM, the output spectrum from the SHG is dispersed in a spectrometer and recorded.

Pulse characterization involves the introduction of a reference phase-modulation function of the form $\Phi = \alpha \cos(\gamma\Omega - \delta)$, where $\alpha$ is the magnitude of the phase delay, $\gamma$ is the periodicity $\Omega$ is the frequency detuning from the carrier frequency of the pulse, and $\delta$ is the position in the spectrum at which the cosine function is equal to one. The reference phase function, with typical values $\alpha = 2\pi$, and $\gamma$ =pulse duration, is programmed into the SLM and scanned for different values of δ ranging from 0 to 2π. For each value of δ, the spectrum of the frequency-doubled pulse changes, achieving a maximum in the spectral region over which the SLM compensates for the phase distortions. The MIIPS trace corresponds to the collection of spectra as a function of δ. MIIPS-generated trace of wavelength as a function of δ shows changes in the SHG spectrum of the laser pulse intensity. In general, the distance between the diagonal features is proportional to linear chirp and the angular deviation is proportional to quadratic chirp. Computer analysis of the trace is used to retrieve the spectral phase of the input pulse.

Qualitatively, the distance between the diagonal features determines linear chirp while the angle between the features determines the quadratic chirp. The full quantitative determination of the spectral phase can be obtained by double integration. Once the MIIPS system has characterized the pulse and retrieved the phase distortions inherent to the pulses, it can use that information to drive the SLM such that it compensates for the distortions. The first step in compensation is to take the phase determined from the first scan and program it into the SLM with a negative sign so that it subtracts the distortions. The system carries out a new phase scan to determine the remaining spectral phase modulation (usually about 10% of the original). Typically, three such iterations will yield transform-limited pulses. Because the laser is not focused in the pulse shaper, the method can be used with pulses that are relatively high in energy. Pulses ranging from about 100 pJ to about 10 mJ and pulse durations from less than 5 to about 500 fs can be used. Once the pulses are compensated (transform-limited), the laser can be focused to produce peak intensities from about $10^{12}$ to about $10^{18}$ W/cm$^2$, depending on the input energy.

This single beam method is capable of retrieving the magnitude and sign of second and third order phase modulation (in other words, linear and quadratic chirp) directly, without iteration or inversion procedures. MIIPS achieves accurate phase retrieval from chirped ultrashort pulses. For MIIPS, no synchronous autocorrelation, beam splitting, or time delays are required because the second harmonic spectrum depends on the relative phases of all frequencies within the pulse. The amplitude of the pulse is obtained directly from a spectrometer in a communications receiver. In order to precisely determine the phase of all frequency components in a pulse from a fs laser 123 (see FIG. 4), a pulse shaper is employed to introduce a reference phase function designed to yield this information directly. The shaped pulses are frequency doubled by a thin SHG crystal 507 (see FIG. 4) and the output is directed to spectrometer 503.

In addition to laboratory testing and specimen optic distortion analysis, the MIIPS system and method employing this single shot construction can also be applied to some communication situations in order to add considerably more encoded information into each pulse phase to supply additional encoding variables.

The MIIPS method is based on the principle that second harmonic generation, as well as other nonlinear optical processes, depend on the phase function φ(ω) across the spectrum of the laser pulse. The phase function can be expanded in a Taylor series around carrier frequency Ω=ω-ω₀ as follows:

$$\phi(\omega)=\phi(\omega_0)+\phi'(\omega_0)\Omega+\frac{1}{2}\phi''(\omega_0)\Omega^2+\frac{1}{6}\phi'''(\omega_0)\Omega^3+\ldots, \quad [8]$$

where the first two terms provide only the relative (common) phase and a time delay, respectively. Only the third and higher terms are responsible for phase distortion. These higher terms are retrieved in MIIPS by superimposing a reference phase function on the pulse to obtain, $$\phi(\Omega)=\alpha \cos(\gamma\Omega-\delta)+\phi(\Omega) \quad [9]$$

where the first term is the reference phase function introduced by the shaper with maximum phase amplitude α, period γ and the absolute position in the spectral window δ. φ(Ω) is given by Equation 8.

The maximum SHG signal as a function of Ω is obtained when $d^2\phi(\Omega)/d\Omega^2=0$. A parameter in the reference phase function can be varied to obtain a plot from which the phase distortions (φ", φ'''.) can be obtained in the laser pulse. The maximum signal in a (wavelength, δ) MIIPS trace describes a series of lines given by $$\delta_{max}=\delta_0+(\lambda_{max}-\pi c/\omega_0)\omega_0^2/(\pi c)\{\gamma-\phi'''/(\alpha\gamma^2 \sin \delta_0)\} \quad [10]$$

where $\delta_{max}$ is the position where maximum SHG signal is obtained, $\delta_0=\arccos[\phi''/(\alpha\gamma^2)]$, and $\lambda_{max}$ is the position of the maximum SHG signal.

A complete data set, from which a phase function can be retrieved, consists of a series of spectra obtained as a function of the parameter δ. First the data is fit to a series of lines which follow $\lambda_{max}(\delta_{max})$ as expected from Equation 10. The quadratic phase modulation (responsible for linear chirp) is determined directly from the distances $x_1$ and $x_2$ between the SHG maxima, according to $$\phi''=\alpha\gamma^2 \arcsin[(x_1-x_2)/4]. \quad [11]$$

Note that the magnitude and sign of φ" are obtained directly from the MIIPS trace. Furthermore, the accuracy of the measurement can be improved for small phase distortion by decreasing the reference phase function parameters αγ².

The cubic phase modulation (quadratic chirp) is determined by the slope Δδ/Δγ that the maximum SHG features make in the Δδ plane. Analytically, cubic phase modulation is given by $$\phi'''=0.5 \alpha\gamma^2\pi c/\omega_0^2 \cos[(x_1-x_2)/4]\{(\Delta\delta/\Delta\gamma)_{0.1}-(\Delta\delta/\Delta\gamma)_2\}, \quad [12]$$

where the slopes are measured in nm$^{-1}$. Higher order phase distortions, such as self-phase modulation and quadratic phase components can be obtained from the curvature of the line defined by the maximum SHG response. The MIIPS can be programmed to find the phase distortions on the laser pulses directly by double integration and to introduce a compensation phase function that eliminates the distortions. This mode of operation can be used to find arbitrary phase deformations and yield transform limited pulses, which in a MIIPS scan look like straight parallel lines separated by π. The fit to the experimental data is given by Equation 10, and the phase parameters are extracted with Equations 11 and 12.

Figure 4:
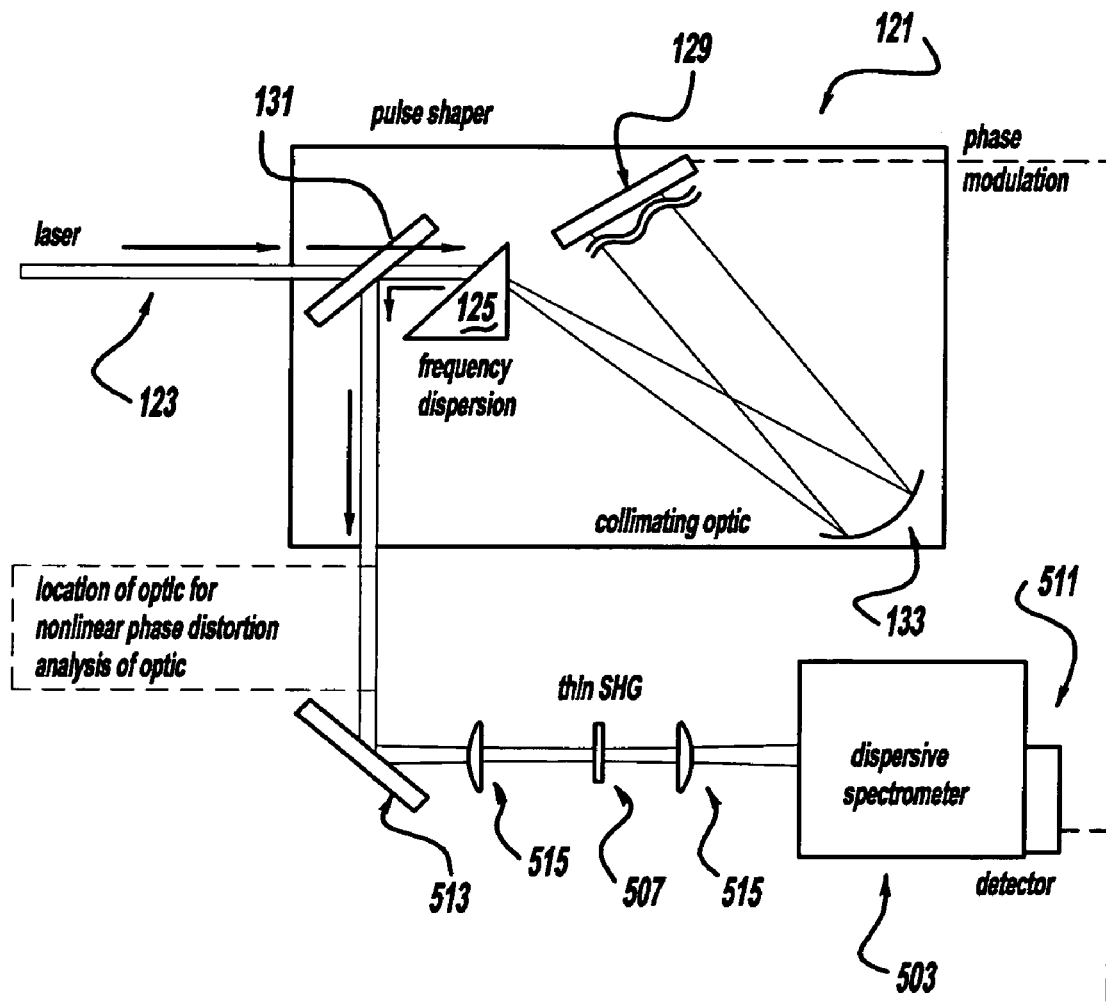
FIG. 4 is a diagrammatic view showing a second preferred embodiment of the present invention that employs MIIPS.
Figure 4:
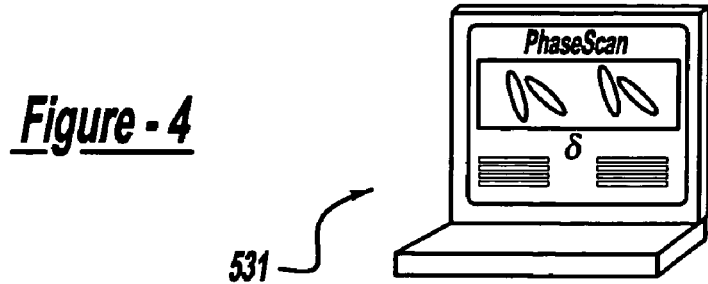

The version of MIIPS illustrated in FIG. 4 uses a thin SHG crystal 507, spectrometer 503, spatial light modulator 129 and a femtosecond laser 123. A fs laser pulse is preferred but, for test data disclosed herein, 50 fs pulses from a regeneratively amplified Ti:Sapphire laser are employed wherein the pulse energy is attenuated down to ~5 μJ. For the test data herein, A 0.3 mm βBBO type I crystal is used for SHG 507 and the output is attenuated and directed to spectrometer 503 with a cooled CCD detector 511. System 121 further has a redirecting mirror 513, two quartz cylindrical lenses 515 (200 mm focal length, the upstream one for focusing and the downstream one for collimating). For the tests, a spatial light modulator was used for pulse shaper 129 consisting of two 128 LCD elements (which can be obtained from CRI Inc. as model number SLM-256). For the test, the pulse shaper is carefully calibrated to provide accurate phase delays (better than one degree) with no changes to polarization or amplitude. The phase distortions used to obtain the data are generated at the pulse compressor after regenerative amplification. In another variation, self-ultrafast switching is based on pulse phase modulation in the pulse shaper, the thin SHG crystal causing multiphoton intrapulse interference, dispersive optics, and a CCD camera detector. The simplicity and accuracy of this method make it practical for the evaluation of laser pulses close to transform limit and for the evaluation of phase distortion from optical elements.

Multiphoton intrapulse interference is not just about focusing the energy. The goal is to determine the field that the molecules experience. The control of nonlinear optical processes, using multiphoton intrapulse interference can be applied in diverse fields such as photochemistry, communications, and medicine.

The present invention provides a system and method to characterize the spectral phase of femtosecond pulses. This single beam method is capable of retrieving the magnitude and sign of linear and quadratic chirp with high resolution. Pulse retrieval is based on analytical expressions that yield the phase distortion, without iteration or inversion procedures. Linear and quadratic chirp values, and to some extent cubic chirp values, are important because there are knobs on the laser that can be used to correct for this distortion by mechanically adjusting the grating spacing in the laser beam amplifier compressor. The method can be used with very short pulses. This adjustment can be automatically controlled with the computer controlled software as disclosed in FIGS. 16-19, as discussed in greater detail hereinafter. The method is very versatile, and can be used with high or very low intensity pulses for any wavelength for which low cost, off-the-shelf SHG crystals exist. MIIPS can also be used by obtaining third or higher order harmonics in gases. The maximum signal agreement with equations further makes the method useful for the characterization of pulses in wavelength regions for which SHG crystals are not available. In summary, uses of MII and MIIPS are as follows:

- MII can be used to make self-switching pulses as long as they undergo one non-linear optical process, such as SHG, sum frequency generation, difference frequency generation or four-wave mixing;
- MIIPS can be used to allow automated laser optimization, specifically quadratic and cubic phase distortions;
- MIIPS can be used for pulse characterization of arbitrary phase distortions;
- MIIPS can be used to measure the phase modulation induced by optical elements and similarly it can be used to measure the thickness of a substrate;
- MIIPS can be used for decoding information (address and/or message) stored in the phase;
- Shapers operating to optimize the MII phenomenon can encode self-decoding messages;
- MII can be used to prevent three photon damage of DNA from fs pulses; and
- MII can be used to optimize the selective activation of PDT agents specifically at a particular depth, avoiding collateral damage.
- MII can be used to cause selective nonlinear optical excitation.

An automated pulse chirp determination for arbitrary smooth phase distortions is based on the use of a pulse shaper and obtaining a phase scan, wherein the spectrum of the SHG is a function of phase parameter $\delta$ for $\phi(\omega)=\alpha \cos(\gamma\omega+\delta)$. This method is non-iterative and it directly obtains the desired values without evolutionary learning calculations. Therefore this method is very stable and does not depend on overlap between two pulses in space and time. Moreover, the pulse analyzes itself in a thin SHG crystal. It should be appreciated that BPS, MII and MIIPS may be advantageously used to improve the performance of any of the end uses disclosed herein, including MALDI, sequencing, cleavage, control of nonlinear optical processes, photopolymerization, quantum computing, OCT, PDT, selective nonlinear optical excitation, spectroscopy, microscopy and communications.

Second-Harmonic Generation with Powders

Chemical powders, adhered onto transparent quartz carriers, are employed in place of thin SHG crystal optic component. The powder embodiment is presently preferred to significantly reduce cost in high energy (for example, one nanojoule or greater) applications such as for MIIPS, nonlinear optical characterizations and FROG analysis. The chemical powder is preferably a collection of small crystals of Potassium Dihydrogen Phosphate (KDP or KD*P, which can be obtained from Sigma-Aldrich Inc. as Code No. OPP076413)) and deuterated potassium dihydrogen phosphate, or alternately including Beta Barium Borate powder and other materials with crystal structure that is non-centrosymmetric. One or more powder particle is glued onto a quartz substrate or alternately glass, microscope slide substrate using a silicone-rubber or cyanoacrylate ($C_5H_5NO_2$) adhesive. Alternatively, the powder can be compressed into a pellet. Each powder particle size can be 1 to 1,000 microns and preferably is between about 0.5 to 20 microns per side, depending on the focusing length, intensity of the laser and the sensitivity of the detector. The significant cost benefits can be achieved as long as each powder particle is less than 1 $mm^3$. This avoids the conventional need to grow and then machine or polish accurate angles onto larger sized, non-powder particles. For microscopy, even smaller particles can be employed as long as a very sensitive detector is used. Furthermore, the powder approach is advantageous by having large variety of random crystal orientations therein which creates improved average results for laser pulses shorter than 20 fs which is ideally suited for MIIPS where some beam pulse scattering is acceptable. The SHG output can be collected after transmission or the diffuse SHG signal can be collected as it reflects from this optic. While SHG optic use is preferred, the powders of the present invention may be employed with other optics such as mirrors, lenses or the like.

Figure 30:
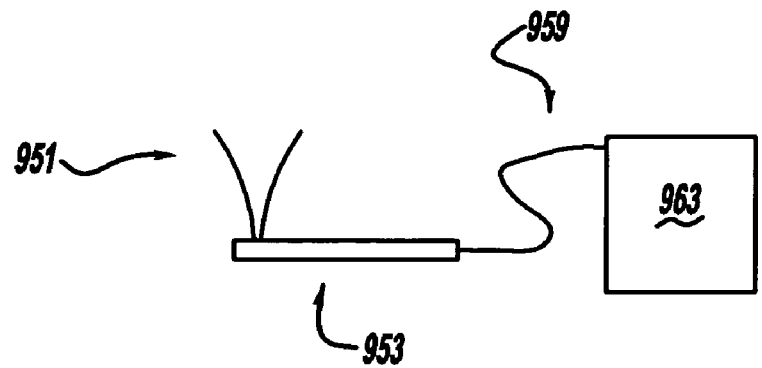
FIGS. 30 and 31 are diagrammatic views showing a detector with a powder optic employed in an alternate embodiment of the present invention.
Figure 31:
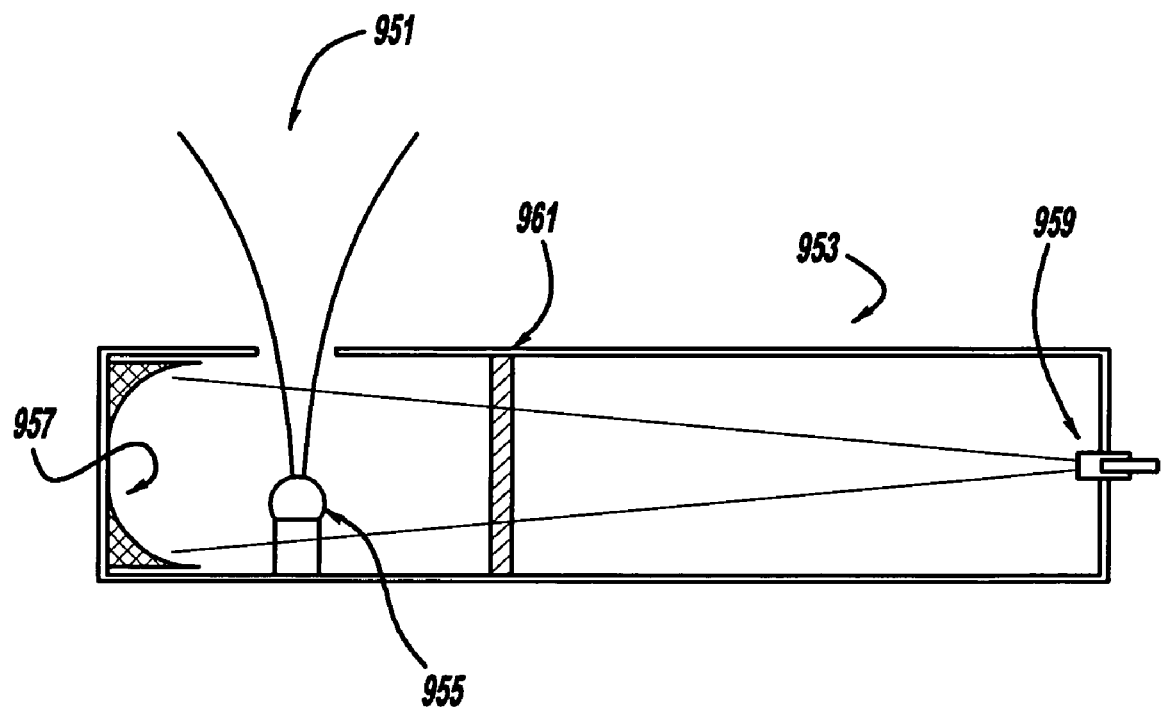

An alternate embodiment of a powder optic can be observed in FIGS. 30 and 31, employed in a MIIPS detector. A laser 951 is focused on the (pencil-like) portion 953. Inside of this portion there is a pellet or particle 955 of frequency doubling powder. The powder contains micro-crystals (for example, a size smaller than 1 mm, but preferably smaller than 50 microns) of non-centrosymmetric compounds such as Potassium dihydrogen phosphase, beta-barium borate, lithium borate, or lithium iodate. The laser light gets frequency doubled at these crystals. The diffuse frequency doubled light is collected by concave mirror 957 and focused on an optical fiber 959 after transmitting through an optical filter 961 that transmits that light but not the fundamental light of the laser. The pulse is then transmitted to a compact spectrometer 963.

MALDI

Figure 2:
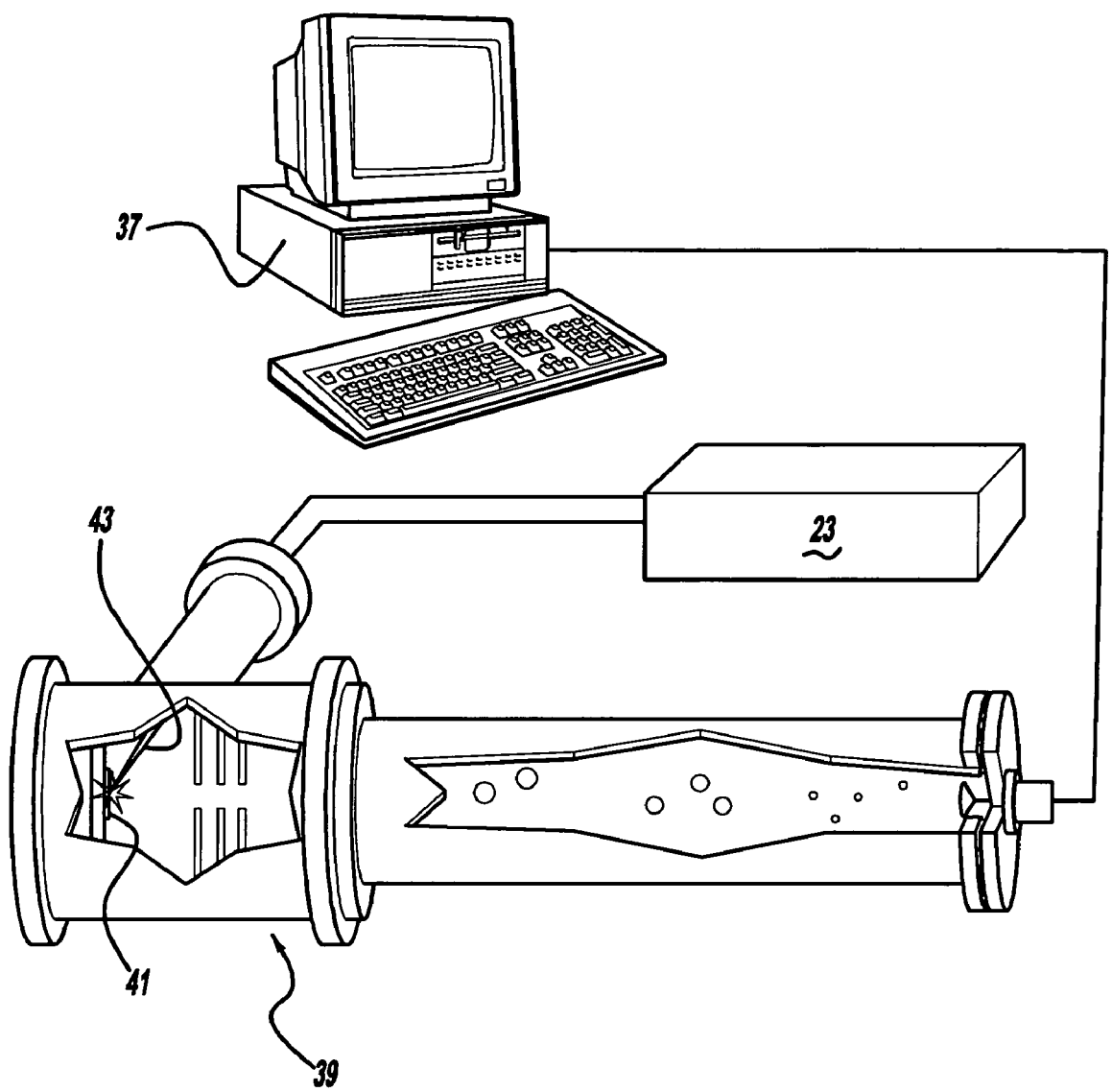
FIG. 2 is a diagrammatic view showing the first preferred embodiment used for MALDI.

Another embodiment of the present invention for use with a matrix-assisted laser desorption ionization (hereinafter "MALDI") device 35 is shown in FIG. 2. More specifically, the MALDI device provides a time-of-flight mass spectrometer ("TOF MS") 39. A sample or specimen 41 to be analyzed is placed within mass spectrometer 39. Bursts or pulses of a laser beam 43 are emitted from laser 23, through the optics 25, 27, 31 and 33 (also see FIG. 1), as well as through pulse shaper 29, and onto specimen 41; this causes fragmentation and ionization of a top layer of the specimen for detection and sensing by mass spectrometer 39 for further evaluation, analysis, comparison and subsequent control by personal computer 37.

A VESTEC 2000 MALDI TOF mass spectrometer is believed to be suitable for this invention, although most commercial MALDI instruments can be adapted with the femtosecond laser, pulse shaper and feedback learning control method described herein. During extraction, all of the ions obtain the same energy in the 30-kV ion acceleration region, and because K. E. $=\frac{1}{2} mv^2$, the lightest ions achieve the highest velocity and, thus, reach the detector first. This transient (for example, having a duration of 300 microseconds) mass spectrum is recorded by a transient recorder at the detector. It is common practice to sum many (10-100) of this transient mass spectra to produce a sound spectrum from an ion-counting statistics criterion.

After the initial laser desorption pulse plume is generated, an additional ionization and fragmentation pulse brings about significant increases in signal ions in the specimen. The use of a second laser pulse with femtosecond duration for post-desorption/ionization excitation enhances sensitivity and provides some amino acid-specific fragmentation. Therefore, the present invention laser source is based on a pair of ultra-short, less than 50 femtosecond laser pulses, one for desorption/ionization of analyte molecules and the second for selective-fragmentation. Alternately, the first laser may be a nanosecond pulse used for desorption followed by a femtosecond pulse to be used for selective bond cleavage. A single laser method would be possible when the source for the molecular (for example, protein) ions is an electro-spray source which provides the gas-phase protein ions without a matrix.

The desorption beam is the fundamental at 800 nm, the second harmonic at 400 nm, or the third harmonic at 266 nm. The desorption beam can also be derived from the pump YAG laser at 532 nm or at 266 nm. No desorption laser is required when an electro-spray source is employed. Additionally, controlling the delay between the desorption and the shaped laser pulses can also serve as a parameter for control when using MALDI.

In a first variation of the present embodiment, learning feedback software can be employed in the present invention control system and apparatus as a preliminary investigation method for analyzing a pre-test unknown sample or specimen. For any new system, the test should start with pre-defined pulse shapes in order to obtain a basic understanding of the system. Among the pre-defined pulses, the shortest pulse is expected to ionize molecules on the surface of the sample with minimum decomposition, the longest pulse is expected to mimic the nanosecond experiments where the singly protonated protein may be observed. It is also noteworthy to vary the delay between two laser pulses from a few picoseconds to a few nanoseconds in order to appreciate the time scales involved. Manual inputs will be initially performed by the system operator or user through entering input data into the personal computer. The microprocessor within personal computer 37 will then control laser 23 by receiving an essentially real time feedback input signal from mass spectrometer 39 and then perform calculations, comparisons and evaluations. These automated steps can be substituted with manual user calculations and decisions if desired based on personal computer outputs.

The objective of the software routine is to aid in the selection of sample targets for further testing iterations for subsequent criteria data input. An optional alternate embodiment subroutine includes shooting long laser beam pulses then quick short laser beam pulses, with a separation set by an optical delay of less than ten nanoseconds. The short pulse of approximately 50 femtoseconds is performed in order to look for fragmentation and the matrix mass. Laser beam pulses of between approximately ten and 100 picoseconds are performed to look for the parent mass. The ultrafast laser beam pulse durations employed with the present invention advantageously allow for approximately 1000 laser beam shots at a single sample or specimen without significant degradation of the specimen; this allows for quicker and less expensive usage of the apparatus while also encouraging statistically more accurate results. The long and short pulse combinations can be used in addition to or without the benefit of pulse shaping. Otherwise, the control system and apparatus are the same as discussed herein. The real time learning feedback method and computer software are employed to statistically optimize the repetitive identification of molecularly complex and unknown samples or specimens in a highly automated and relatively quick manner.

Once statistical convergence has been determined by the personal computer, then the test is complete by determining the optimum pulse characteristics (whether they be pulse shape, pulse duration or any other such variable laser beam characteristic) for the corresponding and now post-test identified specimen.

The time scale of some of the processes that occur during MALDI may be longer than the femtosecond pulses. In a first variation, the pulse shaper can be used to produce pulse sequences up to ten picoseconds apart. Optical delay lines can be used to increase this time delay in the nanosecond range if needed. In a second variation, the wavelength of the pulses being shaped is 800 nm. A second harmonic crystal is all that is needed to convert the wavelength to 400 nm, however, the shaper is capable of regulating the energy delivered to the sample without changing the carrier frequency (wavelength) of the laser.

In a second variation of the present embodiment, a complete set of binary phase functions is used to carry out an exhaustive evaluation of laser fragmentation. The resulting MS results will be analyzed for each binary phase. The resulting data will be mapped and each binary phase is evaluated for its ability to cause selective bond cleavage of post-translational modifications, disulfide bonds and peptide bonds. The goal of this approach is to find robust binary phase functions that can be used to cause selective bond cleavage. Exhaustive evaluation of binary phase functions is an efficient method for analyzing the search space of effective phase functions as will be discussed in greater detail hereinafter. A third variation of the present embodiment employs the previously discussed learning feedback software in combination with different binary phases. Controlling the delay between the desorption and the shaped laser pulses also serves as a parameter for control when using MALDI.

Protein Sequencing

Laser desorption mass spectrometry can be employed with the present invention for identification and protein sequencing. This is significantly enhanced and made possible by the ultra-fast laser pulses and learning feedback system used. The matrix has been shown to enhance the yield of charged protein for analysis by MS detection. The matrix:phosphor diester backbone interaction has been shown to play an important role. The use of liquid matrices such as glycerol and lactic acid for IR-MALDI may bring some additional flexibility to sample preparation and delivery to the MALDI instrument. The "Ladder Sequencing" method involves a partial Edman degradation with phenyl isothiocyannate and using phenyl isoccyanate as a terminating agent. Partial enzymatic hydrolysis of polypeptides using trypsin is another strategy for protein sequencing. Trypsin digestion attaches only bonds in which the carboxyl group is contributed by either a lysine or an arginine residue. Analysis of metastable species in matrix-assisted laser desorption ionization post-source decay (here in MALDI-PSD) using a reflectron TOF spectrometer leads to valuable structural information. The introduction of 'delayed extraction' in MALDI allows improved resolution, suppression of matrix background, reduction of chemical noise, and minimization of the effect of laser intensity on performance.

Figure 3:
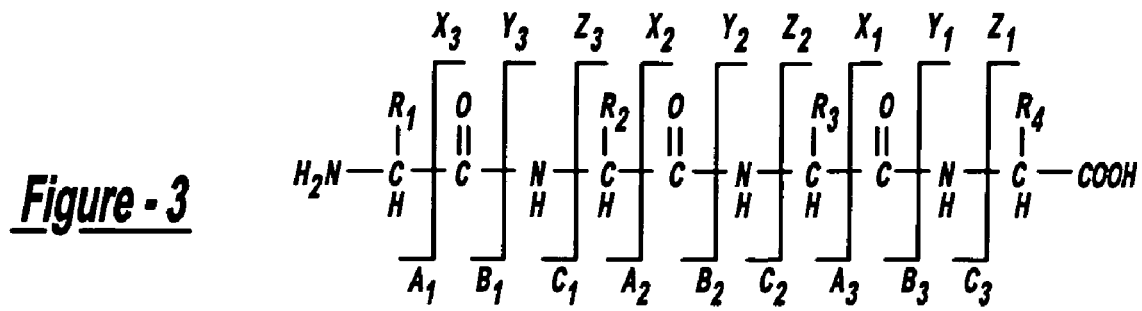
FIG. 3 is an exemplary molecular structure cleaved by the first preferred embodiment control system and apparatus.

MALDI is a soft ionization technique which produces protonated molecules that undergo very little or no subsequent fragmentation due to the low amount of energy imparted during the ionization process. Therefore, MALDI can be used to analyze mixtures of peptides because the mass spectrum of one peptide is unlikely to overlap with the spectrum of another. Ideally, cleavage of the ionized peptide at each peptide bond (and disulfide) would provide a mass spectrum that could be interpreted, using knowledge of the masses of the amino acid residues, to deduce the sequence. However, as conceptually illustrated in FIG. 3, cleavage on either side of the I-carbon is also possible to give fragment ions, which, while diagnostically useful, also complicate the spectrum. It is also noteworthy that cleavage at any designated bond can generate either an N-terminal ion (a, b, c) or a C-terminal ion (x, y, z), the predominance of which for a protonated peptide ($MH^+$) depends on the locus of the more basic residues. In reality, the fragmentation process is more complicated than suggested in FIG. 3; for example, creation of a y-ion involves hydrogen transfer from the N-terminal side of the peptide bond and retention of the ionizing proton. In addition, there can be fragmentation of the side chain on certain residues; for example, fragmentation involving cleavage at the $\theta$-carbon of leucine and isoleucine generates w-ions, which distinguish these two isomeric residues.

Recognizing the ion types as represented by the appearance of peaks in the mass spectrum is not critical, as most strategies for interpretation, especially those using an algorithm, involve an iterative computational approach. However, the beginning of a C-terminal series of fragments can be distinguished from the start of an N-terminal series. The largest b-ion will be represented by a peak at high m/z value that differs from that representing $MH^+$ by a number of mass units equal to the sum of the mass of an amino acid residue plus the mass of water due to expulsion of the C-terminal residue, which contains the hydroxyl group. On the other hand, the largest y-ion is represented at a high m/z value by a peak differing from that for $MH^+$ by a number of mass units equal to only the mass of an amino acid residue.

In principle, the sequence of a peptide is deduced from a mass spectrum in which a complete series of any given ion type are represented. In practice, however, a complete series of any one type is rarely observed, but in fortunate situations, overlapping patterns of two or more incomplete series may give complete sequence information. Ideally, one would prefer to observe complementary information from series of N-terminal and C-terminal fragment ions to bolster confidence in the analysis.

Consider the MALDI-PSD mass spectrum as an unknown. It can be assumed at the outset that the major peak at m/z 574 Da represents the protonated molecule, which was the precursor ion selected for PSD. The protonated molecules fragment during the PSD process and degrade into fragment ions. The procedure for analysis or data interpretation consists of merely examining the mass difference between each of the fragment ion peaks and the peak representing the protonated molecule. The goal is to find a fragment ion peak that differs in mass from the protonated molecule peak by either a residue mass or a residue mass plus water. A peak at a mass-to-charge (m/z) value that differs from the protonated molecule peak by the mass of a residue mass plus water corresponds to the amino acid that was located at the C-terminus of the original peptide.

The protein sequencing can be conducted by use of the present invention with or without use of a matrix. The use of an ultrafast, femtosecond laser is envisioned to minimize any destructive burning of the specimen, thereby potentially rendering use of an expensive and time-consuming matrix as unnecessary. Without a matrix (herein, also known as having "isolated molecules"), the identification and sequencing of the protein is simplified since the matrix characteristics do not have to be accounted for and filtered out of the calculations. A femtosecond laser in the range of approximately 20 femtosecond duration pulses allows for localization of the energy based on the speed of the pulse and the ability to quickly shape the phase and amplitude modulation of the pulse. Furthermore, the specimen fragmentation is primarily due to laser cleavage rather than enzyme or chemical cleaving. This is ideally suitable for insoluble proteins, glycocylated proteins which have been linked to cancer, (including the selective cleavage of the associated oligosacharides) direct protein analysis from silicate substrates, direct analysis of PAGE gels, direct sampling of membrane proteins from intact cells and bacteria, the direct sampling of genetically modified agricultural produce (such as grains), and even human matter such as hair, fingernails and fingerprints.

The personal computer employs a method and software for protein sequencing as follows. The foundation of this method is based on the fact that there are only 20 amino acids and that their masses are well known. First, the computer determines the molecular weight of the intact proteins specimen. This requires the generation of a single high-mass peak and minimization of the low weight background. Secondly, the computer automatically finds peaks that are an integer number of amino acids smaller than the parent protein; a laser beam pulse shape that causes some fragmentation can be employed. Thirdly, this procedure is continued from high to low masses. Finally, confirmation of results can be automatically obtained by a statistical optimization method (such as that previously described for the MALDI process) that attempts to optimize a given mass; the success of this optimization will depend on whether that fragment of the protein has an integer number of amino acids. Automatic adjustment for the N or C terminus is also automatically adjusted for by the computer as previously explained. Alternately, each single amino acid could be separately searched for. Thus, the present invention control system and apparatus is ideally suited for analyzing, identifying, sequencing and severing complex multi-molecular specimens in a highly automated manner.

Selective Bond Cleavage

The ultra-fast laser of the present invention is used to enhance in-source photochemistry and fragmentation, however, random fragmentation would not be as useful as selective bond cleavage. Furthermore, selective peptide bond cleavage would be ideal for protein sequencing. Cleavage of amino acid side chains may be of value for de novo sequencing because it would allow a determination of the presence or absence of certain amino acids. Similarly, selective cleavage of phosphate groups, oligosacharides and other post-translational modifications would be equally valuable. The ideal, of course, would be to achieve peptide bond cleavage without loss of side chains or other appended groups. This would allow, for example, to determine phosphorylation sites.

It is envisioned that selective bond cleavage can be realized when using shaped pulses that are capable of localizing the energy in a time scale that is short enough to prevent total energy randomization. For example, the protonated molecule of bradykinin potentiator C, as produced by MALDI, fragments poorly during PSD, and does not produce a suitable spectrum from which one could deduce the amino acid sequence. Thus, this 11-residue peptide is ideal for this application. Selective laser bond cleavage may have additional application as a synthetic route to specific products. Accordingly, the present invention provides a photonic scalpel to generate structurally diagnostic fragment ions, for example in proteins.

Control of Nonlinear Optical Processes

As applied to all of the applications herein, selective control of one and multiphoton processes in large molecules, including proteins, is possible using simple pulse shaping. The results show an extraordinary level of control that is robust and sample independent, with contrast ratios near two orders of magnitude (clearly visible with the naked eye). Such large contrast ratios allow for more precise cancellation control of undesired photons and other laser beam characteristics, such that nonlinear transitions induced by each pulse are controlled. Because simple phase functions can be incorporated into a passive optical component such as mirror having a fixed pulse shaping surface (for example, a set of 800 nm wavelength sine curves) these applications do not require the complexity and expense of computer controlled pulse shapers after initial set up, although systems such as in FIG. 1 can still be employed.

Figure 12A:
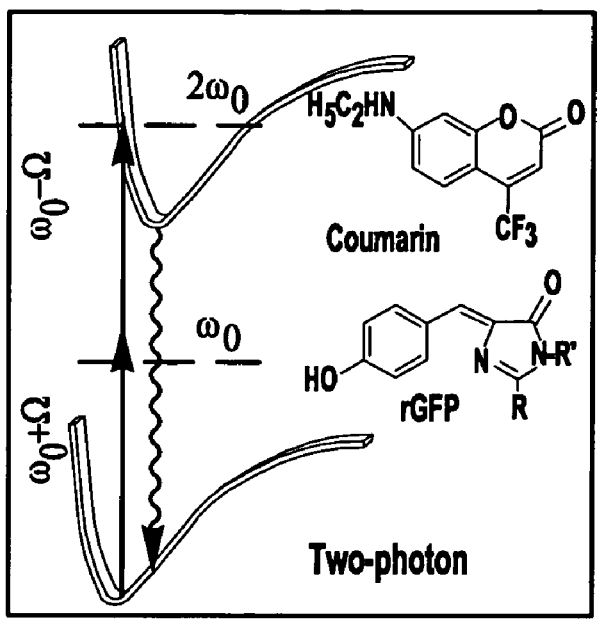
FIGS. 12a through 12c are schematic and graphical representations of two photon and three photon induced fluorescence employed with any of the embodiments of the present invention.
Figure 12B:
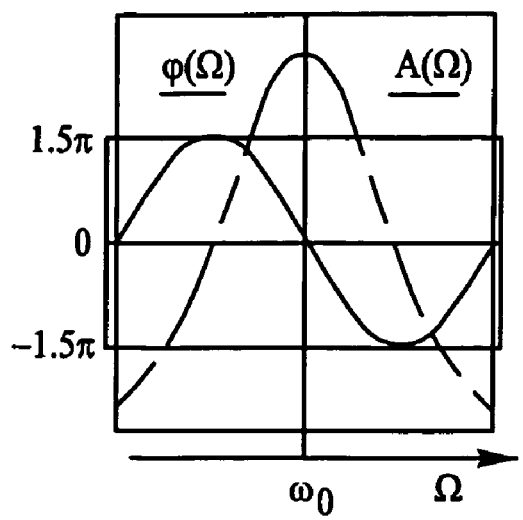
Figure 12C:
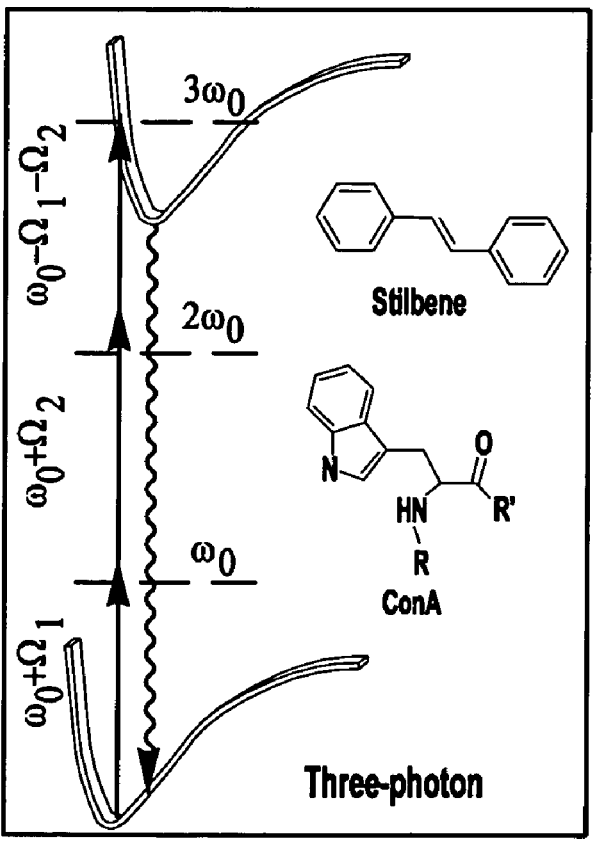

The underlying concept of the apparatus and associated method are shown in FIGS. 12a-12c. Multiphoton transitions are optimized when the central bandwidth of the laser pulse $\omega_0$, is some fraction (half for two-photons, a third for three-photons, etc.) of the total energy of the transition as illustrated in FIGS. 12a and 12c. For ultrafast pulses, when the bandwidth is large, different frequency components ($\omega_0 \pm \Omega$) of the pulse can interfere, thereby reducing the probability for multiphoton excitation. Referring to FIG. 12b, the spectrum of the ultrafast laser pulse with amplitude $A(\Omega)$ is plotted as a function of detuning from the central frequency. A phase mask $\phi(\Omega)$ can be imprinted on the pulse such that the phase of each frequency component $\Omega$ acquires a specific value. The effect of pulse shaping on the probability for two-photon absorption ("2PA") can be calculated as follows:

$$P_{2PA} \propto \left| \int_{-\infty}^{\infty} A(\Omega) A(-\Omega) \exp\left[i\{\varphi(\Omega) + \varphi(-\Omega)\}\right] d\Omega \right|^2 \quad [10]$$

and for three-photon absorption ("3PA"), a similar formula can be derived as follows:

$$P_{3PA} \propto \left| \int_{-\infty}^{\infty} \int_{-\infty}^{\infty} A(\Omega_1) A(\Omega_2) A(-\Omega_1 - \Omega_2) \right. \quad [11]$$

$$\left. \exp\left[i\{\varphi(\Omega_1) + \varphi(\Omega_2) + \varphi(-\Omega_1 - \Omega_2)\}\right] d\Omega_1 d\Omega_2 \right|^2$$

where amplitudes and phases are introduced for two different detuning values $\Omega_1$ and $\Omega_2$, as shown in FIG. 12c. One photon transitions are not affected by the phase of the pulses, however, one photon processes are difficult to selectively achieve at high photon flux due to the onset of multiphoton processes.

A schematic representation of two photon and three photon induced fluorescence is illustrated in FIGS. 12a and 12b, respectively. The vertical arrows represent ultrafast pulses that induce the two and three photon transitions. Because of their broad bandwidth, ultrafast pulses contain photons that are detuned from the central wavelength $\omega_o$ by an amount $\Omega$. Referring again to FIG. 12c, ultrafast laser pulses are shaped using a sine function phase mask across the pulse spectrum underlying the dashed curve while the structures of the chromophores are also shown.

Multi-Photon Microscopy

Figure 5:
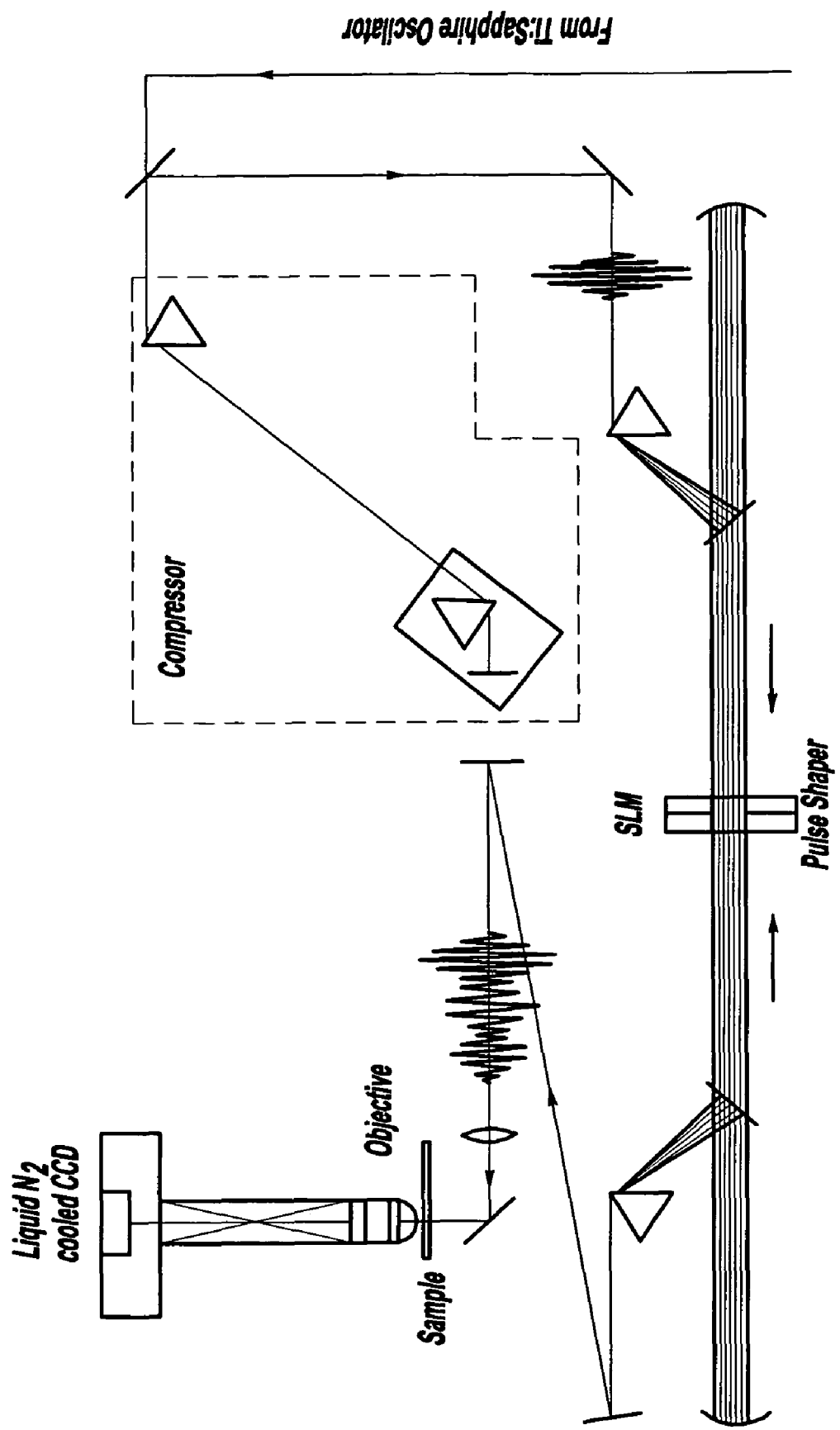
FIG. 5 is a diagrammatic view of a third preferred embodiment of the present invention applied to multi-photon microscopy.

Two-photon microscopy provides significant possibilities for fluorescence imaging and photochemistry. It offers attractive advantages, including higher resolution, background-free signal, lower background scattering, better penetration in thick samples, and reduced photon-induced damage, which arise from the basic physical principle that the absorption depends on the square of the excitation intensity. Reference should be made to FIG. 5. Two-photon microscopy is amenable to multiple-probe staining, whereby two-photon transitions excite different probe molecules that emit at different wavelengths, and for functional imaging of living cells. Phase-modulated femtosecond pulses can selectively excite one type of probe molecule only, leaving the others in their ground state. Multiphoton excitation is achieved by multiphoton intrapulse interference (MII) and this can be accomplished efficiently using binary phase shaping. Selective excitation is used to enhance contrast and achieves functional imaging of samples stained with fluorescent probes sensitive to their microscopic chemical environment.

Selective excitation with significant contrast ratios has been achieved here by optimizing the overlap between the power spectrum of $E^2(t)$ and the two-photon absorption spectrum. The addition of a computer-controlled pulse shaper to the multiphoton microscope provides a number of important advantages. First, the pulse shaper is used to compensate unwanted phase distortions at the sample. Linear chirp, for example, has been shown to reduce signal intensity in two-photon microscopy. With a pulse shaper, linear, quadratic, cubic and higher order chirp is compensated to obtain the most efficient excitation. Second, the pulse shaper is used to control the output spectrum of the laser pulses by amplitude modulation. Third, the pulse shaper is used for selective probe excitation. Because the spectrum of the laser remains constant, phase modulation does not affect one photon processes such as absorption, reflection and scattering. Selective excitation minimizes possible cross talk between different fluorescent probes in the sample. Finally, the pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens.

This method can be used to selectively excite either different probe molecules or identical probe molecules in different environments. In addition, this method can be used for selective excitation of luminescent probes such as quantum dots, metallic nanoparticles, and single molecules. The same principle can be extended to achieve functional imaging of semiconductor microchips by two-photon laser induced conductivity. Having a pulse shaper for multiphoton microscopy provides the flexibility of selective probe excitation or maximum signal enhancement by controlled modulation of the spectral phase of the femtosecond pulses. Even when for fluorescent labels with very similar absorption spectra, pulse shaping is shown capable of selective excitation. This level of selective excitation and enhancement can be adapted to different modes of two-photon and three-photon microscopy.

Multi-Photon Photo Polymerization

Microlithography involves the use of UV light to initiate polymerization. Two-photon induced polymerization has the advantage that it permits 3D polymerization of smaller features (down to 100 nm). Photonic band gap materials (hereinafter "PBGM") are 3D constructions with features similar to the wavelength of light that exhibit very interesting behavior. Two-photon microlithography is one convenient method for the preparation of very sophisticated PBGMs.

Two-photon absorption can be used in three-dimensional lithographic microfabrication (hereinafter "3DLM") through two-photon-induced polymerization (hereinafter "TPIP"). This is due to the fact that simultaneous two-photon absorption requires a very high photon flux, which is only present at the point of the focus. Thus the TPI polymerization is confined to the focal volume. This high spatial resolution contributes to the ability of TPIP not only to scan the laser in the x and y direction but also to change the focal plane (z) without overwriting existing features. Therefore, 3DLM is obtained by a single processing step. 3D polymeric structures include a photonic band gap structure, waveguide structures and a micro-channel structure. It is envisioned that multiphoton intrapulse interference can be advantageously used to enhance this non-linear photopolymerization.

In contrast, currently, two-photon microlithography and related techniques can only initiate one type of polymer. If two different types were needed, one would need to rinse, change the monomer mixture, find the position of the feature with nanometer accuracy, and make the new feature.

In one embodiment, BPS is used in microlithography and related techniques such as micromachining and microfabrication to control the polymerization of two different polymers. Being able to alternate two different polymers allows greater flexibility in the construction of nanometer features such as, but not limited to, microelectromechanical systems (hereinafter "MEMS"). Controlling the deposition of two different polymers is enabled by the control of what wavelength two-photon excitation takes place.

Quantum Information Processing

One such important application of the concepts of coherent control is emerging in the area of quantum information processing. The selectivity in excitation, which is offered by shaped laser techniques, may also serve as the building blocks for the development of the first practicable quantum computer. In a prior optical scheme for quantum computing, computer controlled pulse shaping where information storage and retrieval through quantum phase is required. In case of an eight-state Rydberg atom wavepacket, the prior scheme can store information as a quantum phase in one or more flipped state, which could be subsequently retrieved in a single step in agreement with the Grover's; this prior scheme is disclosed in J. Ahn, et al., Science 287 (2000), p. 463; and N. Bhattacharya, et al., Phys. Rev. Lett. 88 (2002) 137901-1.

A typical visualization of a traditional quantum computer network would have nodes consisting of quantum storage devices, where information can be stored for very long times either in ground or in some metastable excited states of atoms, molecules or ions. The quantum information can be transferred from one node of the network to the other using photons. The nodes would carry out the required computations and also serve as a storage or memory unit. The storage time is limited by decoherence time. Transferring quantum information between the two nodes without allowing for decoherence is very difficult. There are already some proposals in quantum communication to transmit and exchange quantum information between distant users, which includes distribution of quantum secure key information for secure communication. Teleportation allows an arbitrary unknown quantum state to be conveyed from one distant part to another with perfect fidelity by the establishment of a maximal entangled state of two distant quantum bits. However, the bottleneck for communication between distant users is the scaling of the error probability with the length of the channel connecting the users. The error results from amplitude and phase damping. An exemplary quantum computer example is U.S. Pat. No. 5,793,091 entitled "Parallel Architecture for Quantum Computers using Ion Trap Arrys" which issued to Devoe on Aug. 11, 1998, and is incorporated by reference herein.

Advantageously, optical pulse shaping of the present invention is an attractive route to quantum computing since shaped pulses can be transmitted over optical hardware and the same infrastructure can be used for computation and optical information transfer. The shaped pulses are split into a number of different parts which can carry different train of pulses at different timescales. This provides leverage to control the various nodes where molecular systems interact with shaped pulses to carry out various instructions and perform quantum computing activity at each node during the pulse duration. This further enables the processing of different quantum computational steps at various nodes simultaneously, such that the code is transmitted in parallel for distribution of the task over the network. At the end of the computation the results are read by sending in a "read pulse" and recombining the results. Essentially, this is distributed quantum computing over the network using shaped pulses. Currently, 106 bits can be transmitted/encoded in a single burst of light with the present day optical pulse shaping technology. The repetition rate from the laser source is about 50 to 100 MHz. Thus, one would be able to use terabit/sec bit of communication channel through the existing infrastructure available with the optical community. Once such a quantum computer is available at remote site, these packets acting as "quantum software" can be transferred through high-speed communication channels. Thus, it is possible to carry out quantum computation at a remote distance with the proposed scheme of shaped pulses for terabit/sec communication and molecular control.

Optical Coherence Tomography

Figure 6:
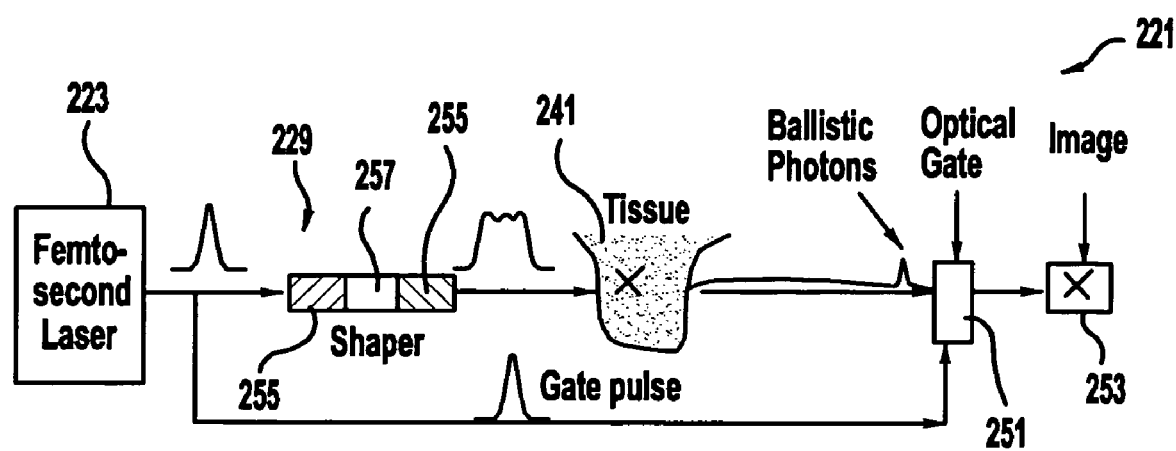
FIG. 6 is a simplified, diagrammatic view showing a fourth preferred embodiment of the present invention applied to optical coherent tomography and photo dynamic therapy.

A preferred embodiment of the present invention uses a laser system 221 for laser excitation or ionization with Optical Coherence Tomography (hereinafter "OCT"). In general, FIG. 6 illustrates the OCT application of system 221 wherein there is a femtosecond laser 223, a laser beam shaper 229, a human or animal tissue specimen 241, an optical gate 251 and an image 253. Laser 223 emits a laser beam pulse shorter than 1 picosecond. Shaper 229 is made of three parts; two dispersive elements 255 which sandwich a phase mask element 257. Shaper 229 essentially prevents multiphoton excitation which can damage the person's or animal's DNA, as will be discussed in more detail as follows. An unshaped laser beam pulse is used to gate the ballistic photons to render the image for tomography use. Optical gating can be accomplished by up-conversion in a frequency doubling crystal or with a kerr-gate in liquid carbon disulphide. The construction of system 221 as illustrated supposes transmission imaging; the same end result can alternately be accomplished with back scattered imaging. Image 253 could be viewed like an x-ray-type image of the internal organs of the human or animal specimen but without harmful three photon exposure. The use of the shaped pulse in OCT provides for an increase in laser intensity for better imaging while preventing the damaging effects caused by multiphoton excitation of healthy tissue. The MIIPS and BPS processes can be advantageously used to activate different dyes and other compounds within a human or animal tissue, to achieve compound specific or functional OCT or microscopy. The pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens. Alternatively, a fluorescent contrast agent can be administered so that pulses shaped using BPS selectively excite the fluorescent agent targeted towards malignant tumors. The embodiment is expected to achieve functional deep tissue imaging.

Figure 7:
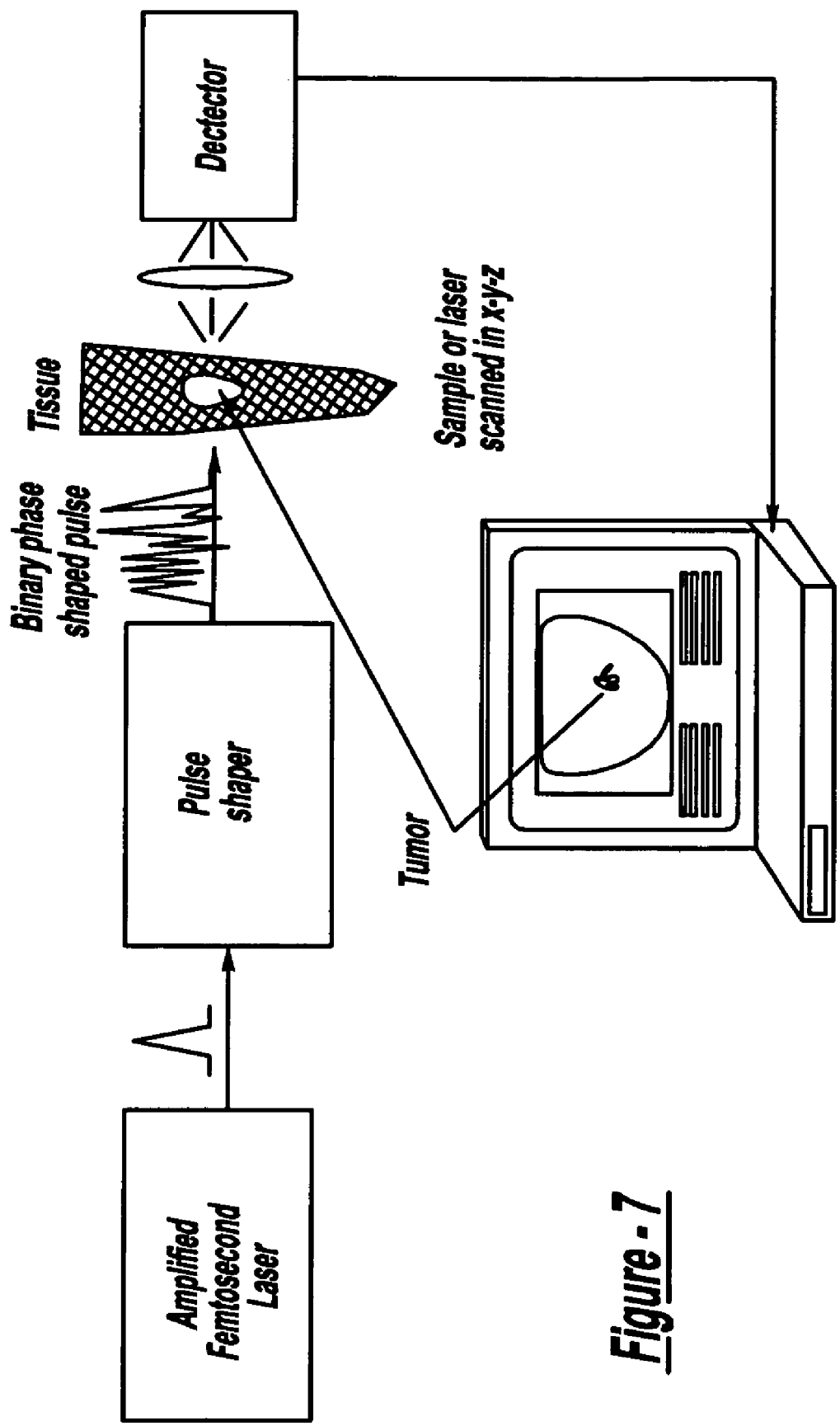
FIG. 7 is a diagrammatic view showing the fourth embodiment system of the present invention using BPS applied to optical coherent tomography and photodynamic therapy.

Referring now to FIG. 7, a system setup for functional imaging using BPS is shown. The tissue has been injected a fluorescent contrast agent that is preferentially absorbed by tumors. The fluorescent is a pH sensitive dye or derivatized quantum dots. No time grating is required.

Photodynamic Therapy

Another embodiment of the present invention uses a system also shown as 221 for laser excitation or ionization with photodynamic therapy (hereinafter "PDT"). PDT is a treatment that involves the combination of visible light and a photosensitizer. Each factor is harmless by itself, but when combined with oxygen, can produce lethal cytotoxic agents that can inactivate tumor cells. This enables greater selectivity towards diseased tissue as only those cells that are simultaneously exposed to the photosensitizer, light and oxygen are exposed to the cytotoxic effect. The dual selectivity of PDT is produced by both a preferential uptake of the photosensitizer by the diseased tissue and the ability to confine activation of the photosensitizer to this diseased tissue by restricting the illumination to that specific region. Therefore, PDT allows for the selective destruction of tumors while leaving normal tissue intact.

PDT is based on the concept that (1) certain photosensitizers can be localized (somewhat preferentially) in neoplastic tissue, and (2) subsequently, these photosensitizers can be activated with the appropriate wavelength (energy) of light to generate active molecular species, such as free radicals and singlet oxygen ($^1O_2$) that are toxic to cells and tissues. PDT is a binary therapy, and a potential advantage of PDT is its inherent dual selectivity. First, selectivity is achieved by an increased concentration of the photosensitizer in target tissue, and second, the irradiation can be limited to a specified volume. Provided that the photosensitizer is nontoxic, only the irradiated areas will be affected, even if the photosensitizer does bind to normal tissues. Selectivity can be further enhanced by binding photosensitizers to molecular delivery systems that have high affinity for target tissue. For photoactivation, the wavelength of light is matched to the electronic absorption spectrum of the photosensitizer so that photons are absorbed by the photosensitizer and the desired photochemistry can occur. Except in special situations, where the lesions being treated are very superficial, the range of activating light is typically between 600 and 900 nm. This is because endogenous molecules, in particular hemoglobin, strongly absorb light below 600 nm and therefore capture most of the incoming photons. The net effect would be the impairment of penetration of the activating light through the tissue. The reason for the 900 nm upper limit is that energetics beyond this wavelength are insufficient to produce $^1O_2$, the activated state of oxygen, perhaps critical for successful PDT.

In general, FIG. 6 also illustrates the PDT application of system 221, but optical gate 251 and image 253 are not required. Shaper 229 allows two-photon excitations but essentially prevents three-photon excitation. Shaper 229 enhances the laser-induced activity of a therapeutic agent which prevents damage of healthy tissue. Use of laser beam pulse shaping of the present invention should provide superior control and results for PDT applications as compared to those practically possible with conventional methods as disclosed, for example, in U.S. Pat. No. 6,042,603 entitled "Method for Improved Selectivity in Photo-Activation of Molecular Agents" which issued to Fisher et al. on Mar. 28, 2000, and is incorporated by reference herein. Alternately, the pulse shaper can be tuned to target cancerous cells for multiphoton gene therapy or destruction, with or without the presence of a therapeutic agent, without damaging healthy tissue. The MIIPS and BPS processes discussed hereinafter can be advantageously used to activate only certain pharmaceuticals or chemicals, or used to allow the laser pulse to enter human or animal tissue to a known depth, based on the phase tuning and associated nonlinear spectrum tuning of the laser beam pulse. The pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens.

General applications of lasers for biomedical purposes are well known for diagnostic tools, surgical tools and for imaging purposes. The immediate extension of ultrashort pulse shaping technology for biomedical applications holds many promises, to further necessitate looking into its domain of influence. Though very few applications for ultrafast pulse shaping technology are currently in use, there are very strong indications as to where it would lead. One of the most commonly adopted methods, for imaging, in recent times for three-dimensional profile measurement is optical coherence tomograph or a white light interferometer, which uses a broadband, low coherence light source. Recently the principle of femtosecond pulse shaping by spectral modulation has been used in conjunction with the joint transform correlator to make a spatio-temporal joint transform correlator.

The advantage of such a technique has been that it essentially removed the need of 1-D depth scanning and thereby avoided the long measurement times involved. Consequently, this eliminates the electronic computation needed to obtain the object image, and so it can be implemented as an all-optical set-up. Initially, this was demonstrated as a surface measurement set-up, however, as a natural extension, it was easily extended for providing tomographic sectioning of biological samples. In fact, with the use of principles of pulse shaping, a depth resolution of 70 µm was achieved. Furthermore since there is no contact between the probe and the tissue, it is a useful non-invasive technique, which provides the physician with near-histological resolution imaging of sub-surface tissue morphology, potentially aiding in biopsy site selection and thus approaching the goal of "optical biopsy".

Nonlinear Optical Excitation Spectroscopy

In one embodiment of the invention, the goal is to develop laser systems capable of generating ultrashort pulses with unprecedented control over the spectral profile and phase properties of the pulses. Specifically, the systems are capable of generating ultrashort pulses that are within 1% of the transform limit, as determined by accurate pulse characterization, by a novel method that incorporates phase characterization and compensation in a single pulse shaping/characterization unit. The same unit will provide calibrated synthesis of arbitrary pulse shapes. One embodiment of the invention, a laser system forms an integral part of a microscope capable of functional imaging, a method whereby pulses are tailored to excite chromophores sensitive to their microscopic chemical environment (pH, $Ca^{++}$, $Na^+$ gradients).

In another embodiment of the invention, a laser system is amplified and shaped by a two-dimensional spatial light modulator. The system is capable of providing single-shot multiphoton excitation spectra over a 20-30 nm range, with 0.05 nm resolution. Two-photon excitation spectra of molecules are usually acquired point by point and are prone to order-of magnitude errors. The system is capable of acquiring 1000 spectra per second over 30 nm excitation regions, and referencing them to a standard. The system improves the accuracy and speed of nonlinear frequency resolved excitation spectroscopy and cross section measurements by orders of magnitude. This information is central to selection and utilization of nonlinear optical materials.

Nonlinear optical excitation spectroscopy (hereinafter "NOES") involves the measurement of nonlinear processes such as two- or three-photon excitation cross-sections and nonlinear optical susceptibilities as a function of wavelength. These measurements are of great importance for the characterization of nonlinear optical materials and nonlinear optical chromophores such as laser dyes and quantum dots. Two-photon excitation spectroscopy, for example, requires a tunable laser source that is both narrow in frequency but highly efficient in multiphoton excitation. Typically, a narrow bandwidth tunable laser is used to obtain data from 700 to 950 nm, acquiring the data point by point. Nonlinear spectroscopy is extremely sensitive to transverse mode quality, spectral phase, characteristics of the focal spot, pulse-1to-pulse intensity variations, and wave front deformations; all of which can cause higher or lower order processes that contaminate the result. All of these factors make point-by-point acquisition prone to systematic errors.

To solve these problems, an embodiment of the invention is based on binary phase masks based on the principles of intrapulse interference (MIIPS) and then optimized using learning calculations afforded by an evolutionary learning calculation. An embodiment of the invention acquires spectra across a large bandwidth in a single laser shot. The high data throughput permits very accurate calibration to some of the best-known standards such as the nonlinear optical crystal KDP and the laser dye Rhodamine 6G. The laser system is not be scanned; in fact, the amplitude of the laser field remains unchanged throughout the experiment. This permits outstanding calibration of all the factors that could affect nonlinear output.

A diffractive two-dimensional programmable phase modulator originally designed by Hamamatsu for optical computing, is ideally suited for this task. The PPM X8267 is a 1024×768 pixel electrically-addressed phase modulator using an image transmitting element to couple and optically-addressed PAL-SLM (parallel aligned nematic liquid crystal spatial light modulator). The number of pixels available for pulse shaping is critical in the design. The generation of well-defined pulses requires the introduction of a well-defined phase functions. Pixilation effects, where a smooth phase is replaced by a jagged, under-sampled phase can be detrimental. The PPM units are illuminated by a spatial image, which is projected into the PAL-SLM. The projection system provides high accuracy reproduction without pixel borders, making it ideal for pulse shaping purposes. The femtosecond laser that is modulated is spectrally dispersed by a 300 lines/mm gold coated diffraction grating and collimated by a gold-coated cylindrical mirror forming a reflective 2 f arrangement. The PAL-SLM is placed at the Fourier plane (where best spectral resolution is achieved). The reflected light is collected by an optical arrangement identical to the input one. Chromatic aberrations and group velocity dispersion are kept to a minimum by the all-reflective optical design. Nonlinear optical distortions and optical damage are minimized by the use of cylindrical rather than spherical optics. The spectrums are dispersed on the horizontal dimension. The pixels in the vertical dimension contain different phase masks that scan the wavelength where nonlinear excitation takes place.

Figure 8:
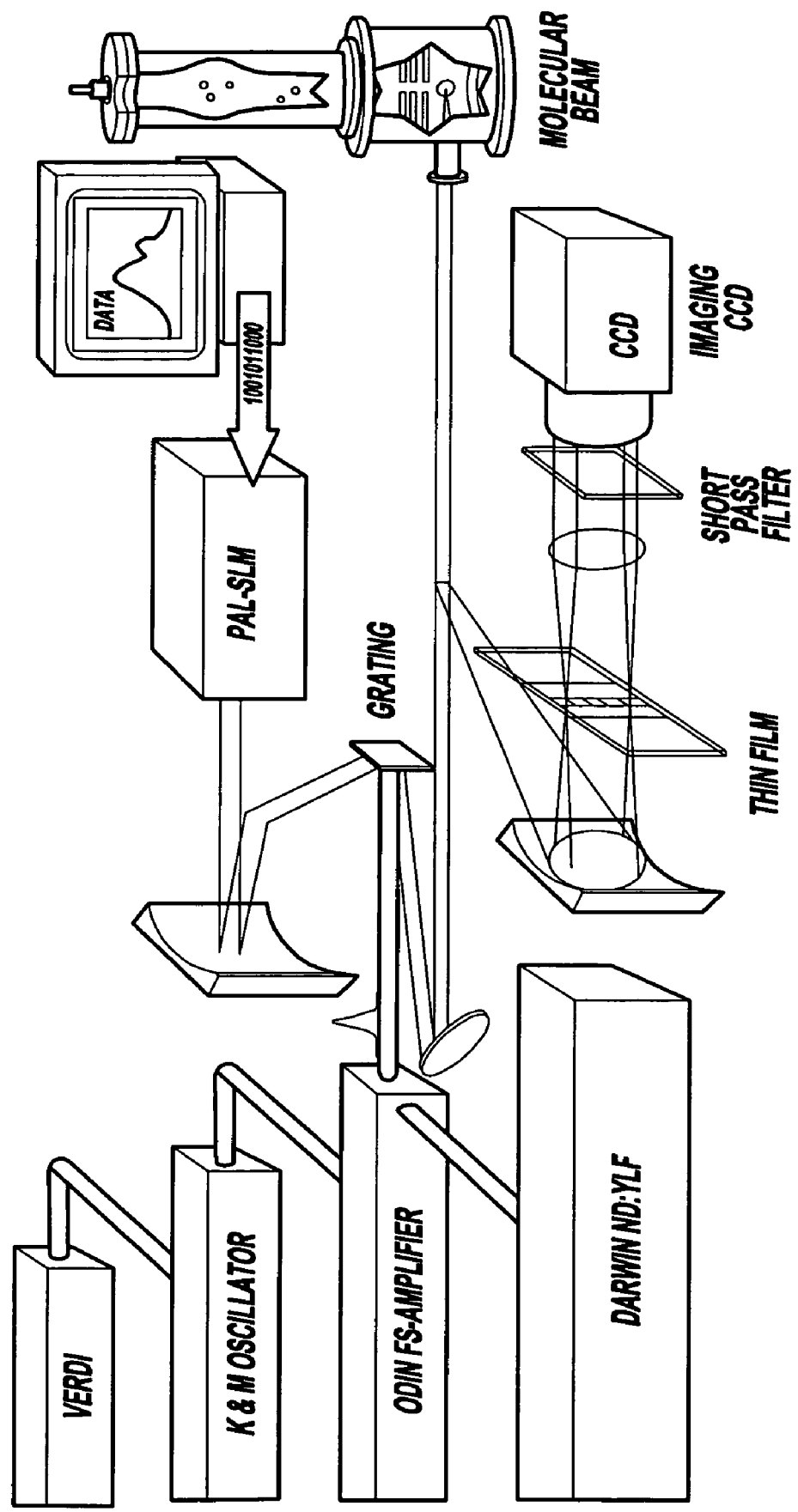
FIG. 8 is a diagrammatic view showing a fifth preferred embodiment of the present invention applied to spectroscopy.

A embodiment of the invention, illustrated in FIG. 8, produces amplified sub-20 fs pulses ($\sim 10^6$ times more energy per pulse than laser System A), but at a repetition rate of 1 kHz. The bandwidth of the pulses is 50 nm FWHM, and is used to obtain NOES with about 0.2 nm resolution. The seed pulses are produced by a K&M Labs oscillator which is pumped by a Verdi laser (Coherent). The amplifier is an Odin, multipass amplifier from Quantronix, pumped by their Quantronix Darwin Q-Switched Nd:YLF, capable of delivering 1 mJ per pulse at 1 kHz. The Quantronix system is quoted for sub-35-fs performance. However, the amplifier is capable of preserving most of the oscillator bandwidth. The amplifier design is based on the multi-pass platform that Kapteyn and Murnane used to demonstrate generation of 17 fs pulses. To achieve the very short pulse duration a grating and prism compressors are used.

The laser system is installed on a 5'×12' vibrationally isolated optical bench (Newport). Pulse characterization is carried out by frequency resolved optical gating (hereinafter "FROG"), SHG-FROG, and MIIPS. For FROG, an optical delay line (Aerotech) is used. Data collection is accomplished using an Ocean Optics spectrometer, a boxcar averager/integrator (SRS), a 500 MHz digital oscilloscope (Infinium, Hewlett Packard), and controlled with a personal computer running LabView, with a GPIB IEEE 488 controller.

Two-dimensional pulse shaping allows single-shot NOES data to be acquired from nonlinear optical materials, two-photon excitation spectra of laser dyes, biologically tagged fluorescent markers, quantum dots, optical switches and other optical materials. The wavelength range is limited to the 700 to 900 nm window by the pump pulses. The laser system is used to pump a non-collinear optical parametric amplifier, producing tunable broad bandwidth pulses from 450 to 1300 nm. These pulses are directed to the two-dimensional pulse shaper when characterization of a material is required at very different wavelengths.

The MIIPS method, described previously, requires the scanning of a reference phase across the spectrum of the laser. This usually requires acquisition of the SHG output spectrum for ~100 different phase function positions. To achieve this task in a single shot, the vertical dimension is divided into 128 different sections. Each section, containing 6×1024 pixels, contains the reference phase function. The key is that the phase function is displaced in each of the sections to provide the data as a function of δ required for MIIPS. Once the femtosecond laser pulse undergoes the two-dimensional phase modulation it is focused with a short focal length ~100 mm cylindrical mirror on a thick SHG crystal. On the horizontal axis, the thick SHG crystal causes a spectral dispersion that is analogous to the one used in the GRENOUILLE. On the vertical axis, one obtains different sets of sets of SHG spectra because of the different phase functions encoded by the PAL-SLM. The entire two-dimensional image, containing the one-shot MIIPS data is then imaged onto a CCD for collection and analysis.

Communications

Figure 9:
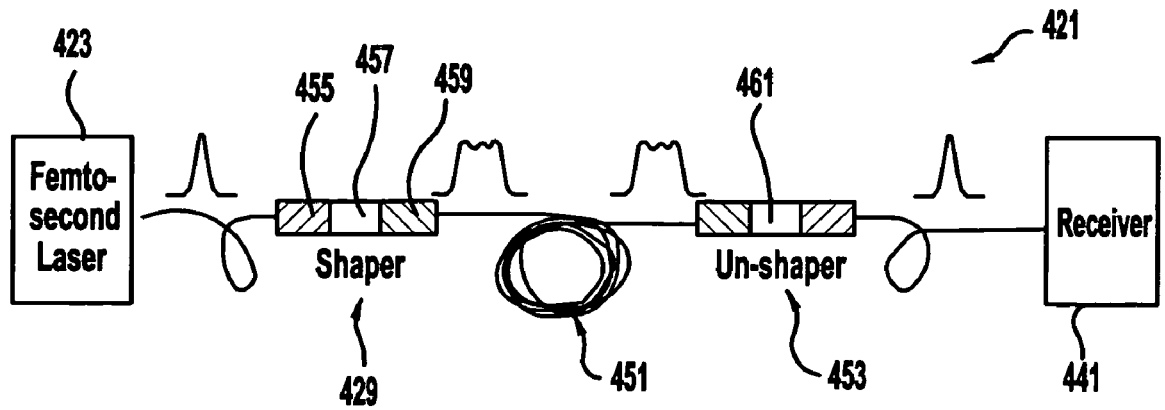
FIG. 9 is a simplified, diagrammatic view showing a sixth preferred embodiment of the present invention applied to communications.

With reference to FIG. 9, another preferred embodiment of a laser excitation system 421 of the present invention employs a femtosecond laser 423, an optical fiber 451, a laser beam pulse shaper device 429, a laser beam pulse un-shaper device 453, and a receiver 441 which includes an optical switch or sensor and the related circuitry and electrical control unit. Laser 423 emits a series of laser beam pulses, each shorter than 1 ps, into the connected fiber 451. Pulse shaper device 429 is of a predetermined mask type with a fixed pulse characteristic varying shape (such as with calculated sine wave surface shapes) and has three elements connected to fiber 451: a dispersive element 455 such as a fiber that incorporates a diffraction grating; a phase mask element 457 that can be made using a doped glass or polymer sheet; and a dispersive element 459, like element 455 but reversed, for accepting spectrally dispersed light and coupling it back to fiber 451.

The shaped laser beam pulse is capable of traveling long distances through fiber 451 without suffering nonlinear distortion because of the unique phase function imprinted or formed on shaper device 429. For example, the red color spectrum may be advanced in front of the blue color spectrum in a precise sine manner. Un-shaper device 453 subsequently reverses the phase changes introduced by shaper device 429. It is constructed the same as the shaper device but with a different phase mask element 461 that compensates for the pulse characteristic changes made by mask element 457. Alternately, an acousto-optic modulator or transient grating can be used for optical switching through constructive or destructive reference of waves. Shaping and unshaping can also be accomplished by means of a chirped mirror or spectral masks.

Thus, the present invention's ability to precisely control the laser beam pulse shape or other characteristic, especially for nonlinear or multiphoton emissions, significantly improves the quality of the communication transmission while minimizing self-focusing, self phase modulation and possible destruction of the fiber. The pulse characteristic control of ultrafast laser beam pulses, as described in all of the embodiments herein, should minimize, if not prevent, multiplicative noise effect disruption of nonlinear propagation channels in fiber optic lines, as discussed in Mitra, et al., "Nonlinear Limits to the Information Capacity of Optical Fibre Communications," Nature, vol. 411, pp. 1027-1030 (Jun. 28, 2001). It is further envisioned that this type of pulse shaping system can be employed within salt water oceans for submarine-to-submarine communications using short laser pulses of 1 ps or less. This type of pulse shaping can be used to induce solution formation to achieve minimally distorting pulses for communications. Moreover, MIIPS can be used to measure the distance of a fs laser emitter by determining the magnitude of the acquired second order phase modulation as the laser pulse transmits through air or water. This method does not require echo or reflection. In water longer pulses (1 ps) are desired because of the much greater dispersion. Depending on the transmission medium, air or water, and the distances expected different pulses are required. For air, short pulses with durations between 10-20 fs will be preferred. For water, pulses with much longer durations will be preferred, for example for 100 m distance 100 ps pulses would be preferred.

Using the BPS method, the data density that can be achieved per pulse is equal to or less than the number of pixels in the SLM divided by 2. For example, in an embodiment in the SLM 429 has 256 pixel resolution, the maximum data density is 256/2 or 128 bits per pulse. In this embodiment, if the pulse rate is 100 MHz, the data rate or bandwidth would be $10^{10}$ bits per second. Other embodiments of the invention vary the data rate or bandwidth based on pixel resolution and/or laser pulse rate. As laser pulse rates increase and as SLM pixel resolution increases, the bandwidth achieveable by this invention will increase. It is advantageous that only a nonlinear optical detector would be able to decode the signal and, in contrast, a simple light detector would not be able to determine any information from the pulses. The fact that it can be used asynchronously is ideal for mobile or distant, and intermittent communications.

Figure 11A:
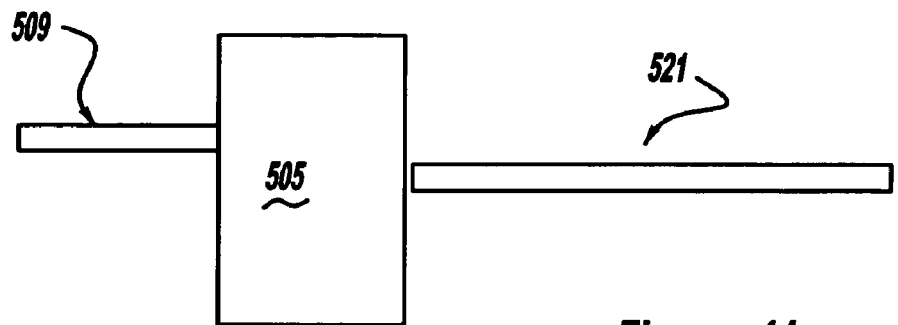
FIGS. 11a and 11b are diagrammatic views showing components in an alternative embodiment of the present invention applied to communications.
Figure 11B:
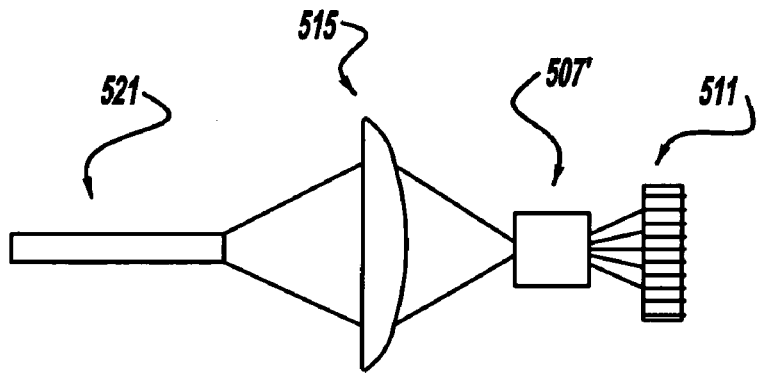
Figure 10:
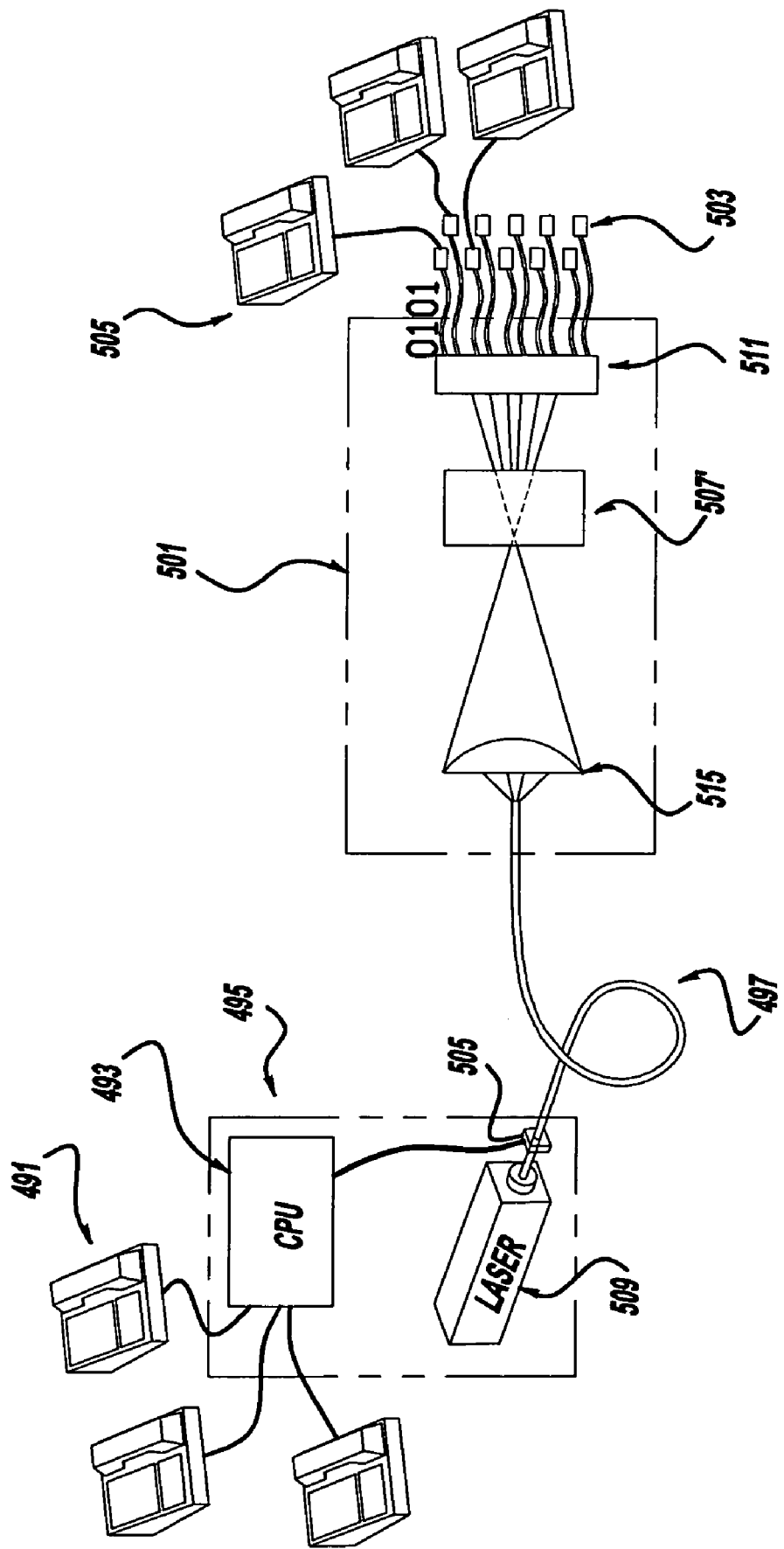
FIG. 10 is a diagrammatic view showing the sixth preferred embodiment of the present invention applied to communications.

Referring to FIGS. 10, 11a and 11b, another preferred embodiment of the system of the present invention is used for fiber optic communications. Multiple transmission users who are each sending a communications message or signal are using a communications device such as a telephone 491, personal computer, facsimile machine or the like, at remote locations from each other. These remote transmitters are connected to a "smart" main transmitter assembly which includes a computerized, central processing unit 493 through electric wires, fiber optic cables, microwave signals or the like. A phase modulated pulse shaper 505 is actively controlled by CPU 493. Laser 509 and shaper 505 are also contained as part of the main transmitter assembly. Laser 509 emits an ultrashort laser pulse which is carried within a fiber optic cable 497 after shaping. The ultrashort laser beam pulses have a duration of about 100 femtoseconds based on currently available fiber optic cable limitations but pulse durations of less than 50 femtoseconds would be preferred and those of 10 or less femtoseconds would be the most desired if fiber optics allow for such in the future. For example, photonic band gap materials such as optical fibers with holes therein may allow for use of approximately 10 femtosecond pulses.

Pulse shaper/phase mask 505 encodes each laser beam pulse phase, using a binary phase mask. The second harmonics contains multiple peaks, by way of example, but not limitation, in the frequency domain, thus revealing the encoded message. This allows encoding of routing addresses and the associated communications information to be encoded within each laser beam pulse based on CPU control of the laser beam emissions in combination with actively varied shaping of each emitted pulse.

A "dumb" central receiver 501, one that does not require an additional laser or complex computational capabilities, is connected to the downstream end of fiber optic cable 497. Receiver 501 includes a focusing lens 515, a thick SHG crystal 507' and a detector 511. Each laser beam pulse transmitted through fiber optic cable 497 is dispersed onto lens 515 which serves to focus and direct each pulse, in a converging angular manner, onto crystal 507'. A thick optical crystal 507' is defined herein as one having a transmissive path thickness of greater than about 0.5 millimeters while a thin optical crystal 507 is defined herein as having a transmissive path thickness less than about 0.5 millimeters. The preferred thickness for the thick crystal is approximately 3.0 millimeters for 50 femtosecond or less pulse duration and 5.0 millimeters for a 50 to 200 femtosecond pulse duration. Thick crystal 507' creates a second order harmonic and second order spectrum within each pulse as previously shaped by the pulse shaper. In other words, the thick crystal disperses essentially the entire color spectrum without use of a separate spectrometer because of the phase matching angle requirement.

Each separated color frequency angularly dispersed from the thick crystal is encoded by the pulse shaper to contain individual communication routing addresses and the actual communications information, which is then detected by a multiplexer-type of detector 511 such as a CCD camera employing a linear array. Alternately, detector 511 is a two-dimensional array that can be used to achieve higher data densities by adding one more dimension. It is also alternately envisioned that detector 511 is an array of optical fibers that are connected to remote controllers/sub-detectors. The data can be read asynchronously using only the transmission pulse containing the information and not additional reference pulse. A single detector 511 is operable to digitize the detected signals carried in each pulse as separated through the spectrum and transmit them through wires, fiberoptics, microwaves or the like to individual decoding microprocessor controllers 503 within or external to receiver 501. A set of prestored variables or dencryption information or key is located within memory of each controller 503 in order to decode each corresponding digitized communication signal received by detector 511 without requiring synchronous communication transmissions (in other words, a second laser pulse that provides a complimentary phase) from transmitter 495. The decoded communications are then sent to the end users who receive such by telephones 505, personal computers, facsimile machines or the like at the identified routing addresses desired. Alternately, controllers 503 can be replaced by simple light detection devices such as photo-diodes which can be employed in a digitized on/off self-switching mode based on the signal detected by detector 511 to control or send information to remote destinations. It is significant that interferometry and synchronous laser pulses are not required for decoding the transmitted information with the presently preferred communications embodiment of the present invention. It is also noteworthy that pulse shaper 505 can encode each pulse by use of second harmonic generation or any other non-linear mixing method including, but not being limited to, frequency mixing, difference frequency mixing, and four wave mixing.

MIIPS Improvements

Another preferred embodiment of the present invention control system and apparatus enhances the ultra-fast laser output by placement of a MIIPS box or unit upstream of an amplifier's output. As used herein, it should be appreciated that the phrases "MIIPS box" and "MIIPS unit" can be used to include, but are not limited to, separately housed MIIPS components or some of the components thereof used to perform MIIPS being integrated into an amplifier housing, or other laser device, either physically between or in the optical path between the oscillator and final amplifier of the laser, or offset therefrom but with similar functioning. In one variation of this embodiment, a separate MIIPS box is placed directly between an ultra-short, femtosecond oscillator and an ultra-short amplifier. This is illustrated in FIG. 13b. The present invention accurately measures output phase distortions using the MIIPS method which then employs the programmable, computer software to correct the distortions at the pulse shaper in the MIIPS box or by directly moving optics such as an amplifier's compressor and/or stretcher gratings. The computer controller and its software can also be used to determine specific output conditions such as laser pulse duration, central wavelengths, spectral shape (for example, Gaussian, Lorenzian or Sech-sq), or the like. The pulse has specific phase characteristics such as transform limited or with a specific user-specified phase. Furthermore, the output is optimized and detected at the downstream, output side of the amplifier or, alternately, at a more distant downstream location such as at the specimen using a wireless, SHG crystal with a compact spectrometer.

Figure 13A:
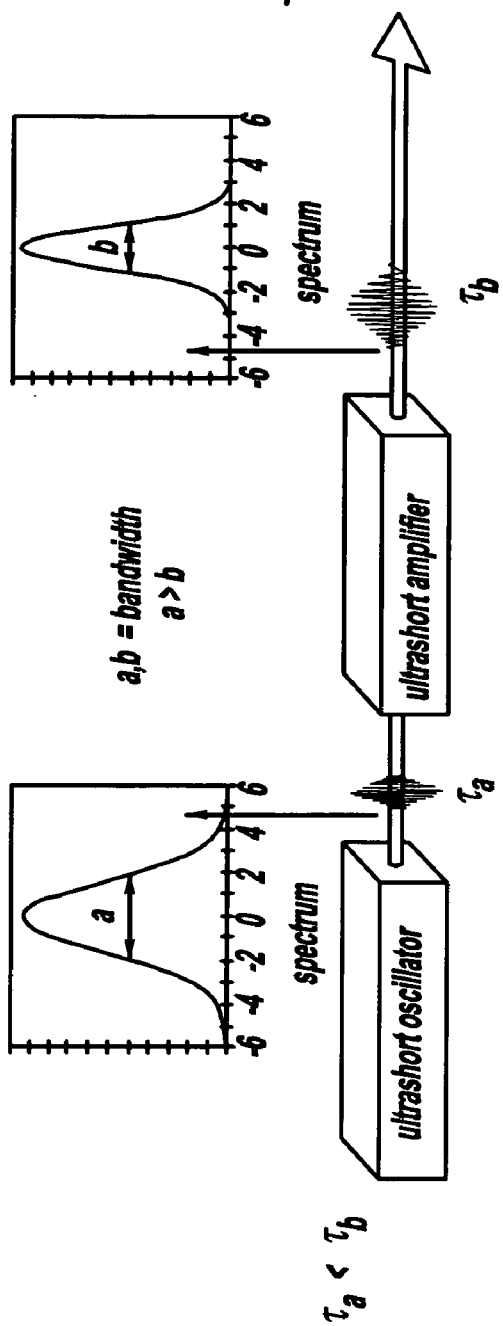
FIGS. 13a and 14a are diagrammatic views showing regular, non-MIIPS operation of an ultra-short laser.
Figure 13B:
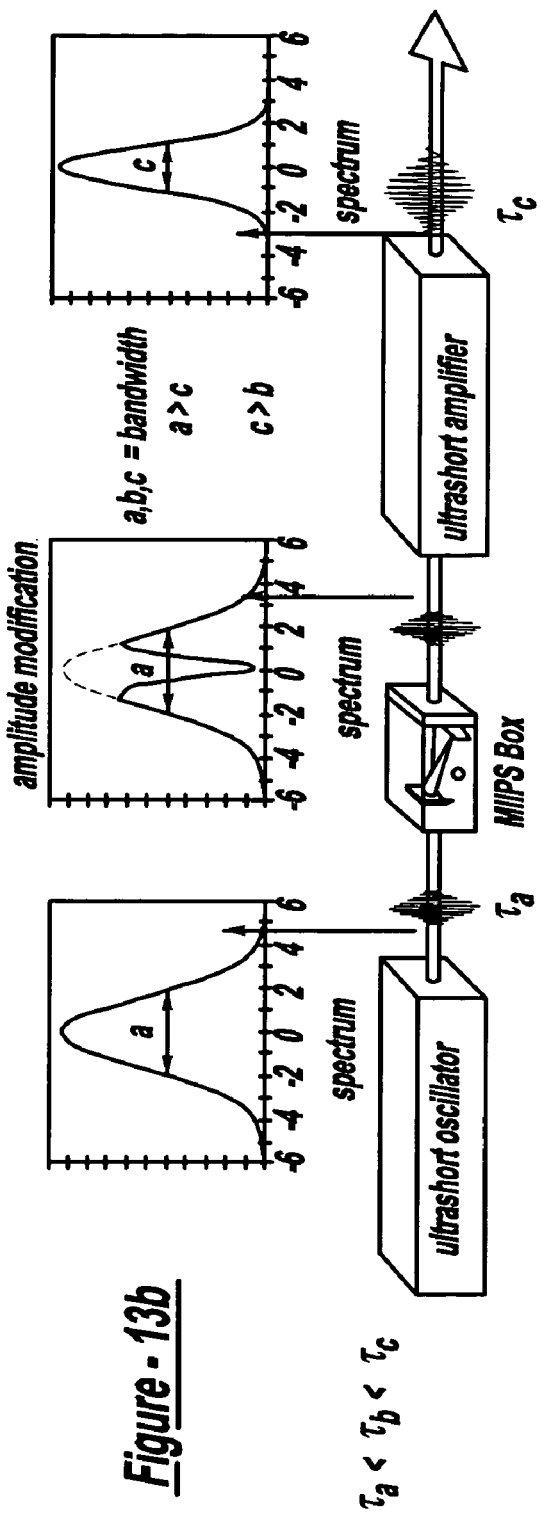
FIGS. 13b and 14b are diagrammatic views showing improved operation of an ultra-short amplifier using upstream MIIPS employed in a seventh preferred embodiment of the present invention.
Figure 14A:
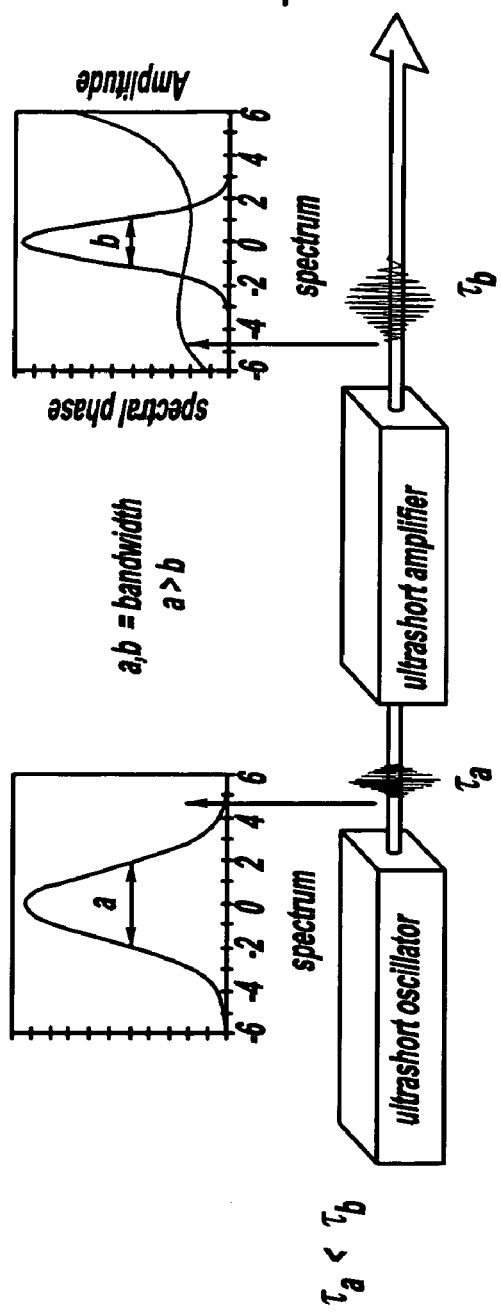

FIGS. 13a and 14a represent conventional use without MIIPS. This should be contrasted to the representation of FIGS. 13b and 14b wherein MIIPS is used upstream of the laser output. The term "ultra short or femtosecond laser" as used herein includes an oscillator and one or more amplifiers. Furthermore, the term "upstream" as applied to the laser herein includes any position along a laser beam pulse's path before the output of the final amplifier, and the term "downstream" as used herein with regard to the laser is any position along the laser beam pulse's path after emission output from the final amplifier (see FIG. 21). Use of MIIPS on the upstream laser side provides significant pulse-duration shortening and efficiency improvements, but with minimal intensity loss penalty, especially as compared to conventional approaches of shortening pulse duration without the present invention. Upstream use of MIIPS also achieves significantly shorter pulse durations as compared to downstream use of MIIPS (see FIGS. 1, 2 and 4-11 for downstream examples), substantially without other componentry changes. The advantage of MIIPS use in this manner is that it compensates for losses in the amplifier and it provides a better sense of the amplifier parameters that needs to be adjusted. It is also noteworthy that in order to obtain the best performance (in other words, shortest pulse) out of an amplifier, one needs to reduce the effect of spectral narrowing typically caused in regeneratively amplified systems. This method of the present invention easily compensates for spectral amplitude narrowing by measuring the output and correcting by amplitude modulation control using a dual mask shaper without the need for typical input or output polarizers as the amplifier only takes in one polarization. The present invention system directly interfaces with structure and compressor optic gratings or prisms since it can reliably measure the pulse phase in an accurate manner. Moreover, the present invention can accurately be used with pulses that are 50 fs and even as short as 3 fs, while also adjusting amplitude modulation to correct spectral dispersion. The MIIPS and device and method, especially on the upstream side of the laser, does not require synchronization while achieving greater transmission efficiency.

More specifically, FIG. 13b shows an amplitude shaping ultra-short laser pulse, ultra-short being between about 1 fs to sub-10 ps, from an ultra-short laser oscillator using a spatial light modulator (SLM) in order to minimize gain narrowing in an ultra-short laser amplifier. The ultra-short laser oscillator as referred to in the preceding sentence is also known as a "seed" laser and the amplifier as used herein can be any of an optical parametric amplifier, a regenerative amplifier, a multi-pass amplifier or the like, preferably a Legend brand amplifier which can be obtained from Coherent Inc. An ultra-short laser oscillator normally has a large bandwidth that is partially lost in the ultra-short laser amplifier due to the inevitable gain narrowing therein. In the figure, $\tau_a$ is the pulse duration at position a of the initial spectrum and $\tau_b$ is the pulse duration at position b of the downstream and amplified spectrum. It is noteworthy, however, that the laser performance is significantly improved by placing the MIIPS box in the beam path between the oscillator and the amplifier.

The upstream MIIPS placement allows for the introduction of an inverse Gaussian amplitude profile or other optimized profile on the seed spectrum by a dual or single mask spatial light modulator which increase amplification efficiency of the spectrum "wings" in the seeded spectrum. Therefore, larger bandwidths are emitted from the amplifier. This method is ideally conducted in an iterative manner automatically by comparing outputs and making further corrections. The central spectrum graph in FIG. 13b, entitled "amplitude modification" shows a central "hole" which is introduced using the phase/amplitude modulator. The voltages in the pixels are set so that only phase delay or amplitude modulation is obtained. The computer controller automatically varies the voltage so that the transmission changes at different frequencies. The profile and location in the spectrum are important and the profile should be dictated by the output of the amplifier, preferably optimized in an iterative manner with a series of sequential femtosecond pulses. The MIIPS exemplary box is physically split into two component sub-assemblies: one includes the shaper, which can be a grating prism, curved mirror and/or SLM; the other is the detector that generates the second harmonic, records its spectrum and then sends the corresponding signals to the computer controller. The MIIPS detector can be in the box, a remote unit placed at the output of the laser, or it can be placed remotely at the specimen which may be a few feet or even miles away from the laser. The second-subassembly of the MIIPS box includes a thin SHG crystal or powder of an SHG crystal to create the second harmonic. The preferred compact spectrometer can be obtained from Ocean Optics as Model No. USB200. In another variation, MIIPS is used to compare theory and experimental results to fine tune the pulse shaper, especially for binary pulses; this allows the MIIPS unit to retrieve and/or imprint complex spectral phases onto ultra-short laser pulses where complex spectral phases can have discontinuities or are of a binary nature, preferably in an iterative manner. The upstream positioning of the MIIPS box with the present embodiment significantly improves operation of the one or more ultra-short amplifiers employed while minimizing gain narrowing, thereby resulting in shorter pulse duration and wider pulse bandwidth, at a significantly reduced cost.

Figure 14B:
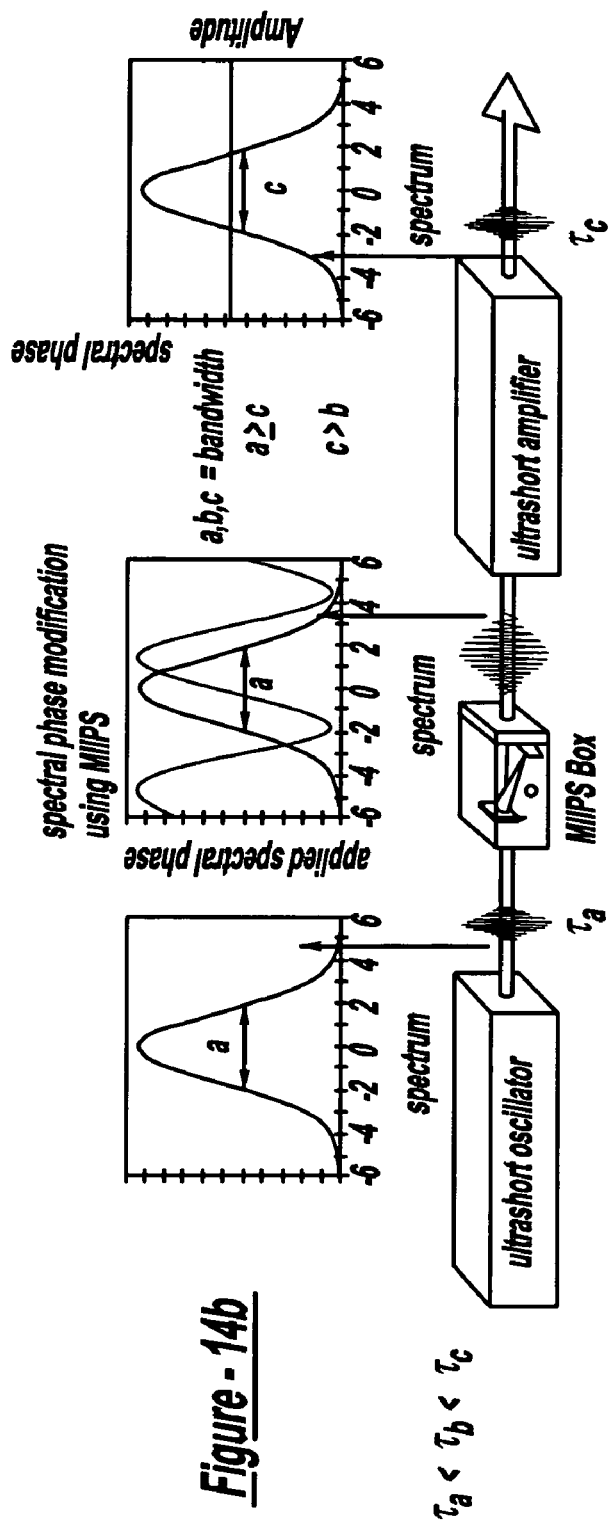

FIGS. 14a and b further compare downstream MIIPS use (see FIG. 14a) with the improved upstream MIIPS use (see FIG. 14b) in a further variation of the presently preferred embodiment of the present invention. A spatial light modulator and MIIPS unit are located between an ultra-short laser oscillator and ultra-short laser amplifier for measuring, pre-compensating and correcting the spectral phase distortions and for delivery of amplified arbitrarily shaped pulses in order to obtain transform limited pulses while gaining the maximum bandwidth of these pulses. The output of the amplifier is measured and its MIIPS trace is recorded and corrected by the software in the computer controller, in an iterative manner while introducing specific spectral phase functions on the SLM. FIG. 14a compares the upstream and downstream spectral phases of the laser beam pulse during regular, non-MIIPS operation of all ultra-short amplifiers, demonstrating resulting inevitable spectral phase distortion. FIG. 14b, in contrast, graphically demonstrates the shorter pulses in flat spectral phases and wider bandwidth of the laser beam pulse employing MIIPS located upstream in the laser.

Figure 20:
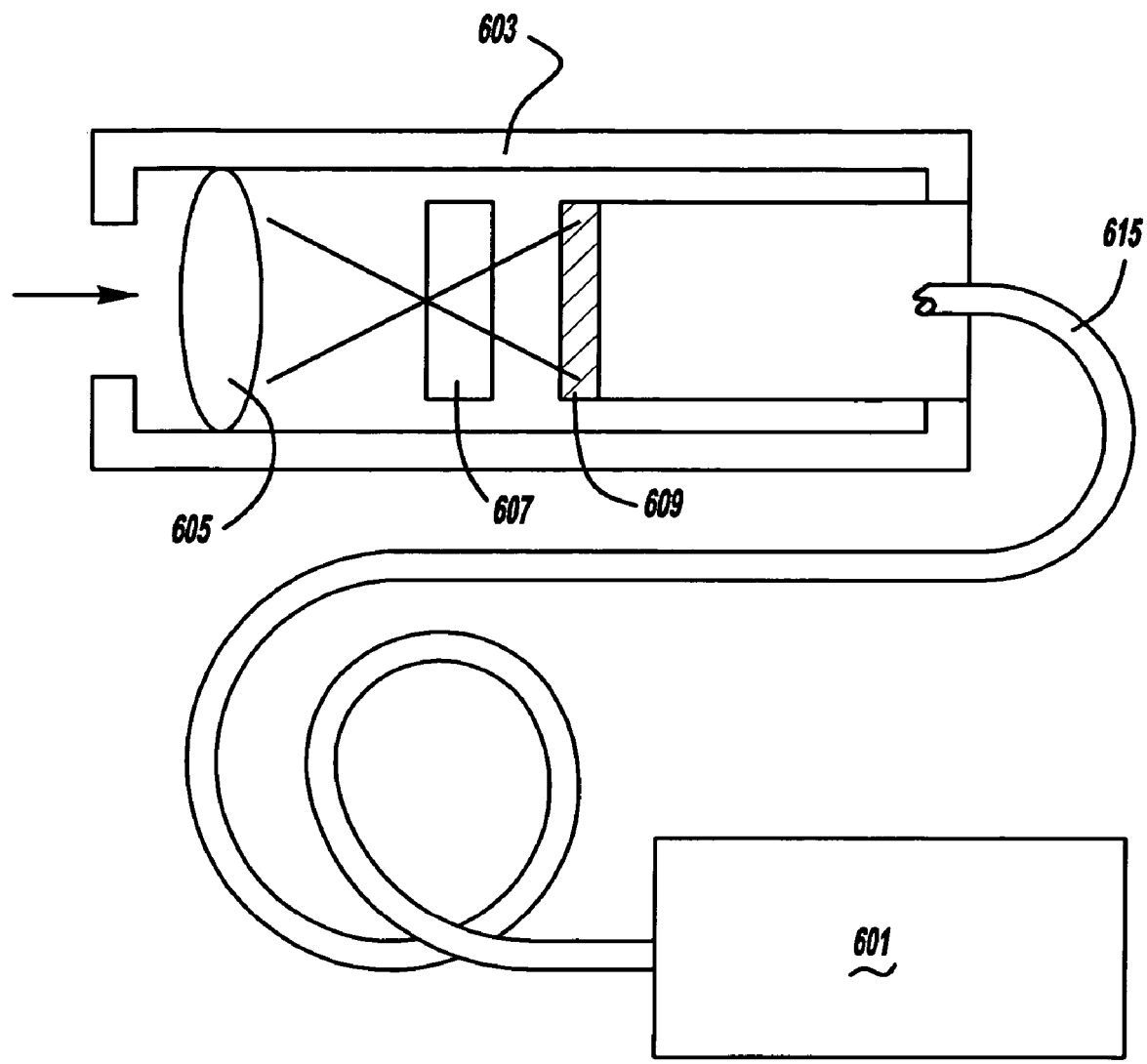
FIG. 20 is a diagrammatic cross-sectional view showing a ninth preferred embodiment of the present invention employing an optic head used with a remote spectrometer.

A further preferred embodiment of the present invention is illustrated in FIG. 20. A preferred Ocean Optics, compact spectrometer 601 is remotely located and attached to an optic head 603 coupled by a fiber optic cable 615. The compact spectrometer is connected to the MIIPS controller electrically. Head 603 includes a focusing lens or mirror 605, SHG crystal 607, and a spectral filter 609. The remote spectrometer, which saves space within the MIIPS box, employs head 605 which can be placed anywhere along the laser beam path to provide an evaluation signal to the MIIPS unit as required for the specific usage application. Alternately, the compact spectrometer can be detachable from the MIIPS box and placed at a differing, downstream location where it samples the puls. A wireless communication interface can be employed between the spectrometer and computer to avoid long cables.

Figure 21:
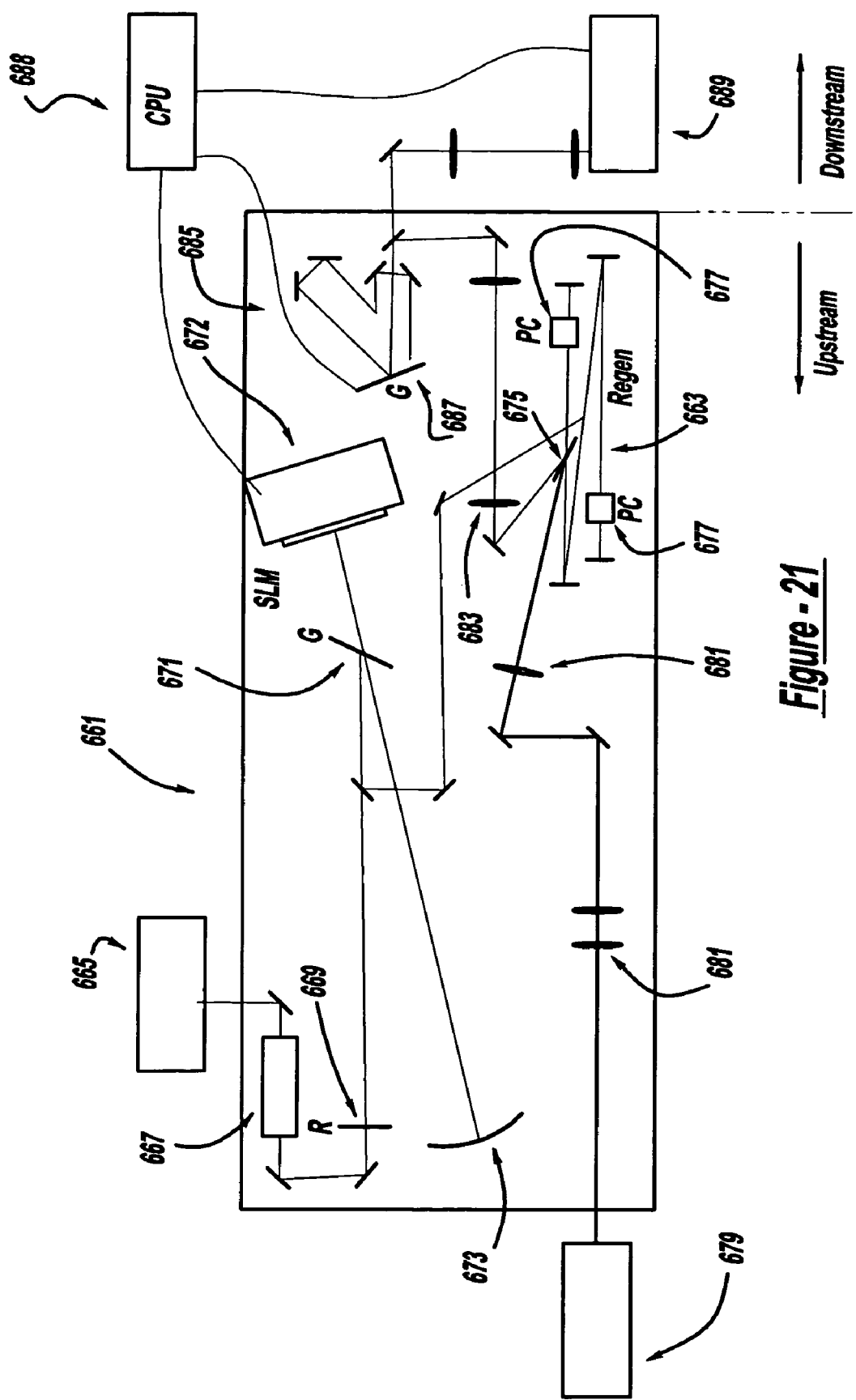
FIG. 21 is a diagrammatic view showing an amplifier employed in a tenth preferred embodiment of the present invention.
Figure 22:
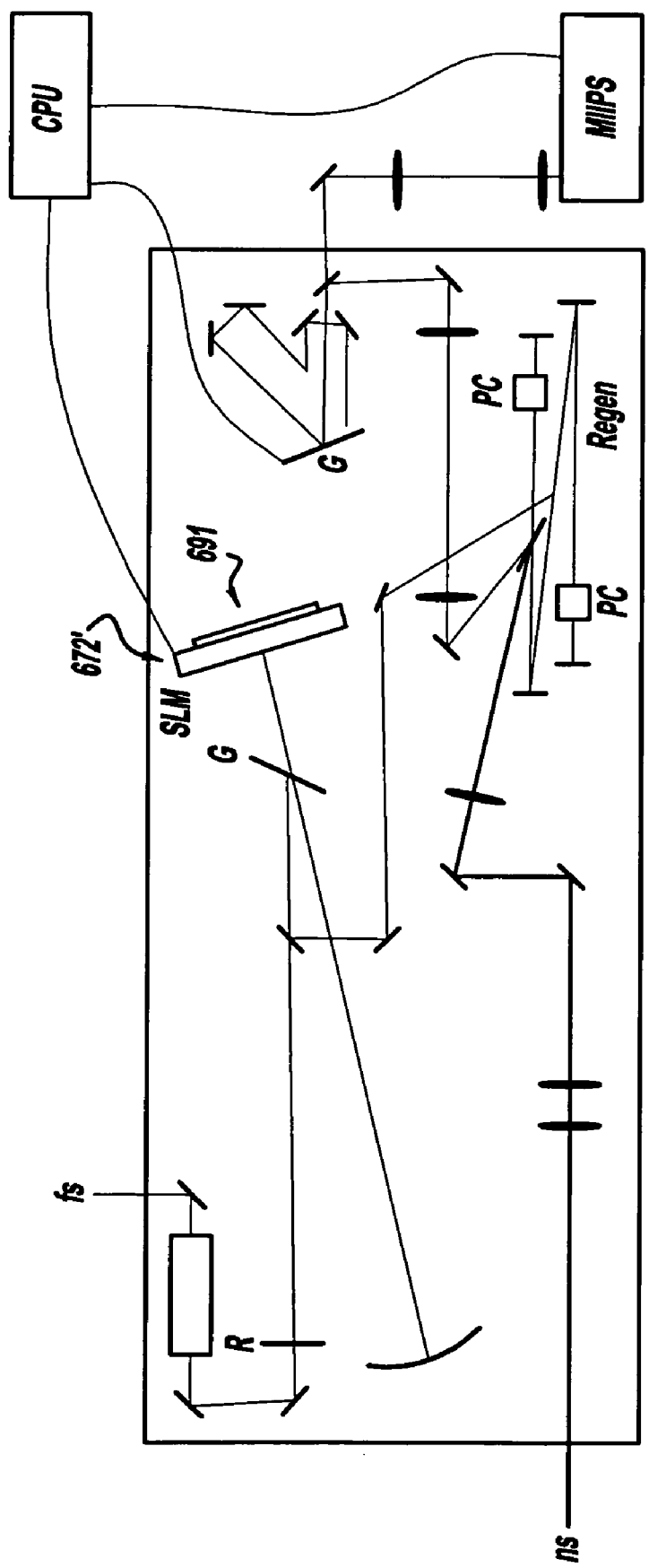
FIG. 22 is a diagrammatic view showing an amplifier employed in an eleventh preferred embodiment of the present invention.
Figure 23:
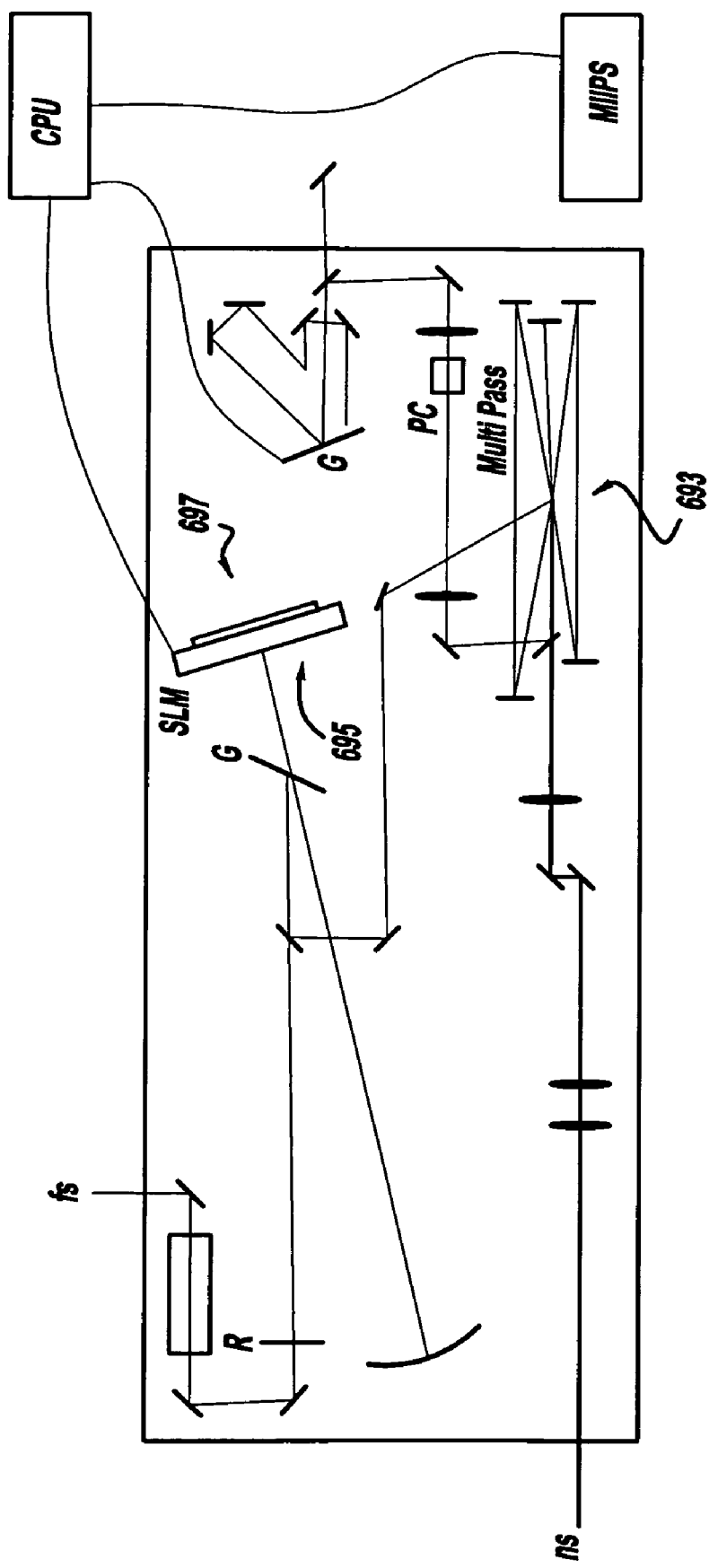
FIG. 23 is a diagrammatic view showing an amplifier employed in a twelfth preferred embodiment of the present invention.

FIGS. 21 through 23 disclose preferred variations of the laser employing the MIIPS unit on the upstream laser beam path between the oscillator and the amplifier. FIG. 21 illustrates a chirped pulse amplifier 661 with regenerative amplification 663. An femtosecond input pulse is emitted by an oscillator 665 which is then directed to a faraday isolator 667, reflected by high reflection mirrors and transmitted through a retro-reflecting mirror pair 669. The pulse is then sequentially transmitted to a grating 671, SLM 672 and curved mirror 673. The pulse is also reflected by mirrors to a regenerative amplification section 663 including a Ti-doped Sapphire crystal 675, mirrors and pockel cells 677. A ns input pulse is sent from a pump laser 679 through lenses 681 and mirrors to regenerative amplification section 663. The amplified fs pulse is subsequently transmitted through lenses 683 and mirrors to a compressor section 685, including a grating 687 and mirrors. The downstream pulse output is then detected by the SHG crystal and spectrometer unit 689. In this variation, the main reflector of a conventional stretcher has been replaced by a reflective SLM. The reflective SLM can be a deformable mirror. Alternative, other reflective SLM designs exist such as the parallel aligned nematic liquid crystal (PAL) SLM from Sony (LCX012BL). The SLM is under control of a CPU controller 688 which performs a MIIPS scan using a remote detector 689 that samples the amplifier output and obtains the spectrum of the second harmonic of the input beam. The SLM is capable of introducing a spatially varying phase delay and also of introducing a spatially varying change in amplitude. The controller also automatically adjusts the angle of a grating and/or the spacing in the stretcher to compensate for quadratic and cubic phase distortions.

FIG. 22 illustrates a variation employing a chirped phase amplifier with regenerative amplification. Unlike the immediately prior variation, the present one locates an SLM 672' a transmissive LCD for example, in front of the main reflector 691 of the stretcher. The CPU controller automatically controls the SLM for performing a MIIPS scan using a remote detector that samples the amplifier output and obtains the spectrum of the second harmonic of the input beam. The SLM is capable of introducing a spatially varying phase delay and of introducing a spatially varying change in amplitude. The CPU automatically adjusts the angle of the grating and/or changing the spacing in the stretcher to compensate for quadratic and cubic phase distortions.

The next variation shown in FIG. 23 uses a chirped pulse amplifier with multi-pass amplification 693. In this variation, an SLM 695 is located in front of a main reflector 697 of the stretcher and otherwise acts like to that of the immediately preceding variation. It should also be appreciated that a reflective SLM can alternately replace a reflector at a compressor for shaping and MIIPS, instead of being at the stretcher. This would allow for improved phase and amplitude control but at a small reduction in output energy.

Figure 15:
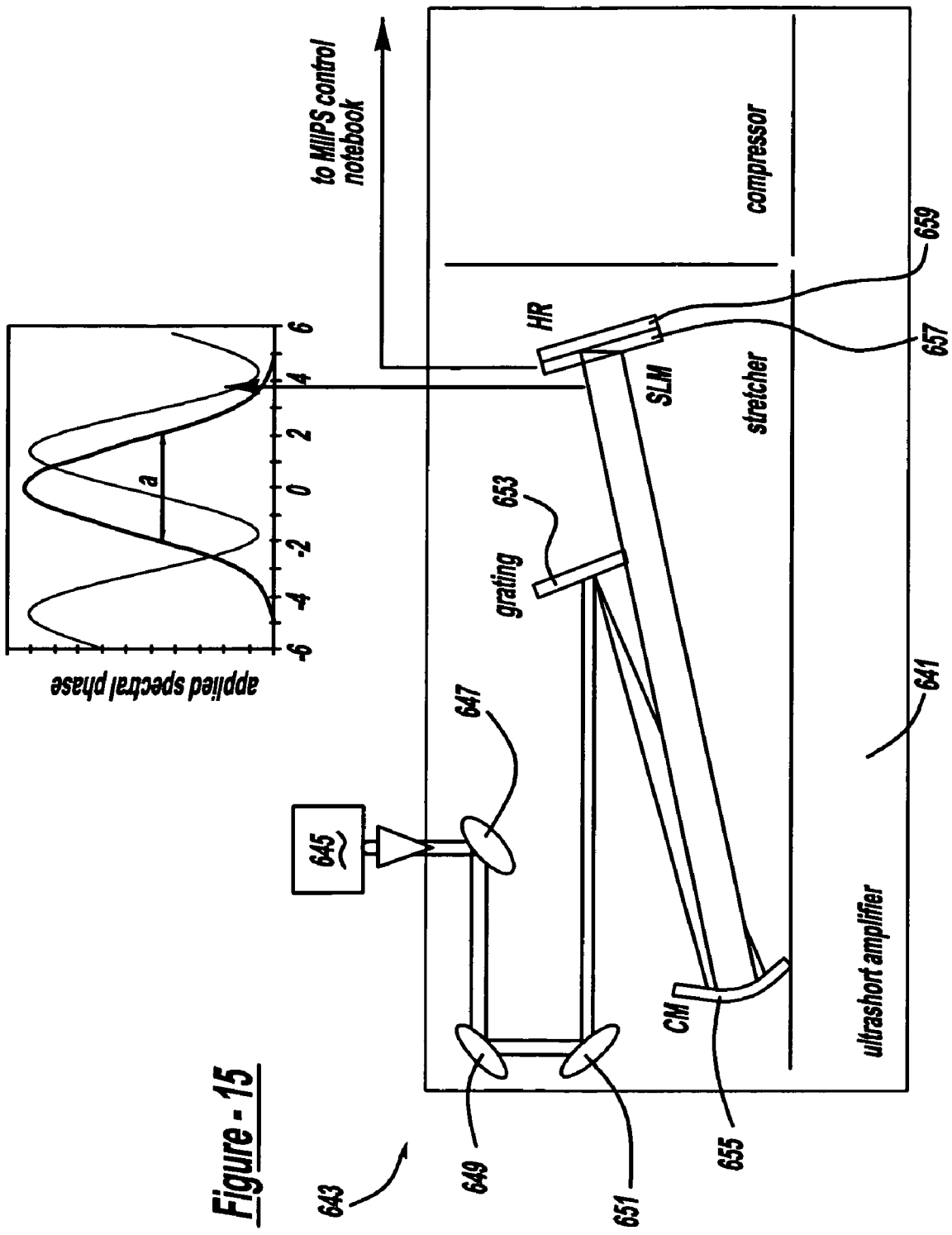
FIG. 15 is a diagrammatic view showing an eighth preferred embodiment of the present invention used in an ultra-short amplifier.

FIG. 15 shows another variation of the presently preferred embodiment wherein a stretcher is separated from a compressor within an ultra-short amplifier 641 of laser 643. A femtosecond oscillator 645 of laser 643 emits an ultra-short laser beam pulse which is reflected off of mirrors 647, 649 and 651, separated by grating 653 and collimated by curved mirror 655. The pulse is then directed to SLM pulse shaper 657, backed by a highly reflective mirror 659. The mirrors, grating, curved mirror, SLM and highly reflective mirror are all located within the stretcher section of the amplifier. The MIIPS measurements and determinations cause an adjustment in the optics of the stretcher and/or compressor of the amplifier to achieve a desired level of chirp. The MIIPS software in the controller controls translation movement of the grating pair, for example, in the ultra-short amplifier's compression section thereby decreasing or increasing linear chirp to compensate for phase distortions in the pulses; this corrects for, by way of example, large linear chirp group velocity dispersion (GVD). Similar MIIPS characterization (such as measurements) and compensation allow for automated controlling of the tilt angle and incidence angle of a large highly reflective mirror (see 659 in FIG. 15). In the structure of the ultra-short laser amplifier which influences quadratic chirp ($fs^3$) in conjunction with the MIIPS unit measurements. This minimizes the SLM requirements thereby effectively reducing the load burden of large correction parameters and allowing for more fine tuning with the MIIPS unit. The compressor gratings and mirrors can therefore be adjusted to compensate for quadratic dispersion and sometimes cubic dispersion. The controller automatically calculates the quadratic and cubic dispersion and then uses the grating and mirror mechanical adjustment in the compressor to make a rough and coarse initial correction; thereafter the SLM pulse shaper makes the fine tuned corrections in especially the high order phases.

The upstream placement of the MIIPS unit is ideally suited for use with a tunable laser, such as the Chameleon-XR brand laser which can be obtained from Coherent, Inc. An electronically integrated system interface includes a MIIPS unit with motorized and micrometer actuators that translate gratings and/or mirrors to compensate for changes in the output wavelength of the laser. The actuators are automatically driven by energization signals from the computer controller, in a real-time, closed loop manner based on comparisons of the detected signals from the spectrometer and desired value calculations. The MIIPS detection can take place at the specimen. When the specimen is observed through a microscope objective, MIIPS can compensate for the GVD introduced by specific objectives at the specific wavelength of emission of the tunable laser source.

Another preferred embodiment of the present invention control system and apparatus employs concave or cylindrically curved gratings instead of a lens or curved mirror/flat grating in a 2 f or 4 f configuration of the pulse shaping portion of the MIIPS unit. This minimizes the number of required optics and yields a more compact footprint or packaging size of the pulse shaper portion of the MIIPS unit. The particular curvature of the curved grating will serve the dual purposes of resolving the beam spectrally while also focusing resolved beams on the SLM. Thus, a focusing element (for example, a lens or mirror) can be eliminated, while it should be appreciated that this is independent of the SLM which may be a deformable mirror but preferably a liquid crystal modulator. A suitable concave grating can be obtained from Newport Inc. or Edmund Optics Inc.

One of the goals of the variations disclosed with regard to FIGS. 13 and 14 is to maximize the Full With At Half Maximum (hereinafter "FWHM"), in other words the frequency bandwidth, of the laser pulse in order to obtain the shortest duration pulses. Another preferred embodiment seeks to achieve the opposite result where a laser system produces a greater bandwidth and employs MIIPS with amplitude control to reduce the bandwidth to a desired value. This would provide very reproducible results with laser outputs that are always exactly the same. In this exemplary embodiment, an SLM uses MIIPS, and optionally BPS, to optimize the amplitude of an amplified ultra-short laser source to the desired specification of the user. The MIIPS unit measures the spectrum and subsequently narrows the pulse bandwidth via the SLM pulse shaper. For example, if the amplified laser output is 30 nm FWHM, centered at 800 nm, the present use of MIIPS is expected to deliver a pulse output centered at 780 nm with a 5 nm bandwidth through the integrated or stand-alone MIIPS unit.

Figure 24:
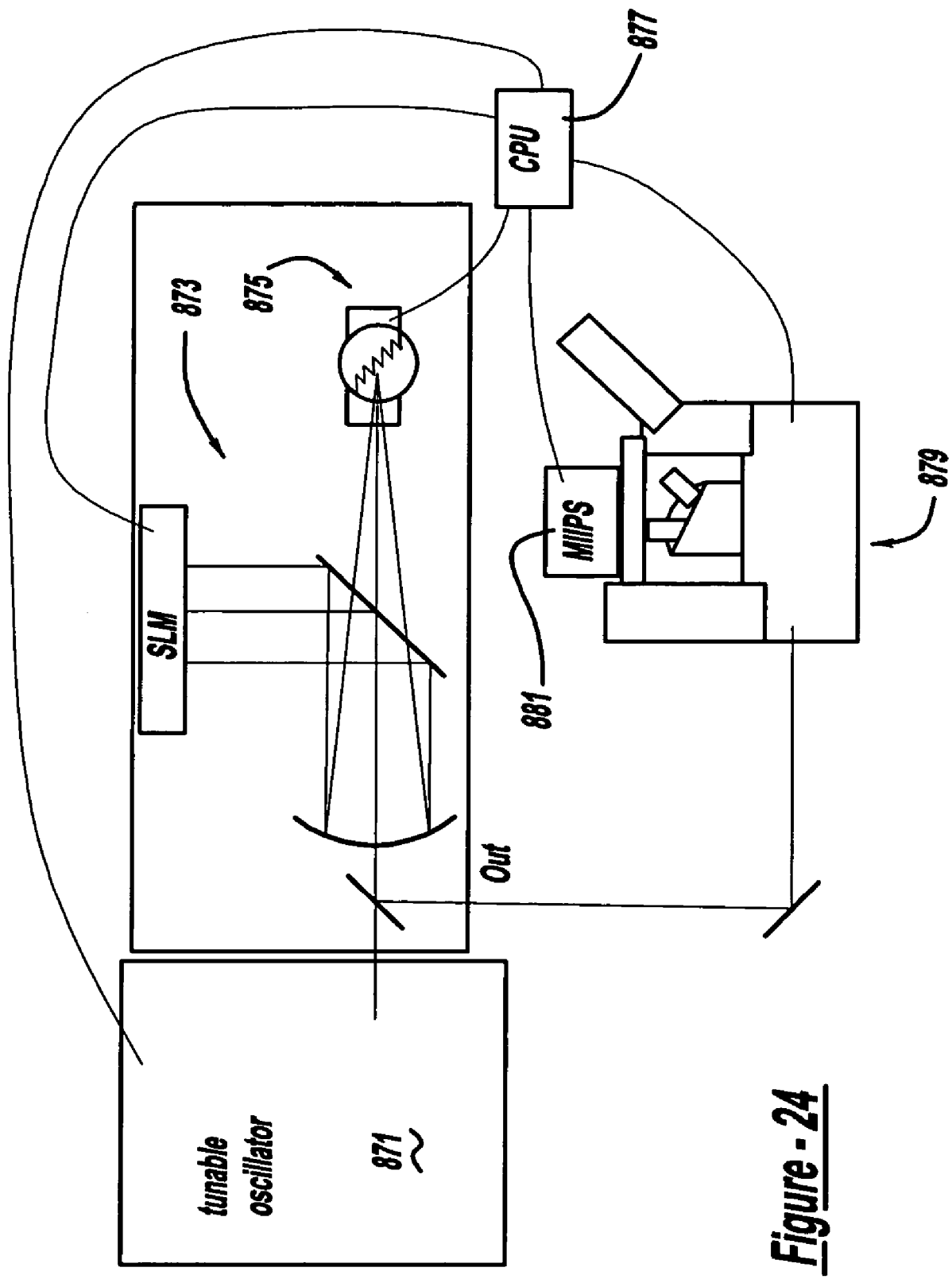
FIG. 24 is a diagrammatic view showing a thirteenth preferred embodiment of the present invention using a microscope.

FIG. 24 represents a tunable, femtosecond laser, using MIIPS methodology, applied by way of a non-limiting example, to an optical microscope 879. An exemplary inverted microscope can be obtained from Nikon Inc. as Model No. TE200 and TE300. The laser pulse enters the microscope through a port and is reflected thereafter toward the objective. A tunable Chameleon-XR brand laser, obtained from Coherent Inc., or Mai Tai brand laser which can be obtained from Spectra-Physics Inc., may also be employed. This system can be applied to imaging as well as microscopy. The laser beam pulse output of a tunable oscillator 871 is directed to a pulse shaper 873. Shaper 873 has a rotating and translating grating 875 that receives the input pulse and rotates it according to its wavelength in order to maintain the alignment of the shaper. A programmable CPU controller 877 is connected with the laser and automatically directs the grating to the correct angle. The output pulse is thereafter directed from the shaper to an imaging device, for example microscope 879. The microscope is connected to and communicates with controller 877 sending signals indicative of which microscope objective is being used. The phase distortions introduced by the microscope objective at the wavelength of excitation are stored in a memory database in controller 877 and automatically adjusted by translation of the grating in the shaper, then the higher order terms by the shaper. The system automatically performs a MIIPS characterization measurement to fine tune the compensation and calibration of the system. A MIIPS detection box or unit 881 at the output of the objective has a nonlinear medium to generate the second harmonic and it also has a compact spectrometer directly therein or remotely coupled thereto used to obtain the spectrum of the second harmonic and send the corresponding signals to the controller for extracting the phase compensation based on the MIIPS software. This allows for automatic compensation, correction and producing of transform limited pulses at the microscope sample position using the MIIPS technique. This optionally allows for further optimization of the spectral phase of ultra-short pulses to maximize or minimize excitation of the microscope sample, such as selective 2-photon excitation. The MIIPS box can be optionally placed upstream of the amplifier, downstream amplifier or inside the amplifier's stretcher.

Figure 25:
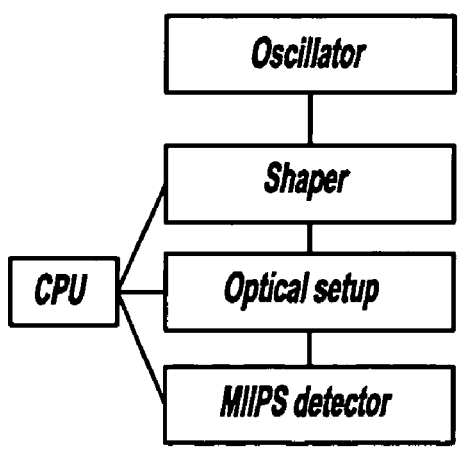
FIGS. 25-28 are block diagrams showing control system variations of a fourteenth preferred embodiment of the present invention.
Figure 26:
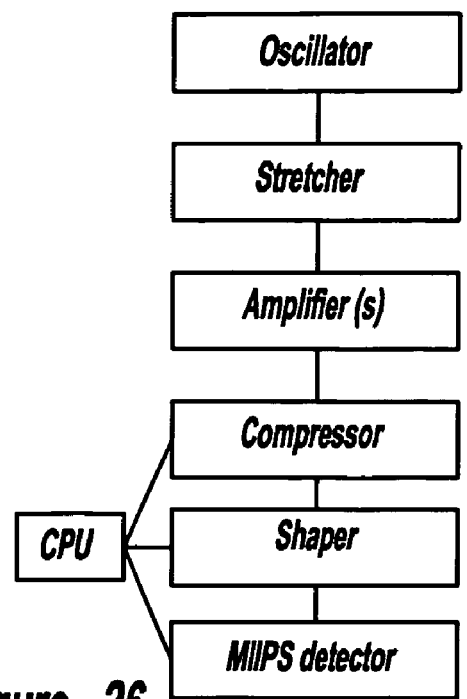
Figure 27:
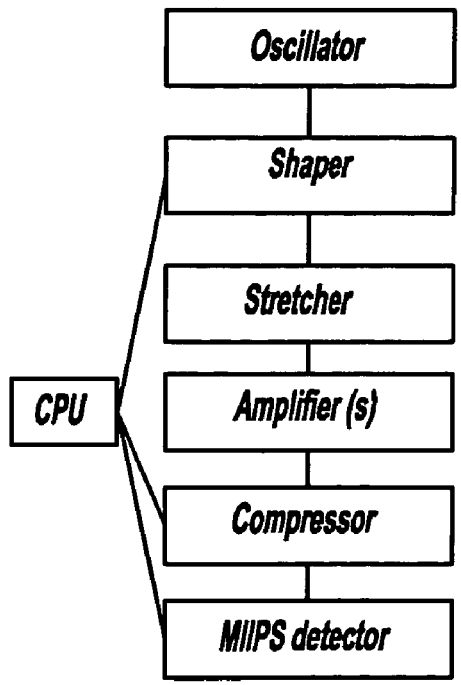
Figure 28:
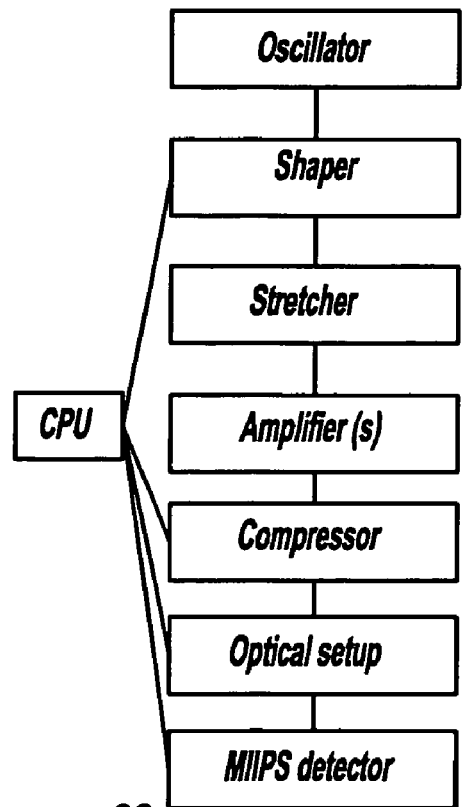

FIGS. 26 through 28 illustrate various preferred configurations of the control system employing MIIPS-based pulse shaping. Turning to FIG. 25, a femtosecond laser oscillator, pulse shaper, optical setup, MIIPS detector and CPU controller are provided. The controller communicates with the shaper, optical setup and MIIPS detector to calibrate the pulses at the location of the sample. The controller further ensures that the pulse with the desired phase and amplitude properties interacts with the specimen, while correcting any phase deformations that could be introduced by the optical setup. The configuration of FIG. 26 uses chirped pulse amplification where the pulse shaper and MIIPS detector are placed downstream after the amplification and compression. The controller obtains data from the detector and converts it into phase information from which it automatically controls hardware in the compressor to minimize quadratic and cubic phase deformations. The controller subsequently directs the shaper to compensate for higher order deformations and to introduce a compensation phase. The pulse shaper may then be used to introduce phase and amplitude modulation as desired by the user.

The programmable software instructions used with any of the MIIPS controllers described herein is illustrated in FIGS. 16 through 19. These software instructions are preferably run in an automated and closed loop manner in real-time, however, manual user input, variation and result verification may alternately be desirable especially upon initial setup of a new specimen type or in a laboratory-type setting. The software utilizes MIIPS, and optionally BPS, principles of introducing a well known spectral phase function via the SLM pulse shaper to the ultra-short femtosecond pulses with the intention to measure the unknown spectral phase inherent in the original ultra-short pulses, and subsequently compensate by pulse shaping the pulses and iterative or one shot-direct manner. It should further be appreciated that MIIPS and/or BPS methodology is applicable to all of the end use applications disclosed herein; this includes MALDI, sequencing, cleaving, microscopy, OCT, PDT, quantum computing, photo polymerization, and communications. It is equally applicable that upstream or downstream placement of the MALDI unit, or components thereof, can also be employed for all of the end-use applications disclosed herein depending upon the desired pulse duration, existing equipment and other case-by-case requirements.

Figure 16:
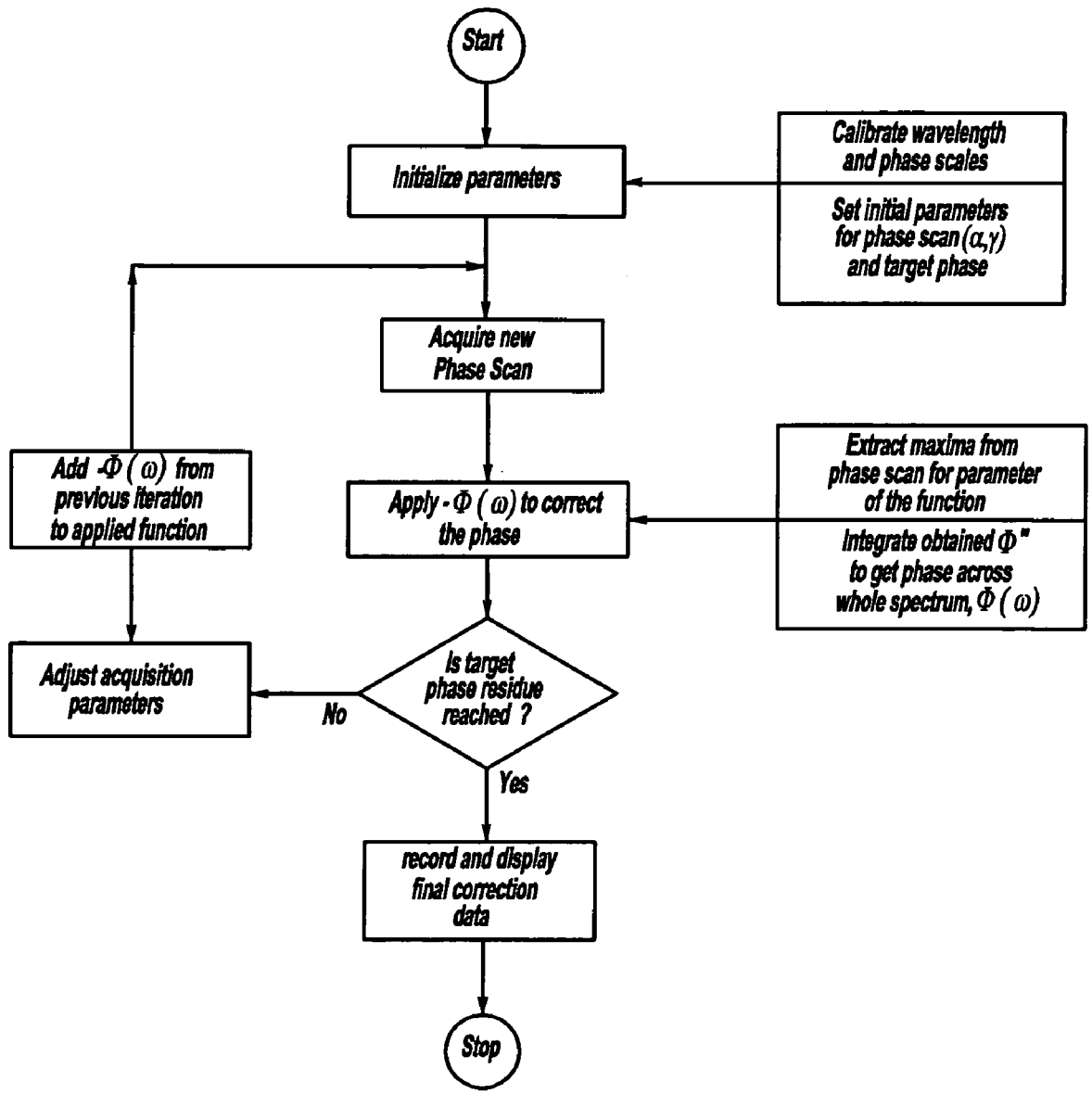
FIGS. 16 through 19 are flow charts for the method and computer software operation employed with any of the preferred embodiments of the present invention.
Figure 17:
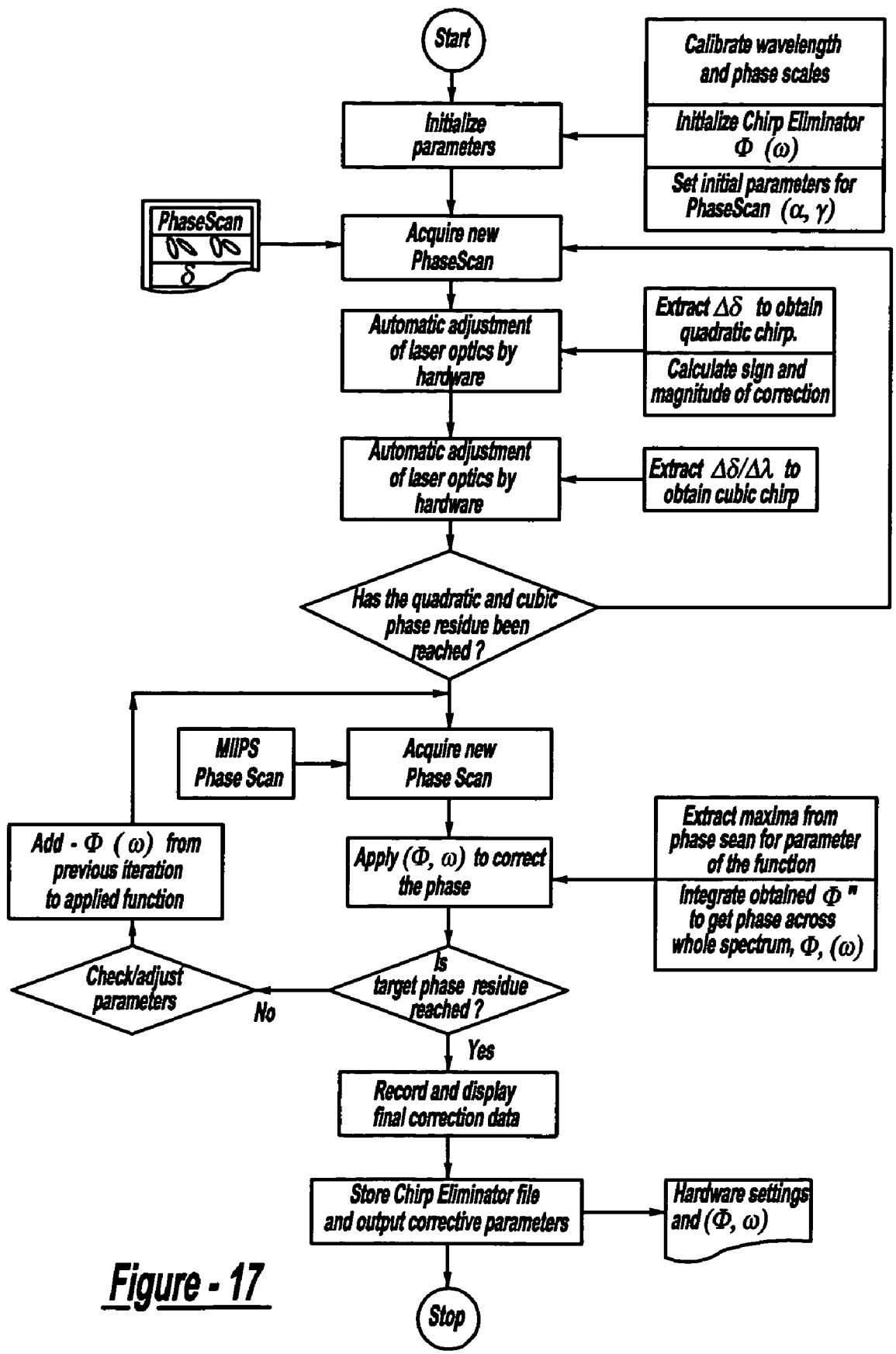
Figure 18:
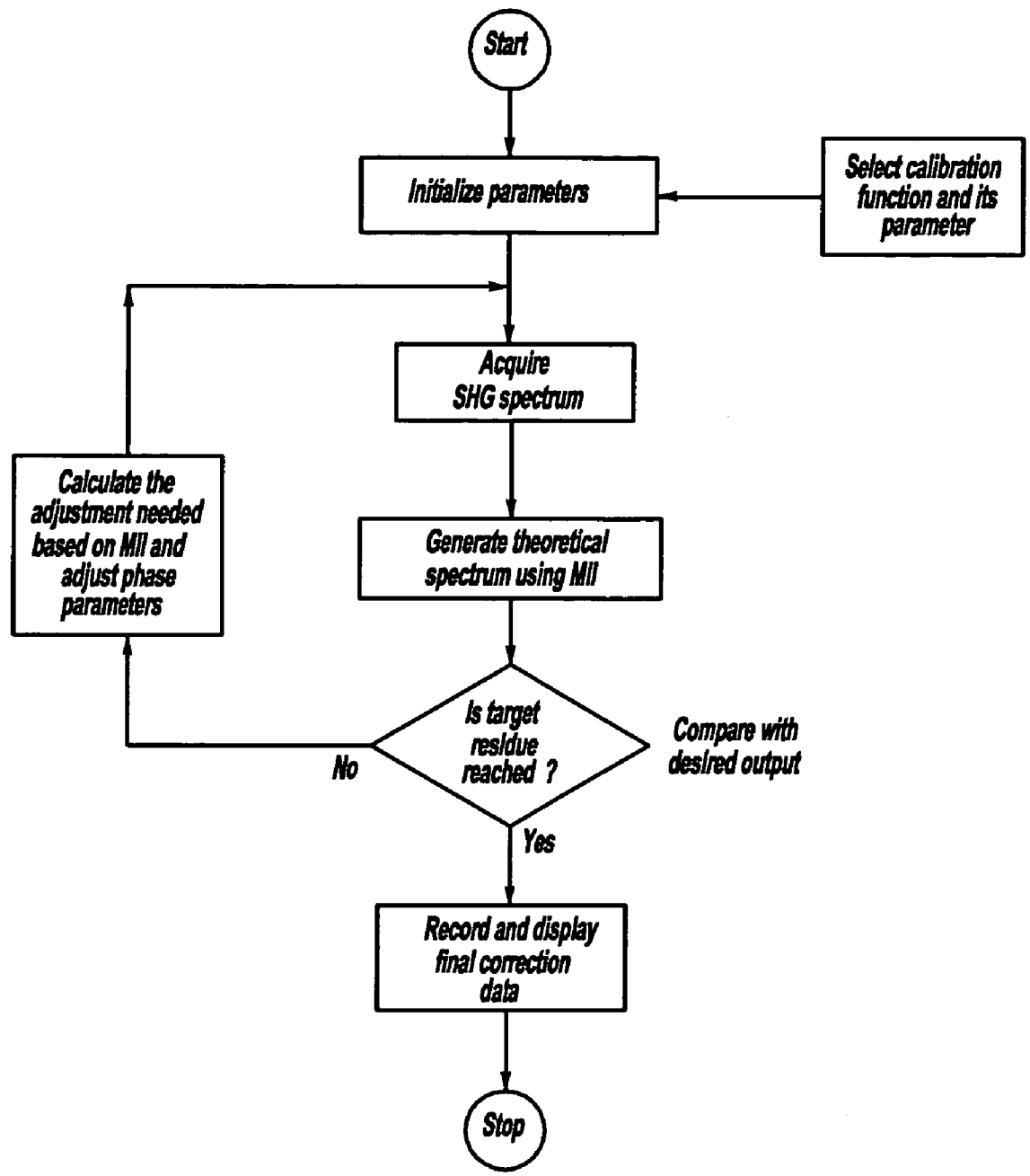
Figure 19:
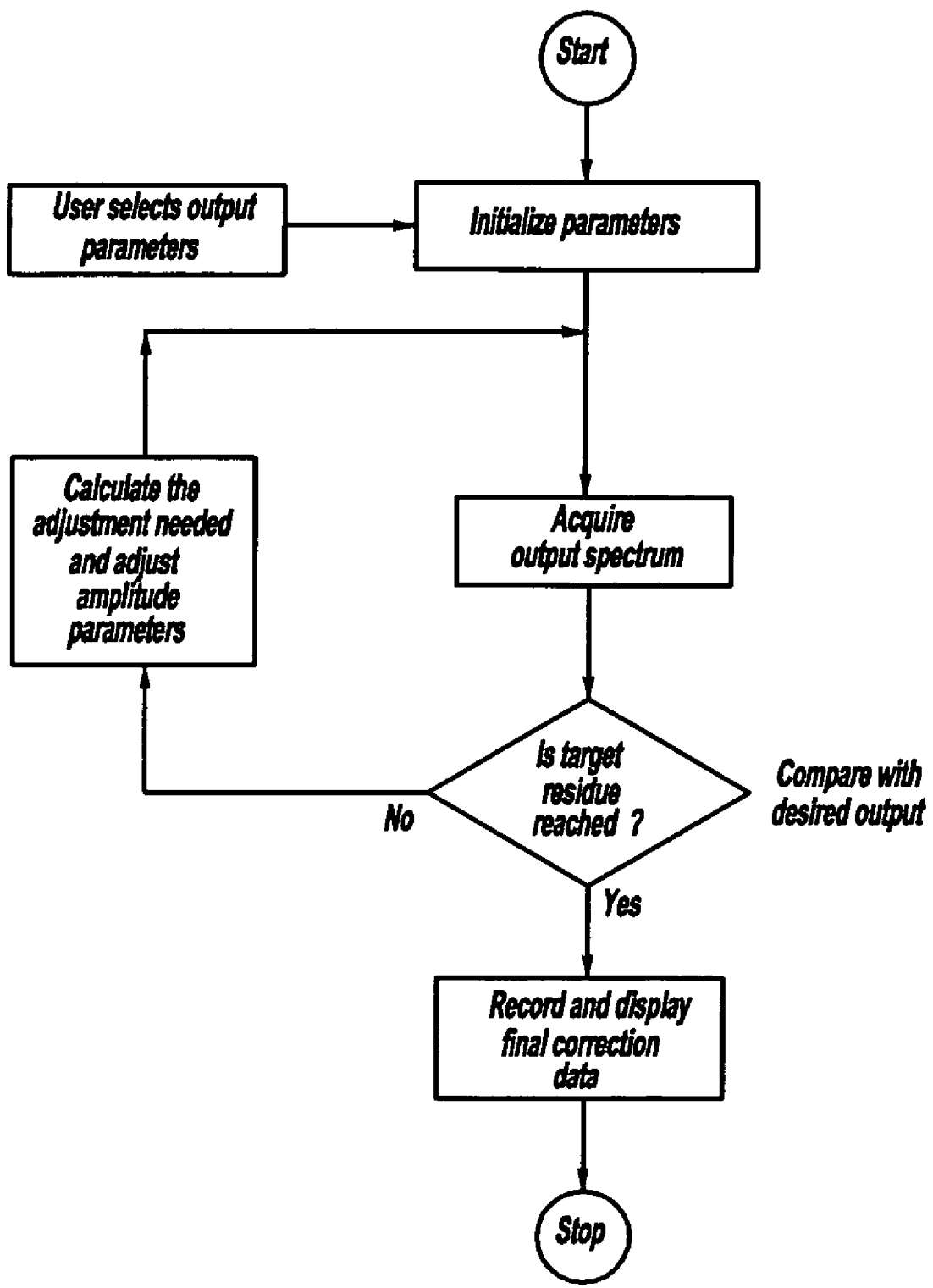

FIG. 16 represents a MIIPS software flow chart where after a new phase scan is acquired the data is used to extract the maxima from the phase scan for a function parameter to obtain the second derivative of the phase $\phi^{11}$. The phase across the entire spectrum $\phi(\omega)$ is obtained by double integration. By applying $-\phi(\omega)$ the phase in the pulse is corrected. If the correction is small enough then the target phase residue has been achieved. However, if the phase residue is still large the phase is corrected and a new phase scan is performed. Next, FIG. 17 is a software flow chart including a first cycle, where the quadratic and cubic phase distortions are corrected by optic hardware in the laser. Furthermore, FIG. 18 illustrates a software flow chart employing computer calculations which fine tune a phase function so that one can obtain precisely the nonlinear optical response predicted by theory. This specific flow chart method does not use MIIPS but instead uses MII to control 2-photon processes such as second harmonic generation. MII adjusts the phase parameters, however, the adjustments could alternately involve scanning certain parameters and manually evaluating their effects on the pulse output. Finally, FIG. 19 is a software flow chart employing calculations used when the user wants to specify the output spectrum of the laser. This can be used as a stand-alone application or together with phase control. In this figure, the output spectrum refers to the linear spectrum of the pulse and not to the SHG spectrum. The pulse shaper in this application modulates the amplitude of the pulse.

Referring now to FIG. 27, a laser system is provided which uses chirped pulse amplification. The shaper is placed upstream before the stretcher. The controller obtains data from the detector and converts it into phase information. The controller thereafter directs the hardware in the compressor to minimize quadratic and cubic phase deformations which it then uses to control the shaper to compensate for higher order deformations and to introduce a compensation phase into the pulse. The shaper subsequently can be used to introduce phase and amplitude modulation as desired by the user. Furthermore, the FIG. 28 configuration also uses chirped pulse amplification and the pulse shaper is located upstream before the stretcher. The controller obtains data from the MIIPS detector which it converts into phase information. The MIIPS detector, however, is located after an optical setup that is external to the laser, where the optical setup preferably includes a simple lens and mirror combination but could alternately include a telescope or microscope. The controller subsequently controls hardware in the compressor to minimize quadratic and cubic phase distortions which it uses to direct the shaper to compensate for higher order deformations and to introduce a compensation phase. This configuration may be optionally be used to also introduce phase and amplitude modulation as desired by user, and can be employed to ensure that the laser pulse interaction with the specimen has no undesired phase modulation.

An additional preferred embodiment of the present invention employs MIIPS and optionally BPS, in existing optical parametric amplifiers (hereinafter "OPA") in order to tune the central wavelength of the output and to correct for phase distortions of the beam output. The processes in OPAs are nonlinear by nature and a desired wavelength can be achieved by shaping the spectral phase of light input in the OPA or non-collinear optical parametric amplifier (hereinafter "NOPA") using calculations involving MIIPS and BPS. The SLM controlled by MIIPS and BPS in 2 f or 4 f configurations can be placed upstream before the OPA/NOPA or integrated into the OPA/NOPA; it can also be used to affect only non-classical light (in the nanosecond pulse duration range), affect only white light generation, affect only blue light generation, or both, depending on the end use application.

Calibration of a Phase-Only SLM Inside a Pulse Shaper

This calibration is very important before MIIPS can be done, to determine the amount of voltage needed to achieve phase retardation. The SLM can be calibrated before the installation into the laser system if the input laser parameters are known ahead of time. Ideally the calibration should be done on the complete system when it is fully integrated.

Procedure:
1. Have the femtosecond laser being shaped transmit through the shaper setup.
2. Flip-up into position a zeroth-order half wavelength plate to rotate the polarization of the input beam to 45 degrees.

3. Flip-up into position a polarizer set at 45 degrees at the output of the shaper.
4. Drive the voltage of all the pixels in the SLM from 0 to the highest allowable voltage.
5. As the voltage is driven up, record the output spectrum from the shaper at the fundamental wavelength range. Make sure that the resolution in the spectrometer is sufficient to record changes on the individual pixels.
6. Calculate the calibration curve for each pixel given the transmission curve obtained from the corresponding wavelength range in the spectrum.

When the polarization is rotated away from the incident, horizontal direction, it is attenuated by the second polarizer. A rotation of 90 degrees results in zero transmission. This polarization dependence is used for calibration of the pulse shaper. Ramping the voltage of the liquid crystal plate results in the transmission function which can be used to accurately calibrate the dependence of retardance on voltage.

The total retardation $\phi$ is determined experimentally taking advantage of changes in the transmission given by $$T(V) = \cos^2[\pi R(V)/\lambda], \quad (2)$$

where R(V) is the retardance as a function of voltage introduced by the SLM unit. By scanning the voltage V, one can measure T(V) and calculate R(V) (except for a constant that can be set to zero). Finally, one can calculate the phase delay $\phi$ according to $$\phi(V) = \pi R(V)/\lambda.$$

The software module takes into account the differences in the index of refraction for the different frequencies in the laser pulse. This is especially important for tunable laser systems or for pulses that are 50 fs and shorter. The calibration is performed for each pixel in the shaper at the frequency of light that transmits through it. The result is a calibration that can be trusted to better than 0.01 radians.

7. When the calibration is complete, flip the half wavelength plate out of the input beam and the polarizer out of the output beam. The system is now ready for MIIPS.

Calibration of a phase-amplitude SLM inside a pulse shaper. This procedure is carried out with the amplifier turned off.
1. Have the femtosecond laser being shaped transmit through the shaper setup.
2. Drive the voltage of all the pixels in the SLM mask 1 from 0 to the highest allowable voltage, while the SLM mask 2 is kept at the highest allowable voltage.
3. As the voltage is driven up, record the output spectrum from the shaper at the fundamental wavelength. Make sure that the resolution in the spectrometer is sufficient to record changes on an individual pixel.
4. Drive the voltage of all the pixels in the SLM mask 2 from 0 to the highest allowable voltage, while the SLM mask 1 is kept at the highest allowable voltage.

Calculate the calibration curve for each pixel given the transmission curve obtained from the corresponding wavelength range in the spectrum as follows: When the optical axis of the liquid crystal mask is oriented at a 45° angle with respect to the polarization of the incident electric field, polarization rotation is introduced in addition to retardance. When two such SLM units are lapped back-to-back and in opposite angles of rotation, and they are flanked by input and output polarizers, one can control both phase and amplitude of the transmitted light. [74-76] Ramping the voltage of one of the liquid crystal plates while maintaining the other at a constant voltage results in the transmission function, which can be used to accurately calibrate the dependence of retardance on voltage.

The total retardation $\phi$ is determined experimentally taking advantage of changes in the transmission given by $$T = \cos^2[\pi(R_1(V_1) - R_2(V_2))/\lambda], \quad (2)$$

where R(V) is the retardance as a function of voltage introduced by each SLM unit. By fixing $V_2$ and scanning $V_1$, one can measure $T(V_1)$ and calculate $R_1(V_1)$ (except for a constant). By measuring $T(V_2)$ while keeping $V_1$ constant, one can obtain $R_2(V_2)$. Knowing $R_1(V_1)$ and $R_2(V_2)$, one can calculate the phase delay $\phi$ according to $$\phi = \pi(R_1(V_1) + R_2(V_2))/\lambda.$$

The software module developed by Biophotonic Solutions Inc. takes into account the differences in the index of refraction for the different frequencies in the laser pulse. This is especially important for pulses that are 50 fs and shorter. The calibration, therefore, is performed for each pixel in the shaper at the frequency of light that transmits through it. The result is extraordinary calibration which has been demonstrated with pulses as short as 8 fs.

Hardware Packaging and Stabilization

Figure 29:
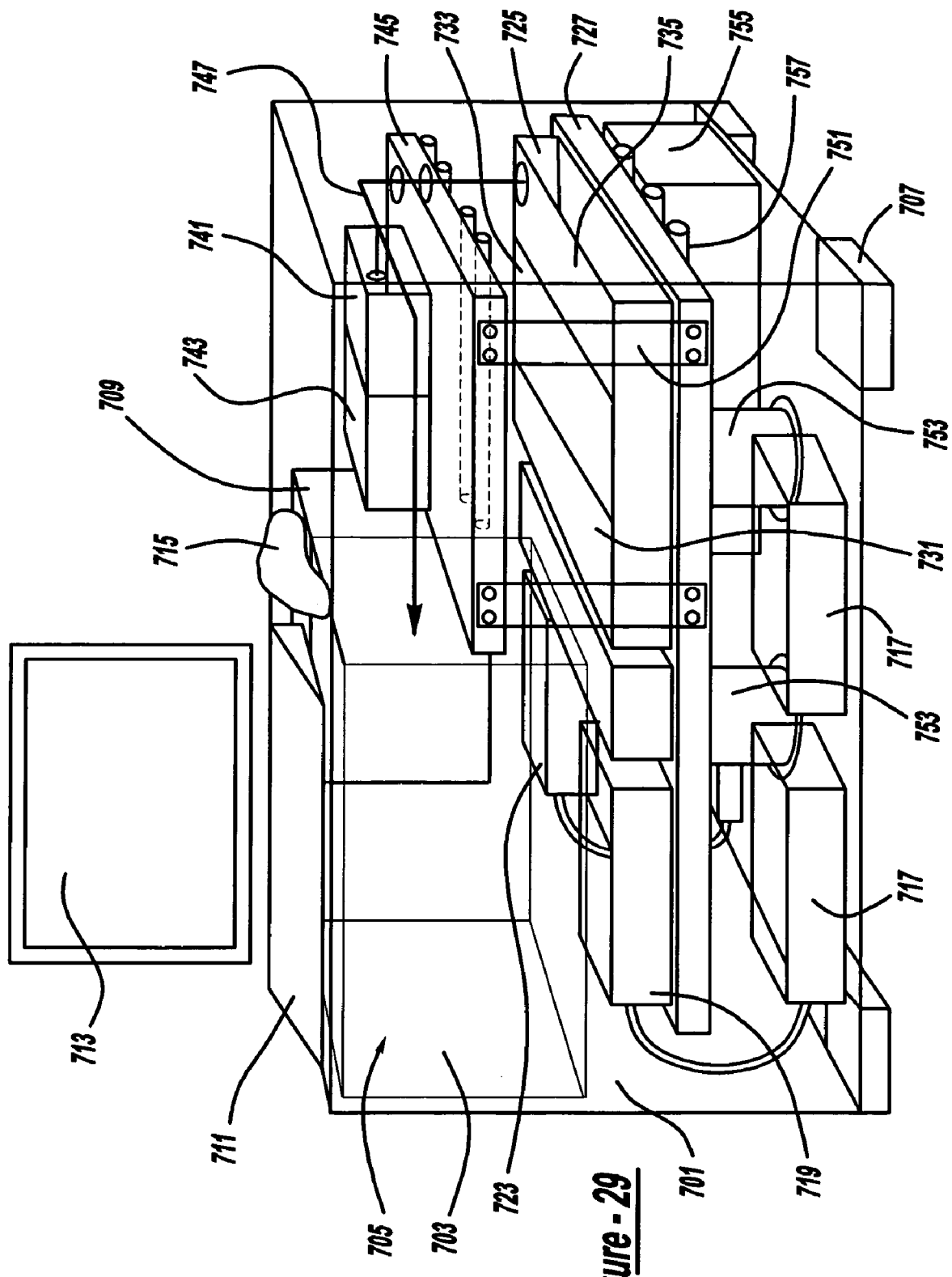
FIG. 29 is a diagrammatic and perspective view showing a fifteenth preferred embodiment of the present invention in a self-contained housing.

A preferred packaging arrangement for the control system and apparatus of the present invention is shown in FIG. 29. A totally enclosed and self-contained sheet steel housing 701 has a slidable or rotatable door 703 allowing access to an application chamber 705 which contains a support upon which a specimen is placed by the user. A set of feet or rollers 707 support housing 701 off of a factory, hospital or laboratory floor. CPU controller 709 is located within housing 701 and an input keyboard 711 and mouse 715, and output CRT screen 713 are located on the outside of or attached within but externally operable from outside housing 701. Other input and output devices such as buttons, on/off/warning lights and printers may also be provided fully or partially external to housing 701. Power supplies 717, an oscillator pump 719, an oscillator 721, an amplifier pump 723 and amplifier 725 are further mounted to a shelf 727 within housing 701. Amplifier 725 includes a stretcher and shaper section 731, a regenerative amplifier section 733 and a compressor section 735. SHG optics 741 and a compact spectrometer 743 are preferably mounted onto a second shelf 745 inside housing 701. The laser beam pulse output is indicated by line 747 and is preferably carried between components by fiber optic cables or the like. The portion of housing 701 containing at least the amplifier and SHG optics are hermetically sealed and temperature controlled. The remainder of housing has a filtered air flow, ventilation system, with fans, to cool the power supplies and CPU. Shelves 727 and 745 are preferably made from a thermally stable, breadboard-type material and are coupled to each other by way of thermally stable columns 751. A set of vibrational isolators 753 support at least shelf 727 off of the bottom of housing 701, and additional vibrational isolators can be employed at optional additional coupling areas between one or more of the shelves and side walls of housing 701. Each vibrational isolator 753 is preferably a Newport Inc. Model I-2000 device.

A water chiller 755 is located within housing 701 and is fluidically coupled to a set of pipes 757 running in a serpentine path under shelf 727 and optionally, shelf 745. The chilled water system maintains the desired temperature range of 28° C.+/−1° C. to all of the oscillator and MIIPS components. The application chamber can be used for at least MALDI, mass spectrometry, micro-machining, PDT for blood and other fluids, breath analysis, biohazard analysis of emissive signatures, chemical agent analysis by mass spectrometry, sequencing, cleaving, photo-polymerization, and the like.

The present invention ideally reduces thermally and vibrationally induced changes in the optical systems. Thus, room temperature variations affecting the dimensions and alignment of optic components due to temperature of the equipment is minimized or maintained constant. The present invention further saves expense since the components within the housing can be temperature controlled while the surrounding factory environment can be open to the outside atmosphere or at temperatures more comfortable for the users.

While various embodiments have been disclosed herein, it should be appreciated that other modifications may be made that are covered by the system and methods of the present invention. For example, alternate lasers, chemicals, optics, software and programmable controllers can be employed as long as they function as described. As a further example, phase characterization of the output pulse with or without the automatically operated, computer controlled mirror and grating movement for tuning oscillator optics can alternately be used with frequency resolved optical gating (FROG) or spectral phase interferometry for direct electric-field reconstruction (SPIDER) phase measurements that are then used to calculate a compensation phase that is introduced with a pulse shaper instead of using the preferred MIIPS method. The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. Computer software stored in non-transitory computer memory, the computer software comprising:
    (a) first instructions operably causing an introduction of a known spectral phase function through pulse shaping ultra-short, femtosecond photonic laser beam pulses;
    (b) second instructions operably using measurements of an unknown spectral phase in at least one of the pulses; and
    (c) third instructions operably causing compensation for undesired distortions in at least one of the pulses through pulse shaping.

2. The computer software as recited in claim 1, further comprising additional instructions iteratively conducting the compensation and compensating for at least third order phase distortions in the at least one of the pulses.

3. The computer software as recited in claim 1, further comprising additional instructions directly conducting the compensation in one shot.

4. The computer software as recited in claim 1, further comprising additional instructions causing binary phase shaping to at least one of the pulses.

5. The computer software as recited in claim 1, further comprising additional instructions automatically controlling multiphoton intrapulse interference in at least one of the pulses after it has been chirped.

6. The computer software as recited in claim 1, further comprising:
    fourth instructions obtaining a second derivative of a phase of at least one of the pulses;
    fifth instructions obtaining a value representative of a phase across the entire spectrum of the at least one of the pulses by using double integration; and
    sixth instructions applying the negative of the value in order to correct distortions in the at least one of the pulses.

7. The computer software as recited in claim 1, further comprising:
    a pulse shaper changing a characteristic of the pulses in response to at least one of the instructions;
    a spectrometer assisting in the measurement of the unknown spectral phase; and
    a computer programmed with and operating the instructions.

8. The computer software as recited in claim 1, wherein the pulse shaping assists in both the measurement and compensation of the pulse distortions.

9. The computer software as recited in claim 1, wherein at least one of the ultra-short pulses has a duration of less than 20 femtoseconds.

10. A computer program stored in non-transitory memory, the computer program comprising instructions, wherein:
    (a) at least one of the instructions automatically characterizes undesired distortions in at least one laser beam output;
    (b) at least another of the instructions calculates a phase of the at least one laser beam output; and
    (c) at least a further of the instructions automatically corrects the distortions in the at least one laser beam output, at least in part by controlling multiphoton intrapulse interference.

11. The computer program as recited in claim 10, further comprising additional instructions directly measuring a second derivative of the phase.

12. The computer program as recited in claim 10, wherein the instructions characterize and compensate distortions in the at least one laser beam output which includes laser beam pulses having durations less than 100femtoseconds.

13. The computer program as recited in claim 10, further comprising additional instructions:
    causing an introduction of a known spectral phase function through pulse shaping the at least one laser beam output;
    causing a measurement of an unknown spectral phase in the at least one laser beam output; and
    causing binary phase shaping to the at least one laser beam output.

14. The computer program as recited in claim 10, further comprising:
    a laser emitting the at least one laser beam output;
    a shaper shaping the at least one laser beam output to assist with the correcting; and
    a computer operating the instructions.

15. The computer program as recited in claim 10, further comprising a pulse shaper assisting in controlling the multiphoton intrapulse interference in response to at least one of the instructions.

16. The computer program as recited in claim 10, wherein pulse shaping, controlled by at least one of the instructions, assists in both the characterizing and the correcting of the distortions, which include at least third order phase distortions.

17. Computer software stored in non-transitory computer memory, the computer software comprising:
    (a) first instructions measuring phase distortions in at least one laser beam pulse that is compressed;
    (b) second instructions characterizing the at least one pulse;
    (c) third instructions using values representative of amplitude and phase spectral profiles during computer calcuations;
    (d) fourth instructions receiving at least one signal from a spectrometer receiving the at least one pulse;
    (e) fifth instructions controlling a pulse shaper;

(f) sixth instructions determining the spectral intensity and spectral phase of the at least one pulse;

(g) seventh instructions determining a correction to reduce undesired distortion in the at least one pulse; and (h) eighth instructions generating a spectral phase scan trace of the at least one pulse;

wherein the software causes correction of the undesired distortion by substantially closed loop calculations without a learning algorithm.

18. The computer software as recited in claim 17, further comprising additional instructions iteratively conducting the correction.

19. The computer software as recited in claim 17, further comprising additional instructions directly conducting the correction in one shot.

20. The computer software as recited in claim 17, further comprising additional instructions causing binary phase shaping to the at least one pulse.

21. The computer software as recited in claim 17, further comprising additional instructions automatically controlling multiphoton intrapulse interference in the at least one pulse after it has been chirped.

22. The computer software as recited in claim 17, further comprising:

ninth instructions obtaining a second derivative of a phase of the at least one pulse;

tenth instructions obtaining a value representative of a phase across the entire spectrum of the at least one pulse by using double integration; and eleventh instructions applying the negative of the value in order to correct distortions in the at least one pulse.

23. The computer software as recited in claim 17, further comprising:

(a) ninth instructions operably causing a known spectral phase function to be introduced through pulse shaping the at least one pulse which includes multiple ultrashort, femtosecond laser beam pulses;

(b) tenth instructions operably causing measuring an unknown spectral phase in at least one of the pulses; and (c) eleventh instructions operably causing compensating for undesired distortions in at least one of the pulses through pulse shaping.

24. The computer software as recited in claim 17, further comprising additional instructions acquiring a SHG spectrum and automatically correcting the pulse for the measured distortions through pulse shaping.

25. The computer software as recited in claim 17, wherein the at least one pulse has a duration less than 100 femtoseconds, further comprising additional instructions automatically moving optical hardware in response to computer calculations.

26. The computer software as recited in claim 17, further comprising additional instructions controlling multiphoton intrapulse interference in the at least one pulse at least in part by varying a pulse shape introduced into the at least one pulse without use of an interferometer.

27. The computer software as recited in claim 17, further comprising a microprocessor programmed with the instructions, at least some of the instructions changing a pulse shaping characteristic of the pulse shaper.

28. A computer program stored in non-transitory memory, the computer program comprising:

(a) first instructions operably causing a known spectral phase function to be introduced into laser beam pulses;

(b) second instructions causing an unknown spectral phase to be measured in at least one of the pulses;

(c) third instructions causing compensation for undesired distortions in at least one of the pulses; and (d) fourth instructions causing at least steps (b) and (c) to be performed automatically by calculation without use of a learning algorithm.

29. The computer program of claim 28, further comprising: instructions for acquiring an initial phase scan;

instructions for automatically adjusting the optic hardware to correct the phase distortions;

instructions for determining if at least one of quadratic and cubic phase residue has been reached;

instructions for acquiring a subsequent phase scan;

instructions for applying $-\phi(\omega)$ to correct said subsequent phase;

instructions for determining if the target phase residue has been reached; and instructions for storing a compensation phase file and laser beam output corrective parameters.

30. The computer program of claim 29, wherein the instructions for initializing parameters comprises initializing a phase compensation $-\phi(\omega)$.

31. The computer program of claim 28, further comprising setting initial parameters for a phase scan $(\alpha\gamma\delta)$ using a reference function dependent on initial parameters $f(\alpha\gamma\delta)$ and a target residual phase.

32. The computer program of claim 29, wherein the instructions for automatically adjusting the optic hardware comprises calculating the sign and magnitude of correction.

33. The computer program of claim 29, wherein the instructions for automatically adjusting the optic hardware comprises repeating the automatic adjustment of the optic hardware.

34. The computer program of claim 29, wherein if in the instructions for determining if at least one of the quadratic and cubic phase residue has been reached, it is determined that the quadratic and cubic phase residue has not been reached, the steps are repeated beginning with the instructions for acquiring an initial phase scan until it is determined that the at least one of quadratic and cubic phase residue queried in the instructions has been reached.

35. The computer program of claim 29, wherein the instructions for applying $-\phi(\omega)$ to correct the subsequent phase comprises extracting maxima from the phase scan for the parameter of the function.

36. The computer program of claim 29, wherein the instructions for applying $-\phi(\omega)$ to correct the subsequent phase comprises integrating the obtained $\phi''$ to obtain a phase across the whole spectrum, $-\phi(\omega)$.

37. The computer program of claim 29, further comprising instructions adding $-\phi(\omega)$ from the previous iteration to the applied compensation function $\phi(\omega)$.

38. The computer program of claim 29, wherein the instructions for storing a phase compensation file and output corrective parameters further comprises adjusting hardware settings and the accumulated $\phi(\omega)$.

39. The computer program of claim 28, further comprising instructions for initializing parameters comprising calibrating wavelength and phase scales.

40. The computer program of claim 28, further comprising additional instructions causing a suppression of three photon or greater transitions in at least one of the pulses, wherein at least one of the pulses has a duration less than 10 femtoseconds.

41. The computer program of claim 28, further comprising:

(a) additional instructions receiving measurement signals from a spectrometer; and (b) additional instructions automatically controlling a pulse shaper to introduce a distortion compensation in at least one of the pulses.

42. The computer program of claim 28, further comprising:
a pulse shaper changing a characteristic of the pulses in response to at least one of the instructions;
a spectrometer assisting in the measurement of the unknown spectral phase; and
a computer programmed with and operating the instructions.

43. The computer program of claim 28, wherein pulse shaping, controlled by at least one of the instructions, assists in both the measurement and the compensation of the distortions, which include at least third order phase distortions.

44. Computer software stored in non-transitory computer memory, the computer software comprising:
(a) first instructions causing a pulse shaper to introduce a calibrated phase into at least one photonic laser beam pulse, each pulse having a duration of less than 100 femtoseconds;
(b) second instructions causing generation of a spectral phase scan trace of the at least one pulse;
(c) third instructions characterizing the at least one pulse;
(d) fourth instructions determining a correction to reduce undesired distortion in the at least one pulse; and
(e) fifth instructions causing the pulse shaper to introduce a phase that corrects the undesired phase distortions;
wherein the software causes correction of the undesired distortion by substantially automatic software calculations, without a learning algorithm and without an interferometer.

45. A computer program apparatus comprising software running on a computer, the software automatically determining and correcting phase distortions of at least one photonic laser beam output by calculated corrections with the assistance of pulse shaping, within three iterations to yield a transform-limited laser beam output, but without an interferometer.

46. The computer program apparatus of claim 45, wherein the software is operated on the computer to vary phase shaping between a plurality of laser beam output which are pulses.

47. The computer program apparatus of claim 45, wherein the software is operated on the computer to control sending of a communications signal through the at least one laser beam output to a remote communications receiver.

48. The computer program apparatus of claim 45, wherein the software is operated on the computer to control the at least one laser beam output in medical use upon living tissue.

49. The computer program apparatus of claim 45, wherein the software is operated on the computer to prevent three photon damage in a pulse duration less than 100 femtoseconds.

50. The computer program apparatus of claim 45, wherein the software is operated on the computer to control the at least one laser beam output in microscopy where at least one output pulse duration is less than 20 femtoseconds.

51. A method of using software stored in non-transient memory and adapted for use on a computer, the method comprising:
(a) using the software to introduce a known spectral phase function into photonic laser beam pulses;
(b) using the software to measure an unknown spectral phase in at least one of the pulses; and
(c) using the software to correct for an undesired distortion in at least one of the pulses through use of calculated corrections without use of a learning algorithm.

52. The method of claim 51, further comprising using the software to cause a suppression of three photon or greater transitions in at least one of the pulses, wherein at least one of the pulses has a duration less than 20 femtoseconds.

53. The method of claim 51, further comprising using the software for:
obtaining a second derivative of a phase of the at least one pulse;
obtaining a value representative of a phase across the entire spectrum of the at least one pulse by using double integration; and
applying the negative of the value in order to correct distortions in the at least one pulse.

54. The method of claim 51, further comprising repeating steps (a)-(c) within three iterations to obtain a transform-limited pulse without use of an interferometer.

55. The method of claim 51, further comprising using the software to cause a pulse shaper to assist in both the measuring and the correcting of pulse distortions.

* * * * *

UNITED STATES PATENT AND TRADEMARK OFFICE
CERTIFICATE OF CORRECTION

PATENT NO. : 7,973,936 B2
APPLICATION NO. : 11/219572
DATED : July 5, 2011
INVENTOR(S) : Marcos Dantus It is certified that error appears in the above-identified patent and that said Letters Patent is hereby corrected as shown below:

Title Page, Item (56), References Cited, Other Publications, page 8, column 2, Reference No. 12, "123004-1123004-4" should be --123004-1-123004-4--.
Title Page, Item (56), References Cited, Other Publications, page 10, column 2, Reference No. 13, "Otober" should be --October--.
Title Page, Item (56), References Cited, Other Publications, page 11, column 1, Reference No. 15, "anularly" should be --annularly--.
Title Page, Item (56), References Cited, Other Publications, page 12, column 2, Reference No. 8, "chioropropene" should be --chloropropene--.
Title Page, Item (56), References Cited, Other Publications, page 13, column 2, Reference No. 17, "by by use" should be --by use--.

In the Specifications
Column 2, line 11, "a" should be --as--.
Column 6, line 20, "than" should be --then--.
Column 8, line 59, "here in after" should be --hereinafter--.
Column 12, line 31, "Δ" should be --λ--.
Column 14, line 17, "OPP076413))" should be --OPP076413)--.
Column 14, line 22, "(C₅II₅NO₂)" should be --(C₅H₅NO₂)--.
Column 17, line 2, "isothiocyannate" should be --isothiocyanate--.
Column 17, line 3, "isoccyanate" should be --isocyanate--.
Column 17, line 37, "θ-carbon" should be --δ-carbon--.

Signed and Sealed this
Second Day of July, 2013

Teresa Stanek Rea
*Acting Director of the United States Patent and Trademark Office*